US012259395B2

(12) United States Patent
Liu

(10) Patent No.: US 12,259,395 B2
(45) Date of Patent: *Mar. 25, 2025

(54) CATABODIES AND METHODS OF USE THEREOF

(71) Applicant: AB Studio Inc., Hayward, CA (US)

(72) Inventor: Yue Liu, Foster City, CA (US)

(73) Assignee: AB Studio Inc., Hayward, CA (US)

( * ) Notice: Subject to any disclaimer, the term of this patent is extended or adjusted under 35 U.S.C. 154(b) by 991 days.

This patent is subject to a terminal disclaimer.

(21) Appl. No.: 17/268,933

(22) PCT Filed: Aug. 16, 2019

(86) PCT No.: PCT/US2019/046903
§ 371 (c)(1),
(2) Date: Feb. 16, 2021

(87) PCT Pub. No.: WO2020/037258
PCT Pub. Date: Feb. 20, 2020

(65) Prior Publication Data
US 2021/0190796 A1    Jun. 24, 2021

Related U.S. Application Data

(60) Provisional application No. 62/765,150, filed on Aug. 17, 2018.

(51) Int. Cl.
C07K 16/18        (2006.01)
C12N 9/00         (2006.01)
G01N 33/564       (2006.01)
G01N 33/68        (2006.01)

(52) U.S. Cl.
CPC ......... *G01N 33/6854* (2013.01); *C07K 16/18* (2013.01); *C12N 9/0002* (2013.01); *G01N 33/564* (2013.01); *G01N 33/6896* (2013.01); *C07K 2317/21* (2013.01); *C07K 2317/24* (2013.01); *C07K 2317/34* (2013.01); *C07K 2317/92* (2013.01); *G01N 2333/901* (2013.01); *G01N 2800/2821* (2013.01)

(58) Field of Classification Search
None
See application file for complete search history.

(56) References Cited

U.S. PATENT DOCUMENTS

| 4,816,567 | A | 3/1989 | Cabilly |
| 5,500,362 | A | 3/1996 | Robinson |
| 5,591,828 | A | 1/1997 | Bosslet |
| 5,624,821 | A | 4/1997 | Winter |
| 5,648,260 | A | 7/1997 | Winter |
| 5,750,373 | A | 5/1998 | Garrard |
| 5,821,337 | A | 10/1998 | Carter |
| 6,194,551 | B1 | 2/2001 | Idusogie |
| 6,326,193 | B1 | 12/2001 | Liu |
| 6,602,684 | B1 | 8/2003 | Umana et al. |
| 6,737,056 | B1 | 5/2004 | Presta |
| 6,982,321 | B2 | 1/2006 | Winter |
| 7,087,409 | B2 | 8/2006 | Barbas, III |
| 7,332,581 | B2 | 2/2008 | Presta |
| 7,371,826 | B2 | 5/2008 | Presta |
| 7,527,791 | B2 | 5/2009 | Adams |
| 2002/0164328 | A1 | 11/2002 | Shinkawa et al. |
| 2003/0115614 | A1 | 6/2003 | Kanda et al. |
| 2003/0157108 | A1 | 8/2003 | Presta |
| 2003/0165496 | A1* | 9/2003 | Basi ............. A61P 3/10 435/328 |
| 2004/0093621 | A1 | 5/2004 | Shitara et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0132140 | A1 | 7/2004 | Satoh et al. |
| 2004/0146512 | A1 | 7/2004 | Rosenthal |
| 2005/0014934 | A1 | 1/2005 | Hinton et al. |
| 2005/0079574 | A1 | 4/2005 | Bond |
| 2005/0119455 | A1 | 6/2005 | Fuh et al. |
| 2005/0123546 | A1 | 6/2005 | Umana et al. |
| 2005/0266000 | A1 | 12/2005 | Bond et al. |
| 2007/0105092 | A1 | 5/2007 | Paul et al. |
| 2007/0117126 | A1 | 5/2007 | Sidhu et al. |
| 2007/0160598 | A1 | 7/2007 | Dennis et al. |
| 2007/0237764 | A1 | 10/2007 | Birtalan et al. |

(Continued)

FOREIGN PATENT DOCUMENTS

EP    0404097 A2    10/1991
WO    199301161 A1    1/1993
(Continued)

OTHER PUBLICATIONS

Abhinandan, K.R. et al. (Aug. 2008, e-pub. Jul. 9, 2008). "Analysis and Improvements To Kabat and Structurally Correct Numbering Of Antibody Variable Domain," Molecular Immunology 45(14):3832-3839.

Adolf-Bryfogle, J. et al. (2015, e-pub. Nov. 11, 2014). "PylgClassify: A Database of Antibody CDR Structural Classifications," Nucleic Acids Res. 43:D432-D438.

Al-Lazikani, B. et al. (1997). "Standard Conformations for the Canonical Structures of Immunoglobulins," J. Mol. Biol. 273:927-948.

Almagro, J. et al. (Jan. 1, 2008). "Humanization of Antibodies," Frontiers in Bioscience 13:1619-1633.

Baca, M. et al. (Apr. 18, 1997). "Antibody Humanization Using Monovalent Phage Display," J. Biol. Chem. 272 (16):10678-10684.

(Continued)

*Primary Examiner* — Daniel E Kolker
*Assistant Examiner* — James Ryland Melchior
(74) *Attorney, Agent, or Firm* — Morrison & Foerster LLP

(57) ABSTRACT

The present application provides methods, compositions and kits for determining SHD catabody levels in a biological sample, and for treating or preventing a protein aggregation disease (PAD) in an individual. Also provided are catabodies specifically recognizing amyloid beta (Aβ) peptides and methods of use thereof.

5 Claims, 7 Drawing Sheets
Specification includes a Sequence Listing.

(56) References Cited

U.S. PATENT DOCUMENTS

| | | | |
|---|---|---|---|
| 2007/0292410 | A1 | 12/2007 | Cashman |
| 2007/0292936 | A1 | 12/2007 | Barthelemy et al. |
| 2008/0292625 | A1* | 11/2008 | Schroeter ............... A61P 43/00 530/389.1 |
| 2009/0002360 | A1 | 1/2009 | Chen et al. |
| 2009/0297534 | A1 | 12/2009 | Paul et al. |
| 2010/0018361 | A1 | 1/2010 | Chervenak et al. |
| 2010/0202968 | A1 | 8/2010 | Nitsch |
| 2013/0017209 | A1 | 1/2013 | Park et al. |
| 2016/0168235 | A1 | 6/2016 | Paul et al. |
| 2017/0089929 | A1 | 3/2017 | Chakrabartty et al. |
| 2023/0258656 | A1 | 8/2023 | Liu |

FOREIGN PATENT DOCUMENTS

| | | | |
|---|---|---|---|
| WO | 199429351 | A2 | 12/1994 |
| WO | 199429351 | A3 | 2/1995 |
| WO | 199704801 | A1 | 2/1997 |
| WO | 1997030087 | A1 | 8/1997 |
| WO | 1998058964 | A1 | 12/1998 |
| WO | 1999022764 | A1 | 5/1999 |
| WO | 199951642 | A1 | 10/1999 |
| WO | 200042072 | A2 | 7/2000 |
| WO | 200061739 | A1 | 10/2000 |
| WO | 200042072 | A3 | 11/2000 |
| WO | 2001029058 | A1 | 4/2001 |
| WO | 2001029246 | A1 | 4/2001 |
| WO | 200196584 | A2 | 12/2001 |
| WO | 200231140 | A1 | 4/2002 |
| WO | 2002088306 | A2 | 11/2002 |
| WO | 200196584 | A3 | 1/2003 |
| WO | 2003011878 | A2 | 2/2003 |
| WO | 2003084570 | A1 | 10/2003 |
| WO | 2003085107 | A1 | 10/2003 |
| WO | 2003085119 | A1 | 10/2003 |
| WO | 2003011878 | A3 | 11/2003 |
| WO | 2004056312 | A2 | 7/2004 |
| WO | 2005035586 | A1 | 4/2005 |
| WO | 2005035778 | A1 | 4/2005 |
| WO | 2004056312 | A3 | 5/2005 |
| WO | 2005053742 | A1 | 6/2005 |
| WO | 2005100402 | A1 | 10/2005 |
| WO | 2006029879 | A2 | 3/2006 |
| WO | 2006029879 | A3 | 9/2006 |
| WO | 2007088823 | A1 | 8/2007 |
| WO | 2008077546 | A1 | 7/2008 |
| WO | 2009052439 | A2 | 4/2009 |

OTHER PUBLICATIONS

Britschgi, M. et al. (Jul. 21, 2009). "Neuroprotective Natural Antibodies To Assemblies of Amyloidogenic Peptides Decrease With Normal Aging and Advancing Alzheimer's Disease," Proc. Natl. Acad. Sci. USA, 106:12145-12150.

Brüggemann, M. et al. (Nov. 1, 1987). "Comparison of the Effector Functions of Human Immunoglobulins Using a Matched Set of Chimeric Antibodies," J. Exp. Med. 166:1351-1361.

Burton, D.R. (1985). "Immunoglobulin G: Functional Sites," Molec. Immunol. 22(3):161-206.

Capel, P.J. et al. (Feb. 1994). "Heterogeneity of Human IgG Fc receptors," Immunomethods 4(1):25-34.

Carter, P. et al. (May 1992). "Humanization of an Anti-p185HER2 Antibody for Human Cancer Therapy," Proc. Natl. Acad. Sci. USA 89:4285-4289.

Chothia, C. et al. (1989). "Conformations of Immunoglobulin Hypervariable Regions," Nature 342(6252): 877-883.

Chothia, C. et al. (Aug. 20, 1987). "Canonical Structures for the Hypervariable Regions of Immunoglobulins," J. Mol. Biol. 196(4):901-917.

Chothia, C. et al. (Dec. 5, 1985). "Domain Association In Immunoglobulin Molecules. The Packing Of Variable Domains," J. Mol. Biol. 186(3):651-663.

Clackson, T. et al. (Aug. 15, 1991). "Making Antibody Fragments Using Phage Display Libraries," Nature 352:624-628.

Clynes, R. et al. (Jan. 1998). "Fc Receptors are Required in Passive and Active Immunity to Melanoma," Proc. Natl. Acad. Sci. USA 95:652-656.

Cragg, M.S. et al. (Apr. 1, 2004). "Antibody Specificity Controls In Vivo Effector Mechanisms Of Anti-CD20 Reagents," Blood 103(7):2738-2743.

Cragg, M.S. et al. (Feb. 1, 2003). "Complement-Mediated Lysis By Anti-CD20 Mab Correlates With Segregation Into Lipid Rafts," Blood 101(3):1045-1052.

Cunningham, B.C. et al. (Jun. 2, 1989). "High-Resolution Epitope Mapping of hGH-Receptor Interactions by Alanine-Scanning Mutagenesis," Science 244:1081-1085.

Daeron, M. (1997). "Fc Receptor Biology," Annu. Rev. Immunol. 15:203-234.

Dall'Acqua, W.F. et al. (2005). "Antibody Humanization by Framework Shuffling," Methods 36:43-60.

De Haas, M. et al. (Oct. 1995). "Fc Gamma receptors of Phagocytes," J. Lab. Clin. Med. 126:330-341.

Duncan, A.R. et al. (Apr. 21, 1988). "The Binding Site for C1q on IgG," Nature 322:738-740.

Edgar, R.C. (2004, e-pub. Mar. 19, 2004). "MUSCLE: Multiple Sequence Alignment With High Accuracy And High Throughput," Nucleic Acids Research 32(5):1792-1797.

Edgar, R.C. (Aug. 19, 2004). "MUSCLE: A Multiple Sequence Alignment Method With Reduced Time And Space Complexity," BMC Bioinformatics 5(113):1-19.

Ehrenmann, F. et al. (Jan. 2010, e-pub. Nov. 9, 2009). "IMGT/3Dstructure-DB and IMGT/DomainGapAlign: A Database and a Tool For Immunoglobulins or Antibodies, T Cell Receptors, MHC, IgSF and MhcSF," Nucleic Acids Res. 38:D301-D307.

Endo, Y. et al. (2003). "High-Throughput, Genome-Scale Protein Production Method Based On The Wheat Germ Cell-Free Expression System," Biotechnol. Adv. 21:695-713.

Fellouse, F.A. et al. (Aug. 24, 2004). "Synthetic Antibodies From a Four-Amino-Acid Code: A Dominant Role for Tyrosine in Antigen Recognition," Proc. Natl. Acad. Sci. USA 101(34):12467-12472.

Gao, Q.-S. et al. (1995). "Site-Directed Mutagenesis of Proteolytic Antibody Light Chain," J. Mol. Biol. 253(5):658-664.

Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.

Ghetie, V. et al. (2000). "Multiple Roles For The Major Histocompatibility Complex Class I-Related Receptor FCRN," Annu. Rev. Immunol. 18:739-766.

Griffiths, A.D. et al. (1993). "Human Anti-Self Antibodies With High Specificity From Phage Display Libraries," EMBO J. 12(2):725-734.

Guyer, R.L. et al. (Aug. 1976). "Immunoglobulin Binding By Mouse Intestinal Epithelial Cell Receptors," J. Immunol. 117(2):587-593.

Hellstrom, I. et al. (Mar. 1985). "Strong Antitumor Activities of IgG3 Antibodies to a Human Melanoma-associated Ganglioside," Proc. Natl. Acad. Sci. USA 82:1499-1502.

Hellstrom, I. et al. (Sep. 1986). "Antitumor Effects of L6, an IgG2a Antibody That Reacts With Most Human Carcinomas," Proc. Natl. Acad. Sci. USA 83:7059-7063.

Holliger, P. et al. (Jul. 1993). "Diabodies: Small Bivalent and Bispecific Antibody Fragments," Proc. Natl. Acad. Sci. USA 90:6444-6448.

Honegger, A. et al. (Jun. 8, 2001). "Yet Another Numbering Scheme For Immunoglobulin Variable Domains: An Automatic Modeling And Analysis Tool," J. Mol. Biol. 309:657-670.

Hoogenboom, H.R. et al. (2001). "Overview of Antibody Phage-Display Technology and Its Applications," Chapter 1 in Methods in Molecular Biology, O'Brien et al. ed., Humana Press, Totowa, NJ, 178:1-37.

Hoogenboom, H.R. et al. (Sep. 20, 1992). "By-Passing Immunisation Human Antibodies From Synthetic Repertoires Of Germline VH Gene Segments Rearranged In Vitro," J. Mol. Biol. 227(2):381-388.

(56) References Cited

OTHER PUBLICATIONS

Idusogie, E.E. et al. (2000). "Mapping of the C1q Binding Site on Rituxan, a Chimeric Antibody With a Human IgG1 Fc," J. Immunol. 164:4178-4184.

International Preliminary Report on Patentability, issued Feb. 23, for PCT Application No. PCT/US2019/046903, filed Aug. 16, 2019, 6 pages.

International Search Report and Written Opinion, mailed Nov. 14, 2019 for PCT Application No. PCT/US2019/046903, filed Aug. 16, 2019, 10 pages.

Jones, P. et al. (May 29, 1986). "Replacing The Complementarity-Determining Regions In A Human Antibody With Those From A Mouse," Nature 321:522-525.

Kabat, E.A. et al. (1991). Sequences of Proteins of Immunological Interest, 5th Ed. Public Health Service, National Institutes of Health, Bethesda MD., Table of Contents, 21 pages.

Kabat, E.A. et al. (Oct. 10, 1977). "Unusual Distributions Of Amino Acids In Complementarity-Determining (Hypervariable) Segments Of Heavy And Light Chains Of Immunoglobulins And Their Possible Roles In Specificity Of Antibody-Combining Sites," J. Biol. Chem. 252(19):6609-6616.

Kanda, Y. et al. (Jul. 5, 2006, e-pub. Apr. 11, 2006). "Comparison of Cell Line for Stable Production of Fucose-Negative Antibodies with Enhanced ADCC," Biotechnol. Bioeng. 94(4):680-688.

Kashmiri, S.V. et al. (2005). "SDR grafting—A New Approach to Antibody Humanization," Methods 36:25-34.

Kellner, A. et al. (2009). "Autoantibodies Against Beta-Amyloid Are Common In Alzheimer's Disease and Help Control Plaque Burden," Ann. Neurol. 65:24-31.

Kim, J-K. et al. (1994). "Localization of the Site of the Murine IgG1 Molecule That is Involved in Binding to the Murine Intestinal Fc Receptor," Eur. J. Immunol. 24:2429-2434.

Klimka, A. et al. (2000). "Human Anti-CD30 Recombinant Antibodies by Guided Phage Antibody Selection Using Cell Panning," Br. J. Cancer 83(2):252-260.

Lee, C.V. et al. (2004). "Bivalent Antibody Phage Display Mimics Natural Immunoglobulin," Journal of Immunological Methods 284:119-132.

Lee, C.V. et al. (2004). "High-Affinity Human Antibodies From Phage-Displayed Synthetic Fab Libraries With A Single Framework Scaffold," J. Mol. Biol. 340:1073-1093.

Lefranc, M.P. et al. (Jan. 2003). "IMGT Unique Numbering For Immunoglobulin And T Cell Receptor Variable Domains And Ig Superfamily V-Like Domains," Dev. Comp. Immunol. 27(1):55-77.

MacCallum, R.M. et al. (1996). "Antibody-Antigen Interactions: Contact Analysis and Binding Site Topography," J. Mol. Biol. 262:732-745.

Marks, J.D. et al. (1991). "By-Passing Immunization. Human Antibodies From V-Gene Libraries Displayed on Phage," J. Mol. Biol. 222:581-597.

Marks, J.D. et al. (2004) "Selection of Human Antibodies from Phage Display Libraries," Chapter 8 in Methods in Molecular Biology, LO, B.K.C. (ed.), Humana Press Inc., Totowa, NJ, 248:161-176, 29 pages.

McCafferty, J. et al. (Dec. 6, 1990). "Phage Antibodies: Filamentous Phage Displaying Antibody Variable Domains," Nature 348:552-554.

Meretoja, V.V. et al. (2017). "Chapter 9—Hydrolysis and Dissolution of Amyloids by Catabodies," in Natural Antibodies: Methods and Protocols Methods in Molecular Biology 1643:111-134.

Mordenti, J. et al. (1989). "The Use of Interspecies Scaling in Toxicokinetics," Chapter 4 in Toxicokinetics and New Drug Development, Yacobi A. ed. et al.; Pergamon Press, New York, pp. 42-96.

Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.

Mruthinti, S. et al. (2004). "Autoimmunity in Alzheimer's Disease: Increased Levels Of Circulating IgGs Binding Aβ and RAGE Peptides," Neurobiol. Aging 25:1023-1032.

Nishiyama, Y. et la. (Jun. 20, 2014). "Metal-Dependent Amyloid β-Degrading Catalytic Antibody Construct," J. Biotechnol. 180:17-22, 16 pages.

Okazaki, A. et al. (Mar. 5, 2004). "Fucose Depletion From Human IgG1 Oligosaccharide Enhances Binding Enthalpy And Association Rate Between IgG1 and FcγRIIIa," J. Mol. Biol. 336(5):1239-1249.

Osbourn, J. et al. (2005). "From Rodent Regents to Human Therapeutics Using Antibody Guided Selection," Methods 36:61-68.

Padlan, E.D. (1991). "A Possible Procedure for Reducing the Immunogenicity of Antibody Variable Domains While Preserving Their Ligand-Binding Properties," Mol. Immunol. 28(4/5):489-498.

Petkova, S.B. et al. (Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18 (12):1759-1769.

Planque, S.A. et al. (Apr. 17, 2015). "Specific Amyloid β Clearance by a Catalytic Antibody Construct," Journal of Biological Chemistry 290(16):10229-10241.

Planque, S.A. et al. (May 9, 2014). "Physiological IgM Class Catalytic Antibodies Selective for Transthyretin AMyloid," J. Biol. Chem. 289(19):13243-13258.

Plückthun, A. (1994). "Antibodies from *Escherichia coli*," in Chapter 11 The Pharmacology of Monoclonal Antibodies, vol. 113, Rosenburg and Moore eds., Springer-Verlag, New York, pp. 269-315, 48 pages.

Presta, L.G. (1992). "Antibody Engineering," Current Opinion in Structural Biology 2:593-596.

Presta, L.G. et al. (Sep. 1, 1993). "Humanization of an Antibody Directed Against IgE," J. Immunol. 151 (5):2623-2632.

Queen, C. et al. (Dec. 1989). "A Humanized Antibody That Binds to the Interleukin 2 Receptor," Proc. Natl Acad. Sci. USA 86:10029-10033.

Ravetch, J.V. et al. (1991). "Fc Receptors," Annu. Rev. Immunol. 9:457-492.

Remington's Pharmaceutical Sciences. (1980). 16th edition, Osol, A. Ed, pp. 1-2, (Table of Contents Only).

Riechmann, L. et al. (Mar. 24, 1988). "Reshaping Human Antibodies for Therapy," Nature 332:323-329.

Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.

Rosok, M.J. et al. (Sep. 13, 1996). "A Combinatorial Library Strategy for the Rapid Humanization of Anticarcinoma BR96 Fab," J. Biol. Chem. 271(37):22611-22618.

Running Deer, J. et al. (May-Jun. 2004, e-pub. Mar. 10, 2004). "High-Level Expression Of Proteins In Mammalian Cells Using Transcription Regulatory Sequences From The Chinese Hamster EF-1Alpha Gene," Biotechnol. Prog. 20(3):880-889.

Sambrook, J. et al. (2001). Molecular Cloning: A Laboratory Manual Cold Spring Harbor Laboratory Press, Cold Spring Harbor, N.Y., 3rd ed., 1 page, Table of Contents.

Shields, R.L. et al. (Mar. 2, 2001). "High Resolution Mapping of the Binding Site on Human IgG1 for FcγRI, FcγRII. FcγRIII, and FcRn and Design of IgG1 Variants With Improved Binding to the FcγR," J. Biol.Chem. 276(9):6591-6604.

Shoji-Hosaka, E. et al. (2006). "Enhanced Fc-Dependent Cellular Cytotoxicity of Fc Fusion Proteins Derived from TNF Receptor II and LFA-3 by Fucose Removal from Asn-Linked Oligosaccharides," J. Biochem. 140(6):777-783.

Sidhu, S.S. et al. (2004). "Phage-Displayed Antibody Libraries Synthetic Heavy Chain Complementarity Determining Regions," J. Mol. Biol. 338(2):299-310.

Sims, M.J. et al. (Aug. 15, 1993). "A Humanized CD18 Antibody Can Block Function Without Cell Destruction," J. Immunol. 151(4):2296-2308.

Sitaraman, K. et al. (2009). "High-Throughput Protein Expression Using Cell-Free System," Methods Mol. Biol. 498:229-244.

Spirin, A.S. (Oct. 2004). "High-Throughput Cell-Free Systems For Synthesis Of Functionally Active Proteins," Trends Biotechnol. 22(10):538-545.

Taguchi, H. et al. (May 2008). "Catalytic Antibodies To Amyloid Beta Peptide In Defense Against Alzheimer Disease," Autoimmun. Rev. 7(5):391-397, 9 pages.

(56) References Cited

OTHER PUBLICATIONS

Ui-Tel, K. et al. (2000). "Sensitive Assay of RNA Interference in *Drosophila* and Chinese Hamster Cultured Cells Using Firefly Luciferase Gene As Target," FEBS Letters 479:79-82.

Weksler, M.E. et al. (Jul. 2002). "Patients With Alzheimer Disease Have Lower Levels Of Serum Anti-Amyloid Peptide Antibodies Than Healthy Elderly Individuals," Exp Gerontol. 37(7):943-948.

Winter, G. et al. (1994). "Making Antibodies by Phage Display Technology," Ann. Rev. Immunol. 12:433-455.

Wright, A. et al. (Jan. 1997). "Effect of Glycosylation on Antibody Function: Implications for Genetics Engineering," Trends Biotechnol. 15:26-32.

Yamane-Ohnuki, N et al. (Sep. 5, 2004, e-pub. Aug. 6, 2004). "Establishment of FUT8 Knockout Chinese hamster Ovary Cells: An Ideal Host Cell Line for Producing Completely Defucosylated Antibodies With Enhances Antibody-Dependent Cellular Cytotoxicity," Biotech. Bioeng. 87(5):614-622.

Feinberg, H. et al. (Jun. 2, 2014). "Crystal Structure Reveals Conservation of Amyloid-β Conformation Recognized by 3D6 Following Humanization to Bapineuzumab," Alz. Res. Therapy 6:31, 13 pages.

Gao, Q.S. et al. (Dec. 23, 1994). "Molecular Cloning of a Proteolytic Antibody Light Chain," Journal of Biological Chemistry 269(61):32389-32393.

Hatiuchi, K. et al. (May 1, 2003). "Endopeptidase Character of Monoclonal Antibody i41-7 Subunits," Immunology Letters 86(3):249-257.

Li, Y.- Z. et al. (Dec. 25, 2012). "Application of SAMP8 in Study of Alzheimer's Disease in Rapidly Senescent Mice," A Chinese Journal of Rehabilitation Theory and Practice 18(12):1119-1122. English Abstract, 4 pages.

\* cited by examiner

FIG. 4
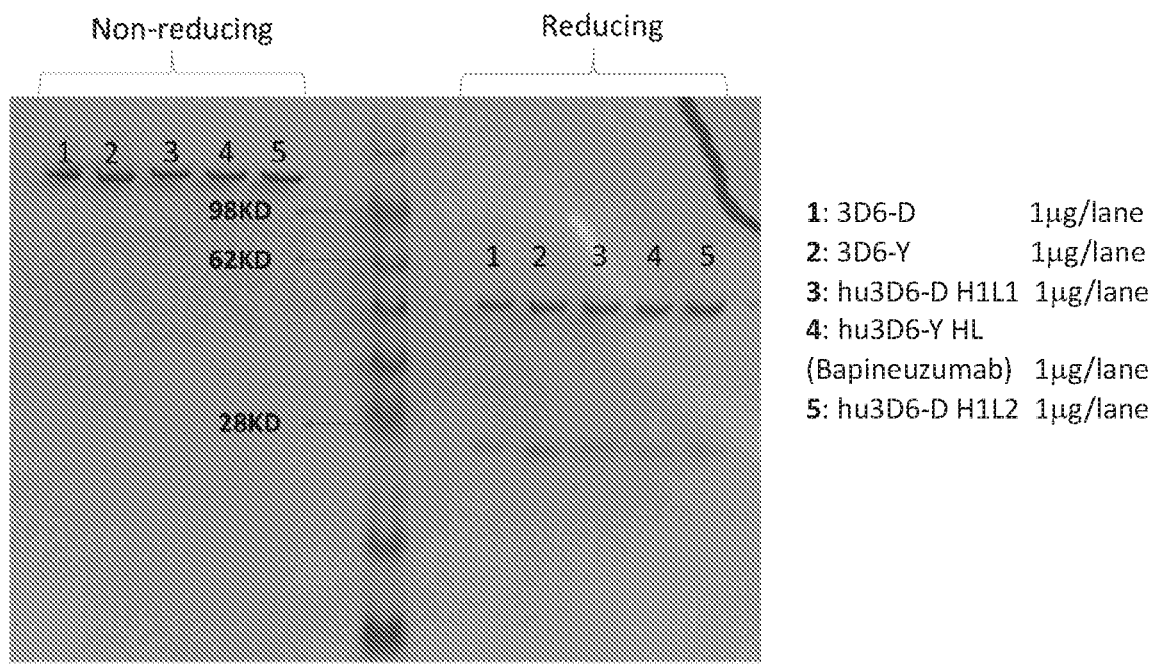
1: 3D6-D       1μg/lane
2: 3D6-Y       1μg/lane
3: hu3D6-D H1L1  1μg/lane
4: hu3D6-Y HL
(Bapineuzumab)  1μg/lane
5: hu3D6-D H1L2  1μg/lane
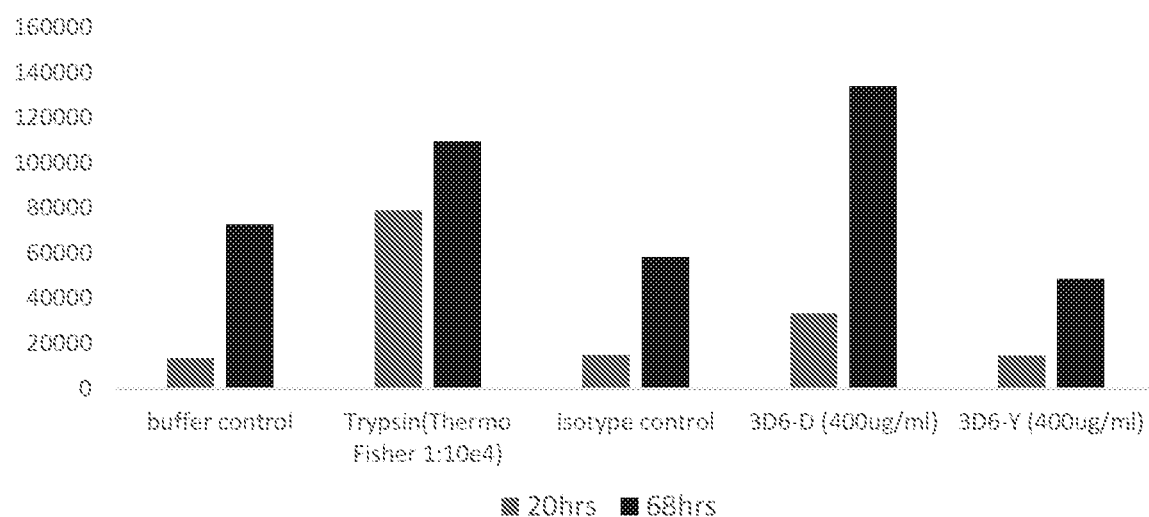
FIG. 5 humanized 3D6 binding with A Beta

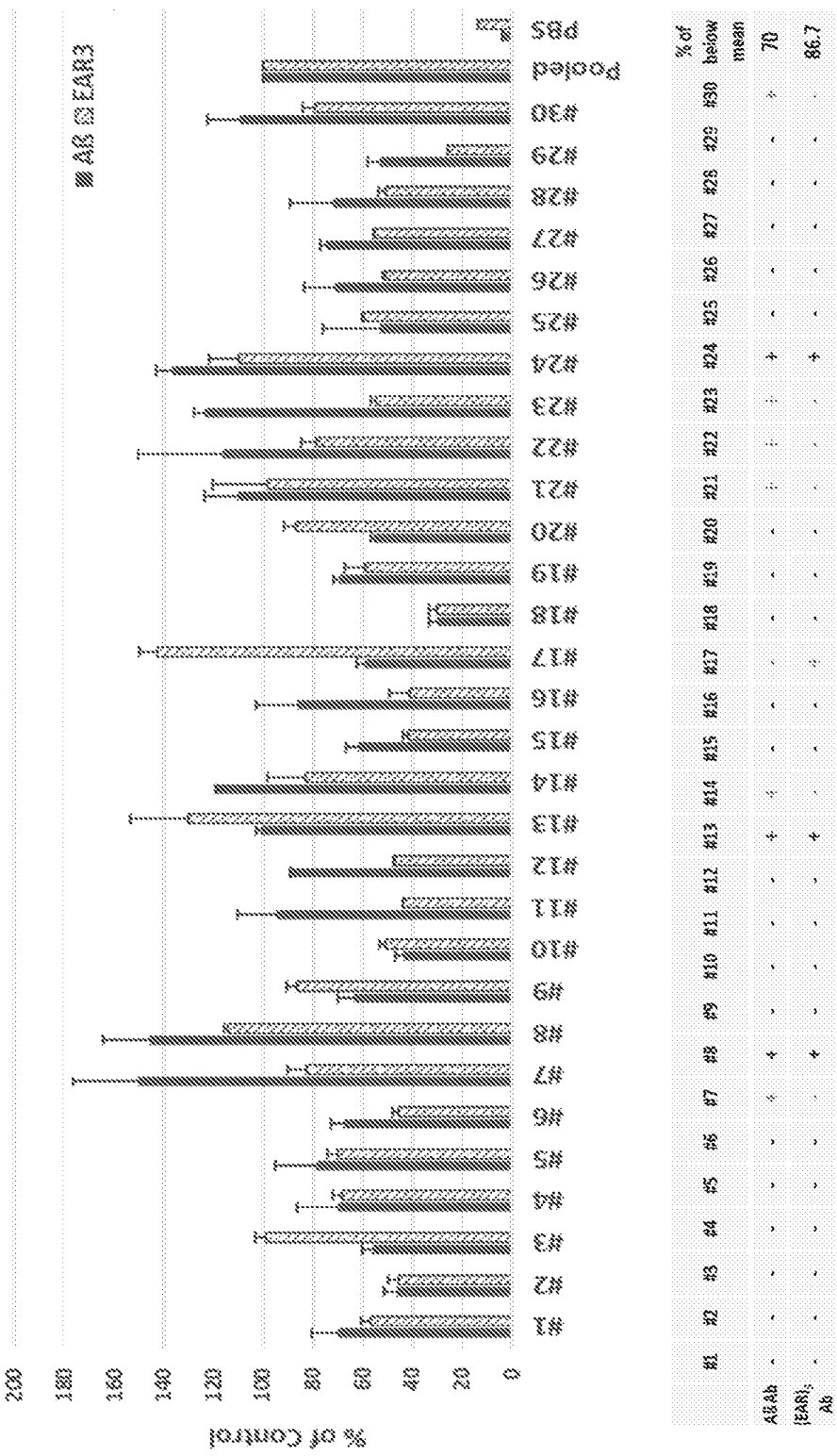

FIG. 9A

|   | 1 | 2 | 3 | 4 | 5 | 6 | 7 | 8 | 9 | 10 | 11 | 12 |
|---|---|---|---|---|---|---|---|---|---|----|----|----|
| A | N1 | N9 | N17 | N25 | 1 | N1 | N9 | N17 | 25 | 1 |  |  |
| B | N2 | N10 | N18 | O1 | 2 | N2 | N10 | N18 | O1 | 2 |  |  |
| C | N3 | N11 | N19 | O2 | 3 | N3 | N11 | N19 | O2 | 3 |  |  |
| D | N4 | N12 | N20 | O3 | 4 | N4 | N12 | N20 | O3 | 4 |  |  |
| E | N5 | N13 | N21 | O4 | 5 | N5 | N13 | N21 | O4 | 5 |  |  |
| F | N6 | N14 | N22 | O5 | 6 | N6 | N14 | N22 | O5 | 6 |  |  |
| G | N7 | N15 | N23 | Pool | 7 | N7 | N15 | N23 | Pool | 7 |  |  |
| H | N8 | N16 | N24 | PBS | 8 | N8 | N16 | N24 | PBS | 8 |  |  |

Primary      Duplicate      Blank 1-25 (lanes 1-3 + A4, lanes 6-8 + A9): new AD serum samples
1-5 (lane 4, lane9): old AD serum samples
Pool: pooled serum sample from healthy human
1-8 (lane5, lane10): healthy human serum samples

FIG. 9B

|   | 1 | 2 | 3 | 4 | 5 | 6 | 7 | 8 | 9 | 10 | 11 | 12 |
|---|---|---|---|---|---|---|---|---|---|----|----|----|
| A | 9286 | 8160 | 7350 | 6011 | 11753 | 7519 | 7092 | 6833 | 6737 | 15593 | 9 | 8 |
| B | 5997 | 5525 | 3867 | 8327 | 8015 | 5101 | 5023 | 3348 | 8750 | 10127 | 7 | 10 |
| C | 6420 | 12688 | 8530 | 8800 | 6770 | 7059 | 9951 | 8179 | 9197 | 6458 | 10 | 7 |
| D | 9779 | 10665 | 6778 | 8104 | 8892 | 6936 | 10544 | 6581 | 9074 | 11856 | 12 | 10 |
| E | 10841 | 12266 | 14327 | 6081 | 11118 | 8097 | 12039 | 12138 | 6570 | 12006 | 11 | 10 |
| F | 8532 | 14267 | 11081 | 12343 | 6992 | 7720 | 14275 | 16807 | 13831 | 9256 | 8 | 15 |
| G | 20232 | 6974 | 15196 | 14274 | 6292 | 15784 | 7794 | 14426 | 15050 | 6919 | 4 | 9 |
| H | 19067 | 9029 | 15822 | 417 | 11088 | 15940 | 11736 | 16927 | 387 | 12545 | 6 | 8 |

FIG. 9C

|   | 1 | 2 | 3 | 4 | 5 | 6 | 7 | 8 | 9 | 10 | 11 | 12 |
|---|---|---|---|---|---|---|---|---|---|----|----|----|
| A | 35776 | 53901 | 89004 | 39028 | 55688 | 32711 | 50382 | 82550 | 33009 | 55823 | 0 | -1 |
| B | 29302 | 31641 | 19445 | 32800 | 64531 | 25609 | 29673 | 16858 | 28662 | 65251 | 2 | -2 |
| C | 61349 | 26369 | 38987 | 35746 | 21249 | 57690 | 26162 | 32357 | 30529 | 20749 | 1 | 1 |
| D | 42875 | 28517 | 54333 | 32770 | 44931 | 39348 | 27799 | 50259 | 28509 | 47002 | 1 | 3 |
| E | 44084 | 88439 | 68478 | 16034 | 76852 | 40230 | 68557 | 49798 | 14612 | 76957 | -1 | 1 |
| F | 28578 | 56464 | 49953 | 49637 | 22578 | 25960 | 43564 | 45129 | 45709 | 18169 | -1 | 3 |
| G | 53112 | 25912 | 33975 | 66919 | 46255 | 46549 | 24110 | 32131 | 56263 | 46078 | -3 | -1 |
| H | 68264 | 28254 | 71251 | 8103 | 104107 | 69622 | 21390 | 60776 | 8452 | 92201 | -4 | 2 |

US 12,259,395 B2

SEQUENCE LISTING

```
<160> NUMBER OF SEQ ID NOS: 25

<210> SEQ ID NO 1
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Conjugated to 7-amino-4-methylcoumarin

<400> SEQUENCE: 1

Glu Ala Arg
1

<210> SEQ ID NO 2
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(3)
<223> OTHER INFORMATION: Can be present in repeats of 1-30

<400> SEQUENCE: 2

Glu Ala Arg
1

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Glu Ala Arg Glu Ala Arg Glu Ala Arg
1               5

<210> SEQ ID NO 4
<211> LENGTH: 119
<212> TYPE: PRT
<213> ORGANISM: Artificial Sequence
<220> FEATURE:
<223> OTHER INFORMATION: Synthetic Construct

<400> SEQUENCE: 4

Glu Val Lys Leu Val Glu Ser Gly Gly Gly Leu Val Lys Pro Gly Ala
1               5                   10                  15
```

```
Ser Leu Lys Leu Ser Cys Ala Ala Ser Gly Phe Thr Phe Ser Asn Tyr
            20                  25                  30

Gly Met Ser Trp Val Arg Gln Asn Ser Asp Lys Arg Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Glu Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Val Arg Tyr Asp His Tyr Ser Gly Ser Ser Asp Tyr Trp Gly Gln Gly
            100                 105                 110

Thr Thr Val Thr Val Ser Ser
            115
```

```
<210> SEQ ID NO 5
<211> LENGTH: 113
<212> TYPE: PRT
<213> ORGANISM: Artificial Sequence
<220> FEATURE:
<223> OTHER INFORMATION: Synthetic Construct

<400> SEQUENCE: 5

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Ile Glu Ala Glu Asp Leu Gly Leu Tyr Tyr Cys Trp Gln Gly
                85                  90                  95

Thr His Phe Pro Arg Thr Phe Gly Gly Gly Thr Lys Leu Glu Ile Lys
            100                 105                 110

Arg
```

```
<210> SEQ ID NO 6
<211> LENGTH: 119
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Asp Lys Arg Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Asp Asn Ala Lys Asn Thr Leu Tyr
65                  70                  75                  80
```

```
Leu Gln Met Asn Ser Leu Arg Ala Glu Asp Thr Ala Leu Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser
        115

<210> SEQ ID NO 7
<211> LENGTH: 113
<212> TYPE: PRT
<213> ORGANISM: Artificial Sequence
<220> FEATURE:
<223> OTHER INFORMATION: Synthetic Construct

<400> SEQUENCE: 7

Asp Val Val Met Thr Gln Ser Pro Leu Ser Leu Pro Val Thr Leu Gly
1               5                   10                  15

Glu Pro Ala Ser Ile Ser Cys Lys Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

Arg

<210> SEQ ID NO 8
<211> LENGTH: 113
<212> TYPE: PRT
<213> ORGANISM: Artificial Sequence
<220> FEATURE:
<223> OTHER INFORMATION: Synthetic Construct

<400> SEQUENCE: 8

Asp Val Val Met Thr Gln Ser Pro Leu Ser Leu Pro Val Thr Leu Gly
1               5                   10                  15

Glu Pro Ala Ser Ile Ser Cys Lys Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Ile Glu Ala Glu Asp Val Gly Leu Tyr Tyr Cys Trp Gln Gly
                85                  90                  95

Thr His Phe Pro Arg Thr Phe Gly Gly Gly Thr Lys Leu Glu Ile Lys
            100                 105                 110

Arg

<210> SEQ ID NO 9
<211> LENGTH: 5
<212> TYPE: PRT
```

```
<213> ORGANISM: Artificial Sequence
<220> FEATURE:
<223> OTHER INFORMATION: Synthetic Construct

<400> SEQUENCE: 9

Asn Tyr Gly Met Ser
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

Ser Ile Arg Ser Gly Gly Gly Arg Thr Tyr Tyr Ser Asp Asn Val Lys
1               5                   10                  15

Gly

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Tyr Asp His Tyr Ser Gly Ser Ser Asp Tyr
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Synthetic Construct

<400> SEQUENCE: 12

Lys Ser Ser Gln Ser Leu Leu Asp Ser Asp Gly Lys Thr Tyr Leu Asn
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct

<400> SEQUENCE: 13

Leu Val Ser Lys Leu Asp Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct

<400> SEQUENCE: 14

Trp Gln Gly Thr His Phe Pro Arg Thr
1               5

<210> SEQ ID NO 15
<211> LENGTH: 330
```

<212> TYPE: PRT
<213> ORGANISM: Artificial Sequence
<220> FEATURE:
<223> OTHER INFORMATION: Synthetic Construct

<400> SEQUENCE: 15

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 16
<211> LENGTH: 327
<212> TYPE: PRT
<213> ORGANISM: Artificial Sequence
<220> FEATURE:
<223> OTHER INFORMATION: Synthetic Construct

<400> SEQUENCE: 16

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 17
<211> LENGTH: 106
<212> TYPE: PRT
<213> ORGANISM: Artificial Sequence
<220> FEATURE:
<223> OTHER INFORMATION: Synthetic Construct

<400> SEQUENCE: 17

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30
```

```
Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 18
<211> LENGTH: 105
<212> TYPE: PRT
<213> ORGANISM: Artificial Sequence
<220> FEATURE:
<223> OTHER INFORMATION: Synthetic Construct

<400> SEQUENCE: 18

```
Gln Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Gly Ser Pro Val
        35                  40                  45

Lys Ala Gly Val Glu Thr Thr Lys Pro Ser Lys Gln Ser Asn Asn Lys
 50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```

<210> SEQ ID NO 19
<211> LENGTH: 119
<212> TYPE: PRT
<213> ORGANISM: Artificial Sequence
<220> FEATURE:
<223> OTHER INFORMATION: Synthetic Construct

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Ser Asp Lys Arg Leu Glu Trp Val
        35                  40                  45

Ala Ser Ile Arg Ser Gly Gly Gly Arg Thr Tyr Tyr Ser Asp Asn Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser
```

<210> SEQ ID NO 20
<211> LENGTH: 119
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Asn Ser Asp Lys Arg Leu Glu Trp Val
        35                  40                  45

Ala Ser Ile Arg Ser Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Val Arg Tyr Asp His Tyr Ser Gly Ser Ser Tyr Trp Gly Gln Gly
            100                 105                 110

Thr Leu Val Thr Val Ser Ser
            115

<210> SEQ ID NO 21
<211> LENGTH: 113
<212> TYPE: PRT
<213> ORGANISM: Artificial Sequence
<220> FEATURE:
<223> OTHER INFORMATION: Synthetic Construct

<400> SEQUENCE: 21

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gly Gly Thr Lys Val Glu Ile Lys
            100                 105                 110

Arg

<210> SEQ ID NO 22
<211> LENGTH: 113
<212> TYPE: PRT
<213> ORGANISM: Artificial Sequence
<220> FEATURE:
<223> OTHER INFORMATION: Synthetic Construct

<400> SEQUENCE: 22

-continued

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Ile Glu Ala Glu Asp Val Gly Val Tyr Tyr Cys Trp Gln Gly
                85                  90                  95

Thr His Phe Pro Arg Thr Phe Gly Gly Gly Thr Lys Val Glu Ile Lys
            100                 105                 110

Arg
```

<210> SEQ ID NO 23
<211> LENGTH: 113
<212> TYPE: PRT
<213> ORGANISM: Artificial Sequence
<220> FEATURE:
<223> OTHER INFORMATION: Synthetic Construct

<400> SEQUENCE: 23

```
Tyr Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Ile Glu Ala Glu Asp Leu Gly Leu Tyr Tyr Cys Trp Gln Gly
                85                  90                  95

Thr His Phe Pro Arg Thr Phe Gly Gly Gly Thr Lys Leu Glu Ile Lys
            100                 105                 110

Arg
```

<210> SEQ ID NO 24
<211> LENGTH: 119
<212> TYPE: PRT
<213> ORGANISM: Artificial Sequence
<220> FEATURE:
<223> OTHER INFORMATION: Synthetic Construct

<400> SEQUENCE: 24

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Asp Asn Ala Lys Asn Ser Leu Tyr
```

```
                65                  70                  75                  80
Leu Gln Met Asn Ser Leu Arg Ala Glu Asp Thr Ala Leu Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser
        115

<210> SEQ ID NO 25
<211> LENGTH: 113
<212> TYPE: PRT
<213> ORGANISM: Artificial Sequence
<220> FEATURE:
<223> OTHER INFORMATION: Synthetic Construct

<400> SEQUENCE: 25

Tyr Val Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gln Gly Thr Lys Val Glu Ile Lys
            100                 105                 110

Arg
```

CATABODIES AND METHODS OF USE THEREOF

CROSS REFERENCE TO RELATED APPLICATIONS

This application is a national stage application under 35 U.S.C. § 371 of International Application No. PCT/US2019/046903, filed internationally on Aug. 16, 2019, which claims priority benefit of Provisional Patent Application No. 62/765,150, filed on Aug. 17, 2018, the contents of which are incorporated herein by reference in their entirety.

SUBMISSION OF SEQUENCE LISTING ON ASCII TEXT FILE

The content of the fallowing submission on ASCII text file is incorporated herein by reference in its entirety: a computer readable form (CRF) of the Sequence Listing (file name: 792702000100SEQLIST.TXT, date recorded: Feb. 10, 2021, size: 22 KB).

FIELD OF THE INVENTION

The present application is related to catabodies, methods for determining catabody levels, and methods of treatment using catabodies. In particularly, the present application is related to compositions and use of catabodies specifically recognizing and cleaving amyloid beta (Aβ) peptides.

BACKGROUND OF THE INVENTION

Catabodies are antibodies that specifically bind to target antigens and catalyze chemical transformation of their target antigens. Proteolytic catabodies can hydrolyze and permanently inactivate target peptides. A single catabody molecule can hydrolyze thousands of antigen molecules over its biological lifetime, thereby achieving enhanced potency compared to a stoichiometrically-binding conventional antibody. Naturally-occurring catabodies have been found in normal humans and in patients with autoimmune diseases. Catabodies have also been raised in lab animals immunized against synthetic haptens or screened from antibody libraries using transition-state analogs. However, due to their relatively modest catalytic activity, catabodies have not been widely developed as therapeutic agents.

Protein aggregation is a biological phenomenon in which misfolded proteins aggregate intracellularly or extracellularly. These protein aggregates are often associated with neurodegenerative diseases including Amyotrophic lateral sclerosis (ALS), Alzheimer's disease (AD). Parkinson's disease (PD), prion diseases and other amyloidosis diseases. For example, according to the amyloid hypothesis, soluble and fibrillary amyloid beta (Aβ) peptides aggregates contribute causally to the pathogenesis of AD. The Aβ aggregates activate microglial inflammatory processes, exert direct neurotoxic effects, and disrupt the anatomic architecture of the brain. In order to treat AD, antibody-mediated immunotherapeutics have been applied to induce clearance of existing Aβ amyloids and to inhibit further Aβ aggregation. However, many of these antibody-based therapies have failed in clinical trials, including Bapineuzumab and Solanezumab.

The disclosures of all publications, patents, patent applications and published patent applications referred to herein are hereby incorporated herein by reference in their entirety.

BRIEF SUMMARY OF THE INVENTION

The present application provides compositions and methods for diagnosis (including methods of determining a risk), treatment and prevention of a protein aggregation disease (PAD), such as Alzheimer's disease (AD) in an individual.

One aspect of the present application provides a method for determining the level of one or more SHD catabodies (i.e., catabodies containing a catalytic triad motif of serine, histidine and aspartate, or "SHD motif") in a biological sample, comprising: a) contacting the biological sample with a substrate peptide immobilized on a solid support under conditions that allow formation of a catabody-substrate peptide complex, and b) determining the amount of the catabody-substrate peptide complex, thereby providing the level of one or more SHD catabodies in the biological sample, wherein the substrate peptide comprises the amino acid sequence $(EAR)_n$ (SEQ ID NO: 2), and wherein n is an integer between 1 and 30 (e.g., n is 3). In some embodiments, the biological sample is incubated with the substrate peptide for about 1 hour to about 16 hours, such as any one of about 1 hour to about 3 hours, about 3 hours to about 8 hours, or about 8 hours to about 16 hours.

In some embodiments according to any one of the methods described above, the biological sample is a serum sample. In some embodiments, the serum sample contains at least about 1 μg/mL (e.g., at least about 10 μg/mL, 25 μg/mL, or 100 μg/mL) immunoglobulin (Ig; e.g., human Ig).

In some embodiments according to any one of the methods described above, the amount of the catabody-substrate peptide complex is determined using an antibody that specifically binds to total immunoglobulin (Ig, such as total human Ig). In some embodiments, the antibody specifically binds to total IgM, total IgG, total IgA, and/or total IgE. In some embodiments, the antibody is labeled with an enzyme (e.g., horseradish peroxidase or "HRP") or a fluorescent label (e.g., FITC).

One aspect of the present application provides a method for determining a risk for a PAD in an individual, wherein the PAD is associated with aggregation of a target protein, comprising determining the level of one or more SHD catabodies in a biological sample (e.g., serum sample) of the individual, wherein the individual is determined as having a risk for the PAD if the level of the one or more SHD catabodies is lower than a control SHD catabody level. In some embodiments, the level of one or more SHD catabodies is the level of one or more SHD catabodies that specifically bind to the target protein. In some embodiments, the level of one or more SHD catabodies is the level of total SHD catabodies. In some embodiments, the level of total SHD catabodies is determined by contacting a serum sample of the individual with a substrate peptide immobilized on a solid support under conditions that allow formation of a catabody-substrate peptide complex, and determining the amount of the catabody-substrate peptide complex, wherein the substrate peptide comprises the amino acid sequence (EAR). (SEQ ID NO: 2), and wherein n is an integer between 1 and 30 (e.g., n is 3). In some embodiments, the serum sample contains at least about 1 μg/mL (e.g., at least about 10 μg/mL, 25 μg/mL, or 100 μg/mL) Ig (e.g., human Ig). In some embodiments, the biological sample is incubated with the substrate peptide for about 1 hour to about 16 hours, such as any one of about 1 hour to about 3 hours, about 3 hours to about 8 hours, or about 8 hours to about 16 hours. In some embodiments, the amount of the catabody-substrate peptide complex is determined using an antibody that specifically binds to total Ig (e.g., total human Ig). In some embodiments, the antibody specifically binds to total IgM, total IgG, total IgA, and/or total IgE. In some embodiments, the antibody is labeled with an enzyme (e.g., horseradish peroxidase or "HRP") or a fluorescent label (e.g., FITC).

In some embodiments according to any one of the methods for determining a risk as described above, the method further comprises determining the level of an auto-antibody against the target protein in a biological sample (e.g., serum sample) of the individual, and wherein the individual is determined as having a risk for the PAD if: (i) the level of the one or more SHD catabodies is lower than a control SHD catabody level; and (ii) the level of the auto-antibody against the target protein is lower than a control auto-antibody level. In some embodiments, the level of the auto-antibody is determined by contacting a serum sample of the individual with the target protein under conditions that allow formation of an auto-antibody-target protein complex, and determining the amount of the auto-antibody-target protein complex. In some embodiments, the level of the auto-antibody is determined using an ELISA assay. In some embodiments, the control auto-antibody level is the level of the auto-antibody against the target protein in a healthy individual (e.g., of the same age group). In some embodiments, the control auto-antibody level is the median level of the auto-antibody against the target protein in a population of individuals (e.g., of the same age group).

In some embodiments according to any one of the methods for determining a risk as described above, the method further comprises determining the level of the target protein in a biological sample (e.g., serum sample or cerebrospinal fluid sample) of the individual, and wherein the individual is determined as having a risk for the PAD if: (i) the level of the one or more SHD catabodies is lower than a control SHD catabody level; and (ii) the level of the target protein is higher than a control target protein level. In some embodiments, the level of the target protein is determined by contacting the biological sample of the individual with an antibody against the target protein under conditions that allow formation of an antibody-target protein complex, and determining the amount of the antibody-target protein complex. In some embodiments, the level of the target protein is determined using an ELISA assay. In some embodiments, the control target protein level is the level of the target protein in a healthy individual (e.g., of the same age group). In some embodiments, the control target protein level is the median level of the target protein in a population of individuals (e.g., of the same age group).

In some embodiments according to any one of the methods for determining a risk as described above, the control SHD catabody level is the level of one or more SHD catabodies in a healthy individual (e.g., of the same age group). In some embodiments, the control SHD catabody level is the median level of one or more SHD catabodies in a population of individuals (e.g., of the same age group).

In some embodiments according to any one of the methods for determining a risk as described above, the PAD is Alzheimer's disease, and wherein the target protein is amyloid β (Aβ). In some embodiments, the PAD is Parkinson's disease, and the target protein is α-synuclein. In some embodiments, the PAD is Alzheimer's disease or dementia, and the target protein is Tau. In some embodiments, the PAD is ATTR amyloidosis, and the target protein is transthyretin. In some embodiments, the PAD is AL amyloidosis, and the target protein is immunoglobulin light chain. In some embodiments, the PAD is frontotemporal lobar degeneration (FTLD) or amyotrophic lateral sclerosis (ALS), and the target protein is TDP43. In some embodiments, the PAD is Huntington's disease, and the target protein is Huntingtin. In some embodiments, the PAD is Type II diabetes, and the target protein is IAPP. In some embodiments, the PAD is Amyotrophic Lateral Sclerosis (ALS), and the target protein is SOD1.

One aspect of the present application provides a method of treating or preventing a protein aggregation disease (PAD) in an individual, wherein the PAD is associated with aggregation of a target protein, comprising: a) determining the individual as having a risk for the PAD according to any one of the methods for determining a risk as described above; and b) administering to the individual an effective amount of a therapeutic catabody that specifically binds to the target protein. In some embodiments, the method is repeated at a frequency of no more than about every three months, e.g., about every three months, about every six months, or about every year.

In some embodiments according to any one of the methods of treatment described above, the PAD is Alzheimer's disease and wherein the target protein is amyloid β (Aβ), and wherein the therapeutic catabody comprises a light chain variable region ($V_L$) comprising a light chain complementarity determining region (LC-CDR) 1 comprising the amino acid sequence of SEQ ID NO: 12, an LC-CDR2 comprising the amino acid sequence of SEQ ID NO: 13, and an LC-CDR3 comprising the amino acid sequence of SEQ ID NO: 14, or a variant thereof comprising up to about 5 (e.g., 1, 2, 3, 4, or 5) amino acid substitutions in the LC-CDRs, wherein the amino acid residue at position 1 of the $V_L$ is D, the amino acid residue at position 27A of the $V_L$ is S, and the amino acid residue at position 93 of the $V_L$ is H, and wherein the numbering is according to the EU index of Kabat. In some embodiments, the therapeutic catabody comprises a heavy chain variable region ($V_H$) comprising a heavy chain complementarity determining region (HC-CDR) 1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11, or a variant thereof comprising up to about 5 (e.g., 1, 2, 3, 4, or 5) amino acid substitutions in the HC-CDRs. In some embodiments, the amino acid residue at position 26 of the $V_L$ is S, the amino acid residue at position 27D of the $V_L$ is D, E or H, and/or the amino acid residue at position 28 of the $V_L$ is D or N. and wherein the numbering is according to the EU index of Kabat. In some embodiments, the therapeutic catabody comprises a $V_H$ comprising an amino acid sequence having at least about 85% sequence identity (e.g., at least about any one of 90%, 95%, 97%, 99%, or 100%) to the amino acid sequence of SEQ ID NO: 4, 6, 19 or 20. In some embodiments, the therapeutic catabody comprises a $V_L$ comprising an amino acid sequence having at least about 85% (e.g., at least about any one of 90%, 95%, 97%, 99%, or 100%) sequence identity to the amino acid sequence of SEQ ID NO: 5, 7, 8, 21 or 22. In some embodiments, the therapeutic catabody comprises a $V_H$ comprising an amino acid sequence selected from the amino acid sequences of SEQ ID NOs: 4, 6, 19 and 20 and a $V_L$ comprising an amino acid sequence selected from the amino acid sequences of SEQ ID NO: 5, 7, 8, 21 and 22. In some embodiments, the therapeutic catabody comprises: (i) a $V_H$ comprising the amino acid sequence of SEQ ID NO: 4, and a $V_L$ comprising the amino acid sequence of SEQ ID NO: 5; (ii) a $V_H$ comprising the amino acid sequence of SEQ ID NO: 6, and a $V_L$ comprising the amino acid sequence of SEQ ID NO: 7; (iii) a $V_H$ comprising the amino acid sequence of SEQ ID NO: 6, and a $V_L$ comprising the amino acid sequence of SEQ ID NO: 8; (iv) a V$_H$ comprising the amino acid sequence of SEQ ID NO: 19, and a V$_L$ comprising the amino acid sequence of SEQ ID NO: 21; (v) a V$_H$ comprising the amino acid sequence of SEQ ID NO: 20, and a V$_L$ comprising the amino acid sequence of SEQ ID NO: 21; (vi) a V$_H$ comprising the amino acid sequence of SEQ ID NO: 19, and a V$_L$ comprising the amino acid sequence of SEQ ID NO: 22; or (vii) a V$_H$ comprising the amino acid sequence of SEQ ID NO: 20, and a V$_L$ comprising the amino acid sequence of SEQ ID NO: 22. In some embodiments, the therapeutic catabody is a full-length IgG antibody. In some embodiments, the therapeutic catabody comprises an IgG1 or IgG4 Fc region. In some embodiments, the therapeutic catabody is a full-length IgM antibody.

Another aspect of the present application provides an isolated anti-AP catabody comprising: a V$_L$ comprising a LC-CDR1 comprising the amino acid sequence of SEQ ID NO: 12, an LC-CDR2 comprising the amino acid sequence of SEQ ID NO: 13, and an LC-CDR3 comprising the amino acid sequence of SEQ ID NO: 14, or a variant thereof comprising up to about 5 (e.g., 1, 2, 3, 4, or 5) amino acid substitutions in the LC-CDRs, wherein the amino acid residue at position 1 of the V$_L$ is D, the amino acid residue at position 27A of the V$_L$ is S. and the amino acid residue at position 93 of the V$_L$ is H. and wherein the numbering is according to the EU index of Kabat. In some embodiments, the anti-AP catabody comprises V$_H$ comprising an HC-CDR1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11, or a variant thereof comprising up to about 5 (e.g., 1, 2, 3, 4, or 5) amino acid substitutions in the HC-CDRs. In some embodiments, the isolated anti-Aβ catabody comprises: a V$_H$ comprising an HC-CDR1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11; and a V$_L$ comprising an LC-CDR1 comprising the amino acid sequence of SEQ ID NO: 12, an LC-CDR2 comprising the amino acid sequence of SEQ ID NO: 13, and an LC-CDR3 comprising the amino acid sequence of SEQ ID NO: 14.

In some embodiments, there is provided an isolated anti-Aβ catabody comprising: a V$_H$ comprising an HC-CDR1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11, or a variant thereof comprising up to about 5 (e.g., 1, 2, 3, 4, or 5) amino acid substitutions in the HC-CDRs, wherein the amino acid residue at position 1 of the V$_L$ is D, the amino acid residue at position 27A of the V$_L$ is S. and the amino acid residue at position 93 of the V$_L$ is H, and wherein the numbering is according to the EU index of Kabat. In some embodiments, the isolated anti-AP catabody comprises: a V$_L$ comprising a LC-CDR1 comprising the amino acid sequence of SEQ ID NO: 12, an LC-CDR2 comprising the amino acid sequence of SEQ ID NO: 13, and an LC-CDR3 comprising the amino acid sequence of SEQ ID NO: 14, or a variant thereof comprising up to about 5 (e.g., 1, 2, 3, 4, or 5) amino acid substitutions in the LC-CDRs. In some embodiments, the isolated anti-AP catabody comprises: a V$_H$ comprising an HC-CDR1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11; and a V$_L$ comprising an LC-CDR1 comprising the amino acid sequence of SEQ ID NO: 12, an LC-CDR2 comprising the amino acid sequence of SEQ ID NO: 13, and an LC-CDR3 comprising the amino acid sequence of SEQ ID NO: 14.

In some embodiments, there is provided an isolated anti-Aβ catabody comprising: a V$_H$ comprising an HC-CDR1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11; and a V$_L$ comprising an LC-CDR1 comprising the amino acid sequence of SEQ ID NO: 12, an LC-CDR2 comprising the amino acid sequence of SEQ ID NO: 13, and an LC-CDR3 comprising the amino acid sequence of SEQ ID NO: 14, wherein the amino acid residue at position 1 of the V$_L$ is D, the amino acid residue at position 27A of the V$_L$ is S, and the amino acid residue at position 93 of the V$_L$ is H, and wherein the numbering is according to the EU index of Kabat.

In some embodiments according to any one of the anti-Aβ catabodies described above, the anti-Aβ catabody cleaves a substrate having the formula EAR-AMC (SEQ ID NO: 1).

In some embodiments according to any one of the anti-Aβ catabodies described above, the amino acid residue at position 26 of the V$_L$ is S, the amino acid residue at position 27D of the V$_L$ is D, E or H, and/or the amino acid residue at position 28 of the V$_L$ is D or N, and wherein the numbering is according to the EU index of Kabat.

In some embodiments according to any one of the anti-Aβ catabodies described above, the anti-Aβ catabody comprises a V$_H$ comprising an amino acid sequence having at least about 85% sequence identity (e.g., at least about any one of 90%, 95%, 97%, 99%, or 100%) to the amino acid sequence of SEQ ID NO: 4, 6, 19 or 20. In some embodiments, the anti-Aβ catabody comprises a V$_L$ comprising an amino acid sequence having at least about 85% (e.g., at least about any one of 90%, 95%, 97%, 99%, or 100%) sequence identity to the amino acid sequence of SEQ ID NO: 5, 7, 8, 21 or 22. In some embodiments, the anti-Aβ catabody comprises a V$_H$ comprising an amino acid sequence selected from the amino acid sequences of SEQ ID NOs: 4, 6, 19 and 20 and a V$_L$ comprising an amino acid sequence selected from the amino acid sequences of SEQ ID NO: 5, 7, 8, 21 and 22. In some embodiments, the anti-Aβ catabody comprises: (i) a V$_H$ comprising the amino acid sequence of SEQ ID NO: 4, and a V$_L$ comprising the amino acid sequence of SEQ ID NO: 5; (ii) a V$_H$ comprising the amino acid sequence of SEQ ID NO: 6, and a V$_L$ comprising the amino acid sequence of SEQ ID NO: 7; (iii) a V$_H$ comprising the amino acid sequence of SEQ ID NO: 6, and a V$_L$ comprising the amino acid sequence of SEQ ID NO: 8; (iv) a V$_H$ comprising the amino acid sequence of SEQ ID NO: 19, and a V$_L$ comprising the amino acid sequence of SEQ ID NO: 21; (v) a V$_H$ comprising the amino acid sequence of SEQ ID NO: 20, and a V$_L$ comprising the amino acid sequence of SEQ ID NO: 21; (vi) a V$_H$ comprising the amino acid sequence of SEQ ID NO: 19, and a V$_L$ comprising the amino acid sequence of SEQ ID NO: 22; or (vii) a V$_H$ comprising the amino acid sequence of SEQ ID NO: 20, and a V$_L$ comprising the amino acid sequence of SEQ ID NO: 22.

In some embodiments according to any one of the anti-Aβ catabodies described above, the anti-Aβ catabody is a full-length IgG antibody. In some embodiments, the anti-Aβ catabody comprises an IgG1 or IgG4 Fc region. In some embodiments, the anti-Aβ catabody is a full-length IgM antibody.

In some embodiments, there is provided a method of treating or preventing Alzheimer's disease in an individual, comprising administering to the individual an effective amount of an anti-Aβ catabody according to any one of the anti-Aβ catabodies described above.

Also provided are methods of making and using the anti-Aβ catabodies, as well as kits and articles of manufacture useful for any one of methods described above.

In some embodiments, there is provided a kit for treating or preventing Alzheimer's disease in an individual, comprising: a) a substrate peptide comprises the amino acid sequence (EAR)$_n$ (SEQ ID NO: 2), and wherein n is an integer between 1 and 30 (e.g., n is 3); b) an Aβ peptide; and c) an antibody that specifically binds to total Ig (e.g., total human Ig). In some embodiments, the antibody specifically binds to total IgM, total IgG, total IgA, and/or total IgE. In some embodiments, the kit further comprises a solid support, such as an ELISA plate. In some embodiments, the kit further comprises a therapeutic catabody that specifically binds to Aβ.

BRIEF DESCRIPTION OF THE DRAWINGS

FIG. 4 shows an SDS gel image of various purified 3D6-derived catabodies under non-reducing and reducing electrophoresis conditions. 3D6-D is a catabody designed based on 3D6 (i.e., 3D6-Y). hu3D6-D H1L1 and hu3D6-D H1L2 are humanized versions of 3D6-D. hu3D6-Y has the same sequences as bapineuzumab (i.e., humanized 3D6).

FIG. 5 shows catalytic function of 3D6-D as determined using an EAR-AMC substrate.

FIG. 8 shows anti-Aβ autoantibody levels and SHD catabody (recognizing (EAR)$_3$) levels in the serum of 30 Alzheimer's disease (AD) patients measured by ELISA assay. PBS served as negative control. The average readout from pooled healthy human serum and serum samples of 8 healthy donors served as control. The "% of Control" was calculated as (readout of AD sample) divided by (average readout of pooled human serum and serum of 8 healthy donors). "+" in the table indicates the serum level of anti-Aβ autoantibody or SHD catabody in AD patient serum is higher than that of healthy donor and pooled serum samples. "−" in the table indicates the serum level of anti-Aβ autoantibody or SHD catabody in AD patient serum is lower than that of healthy donor and pooled serum samples.

FIG. 9A depicts ELISA experimental design for detecting anti-Aβ autoantibody levels and SHD catabody (recognizing (EAR)$_3$) levels in the serum of 30 Alzheimer's disease (AD) patients, 8 healthy donors, and pooled healthy donor serum sample. PBS served as negative control. FIG. 9B depicts plate reading for Aβ ELISA binding assay at 5 min time point. FIG. 9C depicts plate reading for (EAR)$_3$ ELISA binding assay at 1 min time point.

DETAILED DESCRIPTION OF THE INVENTION

Figure 1A:
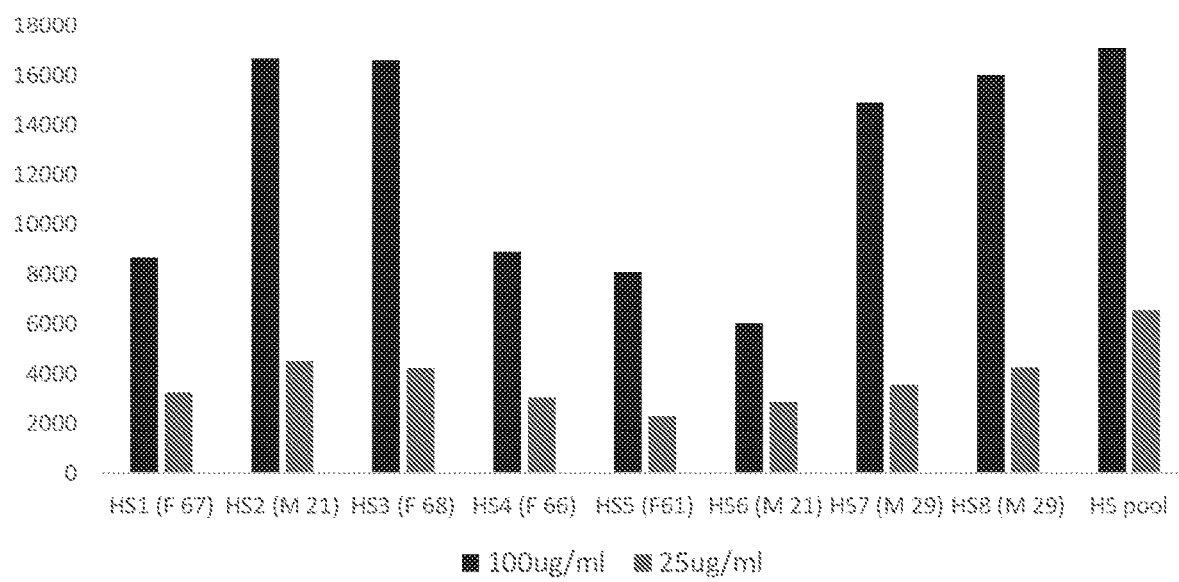
FIG. 1A shows catabody levels in the serum samples of young (20-29 years old) and old (60-69 years old) adults as determined by an EAR-AMC binding assay.

The present application in one aspect provides methods for diagnosis and treatment of a protein aggregation disease (PAD) using a newly developed immunoassay for determining SHD catabody levels in a biological sample. The present application is based in part on the discovery that SHD catabody levels in the serum correlate with auto-antibody levels against amyloid beta (Aβ) peptides in aging individuals and patients having Alzheimer's disease (AD). Currently, imaging is still the most reliable diagnosis method for AD. However, when the disease shows clear pathologic features in the imaging analysis, neural damage has already occurred. At this stage, even if a therapeutic agent can prevent further progression of the disease, the therapeutic agent is unlikely to reverse the neural damage. The present invention allows effective diagnosis and treatment of PAD (such as AD) at an early stage using SHD catabody levels as an early diagnostic biomarker.

Additionally, using antibody engineering, catabodies that specifically recognize and cleave Aβ have been designed based on a non-catalytic anti-Aβ antibody 3D6, the parental murine antibody of Bapineuzumab. Bapineuzumab was shown to be safe at low dosage, but two large Phase III clinical trials showed no efficacy of Bapineuzumab in treating late-stage AD patients. Because AD patients have comprised blood-brain barrier (BBB) due to accumulation of Aβ1-40 (Aβ40), conventional therapeutic antibodies such as Bapineuzumab can penetrate the BBB and exacerbate neuroinflammation. Compared to bapineuzumab, the anti-Aβ catabodies described herein have enhanced efficacy at low dosage due to their catalytic activity. In some embodiments, an individual having a risk of AD can be determined at an early stage using the methods described herein, and treated with an anti-Aβ catabody described herein to prevent AD.

Accordingly, one aspect of the present application provides a method for determining a risk for a PAD in an individual, wherein the PAD is associated with aggregation of a target protein, comprising determining the level of one or more SHD catabodies in a biological sample (e.g., serum sample) of the individual, wherein the individual is determined as having a risk for the PAD if the level of the one or more SHD catabodies is lower than a control SHD catabody level. In some embodiments, the method comprises: a) contacting a serum sample of the individual with a substrate peptide immobilized on a solid support under conditions that allow formation of a catabody-substrate peptide complex, and b) determining the amount of the catabody-substrate peptide complex, thereby providing the level of one or more SHD catabodies in the biological sample, wherein the substrate peptide comprises the amino acid sequence (EAR)$_n$ (SEQ ID NO: 2), and wherein n is an integer between 1 and 30. In some embodiments, the method further comprises determining the level of an auto-antibody against the target protein in a biological sample (e.g., serum sample) of the individual, and wherein the individual is determined as having a risk for the PAD if: (i) the level of the one or more SHD catabodies is lower than a control SHD catabody level; and (ii) the level of the auto-antibody against the target protein is lower than a control auto-antibody level.

One aspect of the present application provides a method of treating or preventing a PAD (e.g., AD) in an individual, wherein the PAD is associated with aggregation of a target protein (e.g., Aβ), comprising: a) determining the level of one or more SHD catabodies in a biological sample (e.g., serum sample) of the individual, wherein the individual is determined as having a risk for the PAD if the level of the one or more SHD catabodies is lower than a control SHD catabody level; and b) administering to the individual an effective amount of a therapeutic catabody that specifically binds to the target protein (e.g., Aβ). In some embodiments, step a) comprises: 1) contacting a serum sample of the individual with a substrate peptide immobilized on a solid support under conditions that allow formation of a catabody-substrate peptide complex, and 2) determining the amount of the catabody-substrate peptide complex, thereby providing the level of one or more SHD catabodies in the serum, wherein the substrate peptide comprises the amino acid sequence (EAR)$_n$(SEQ ID NO: 2), and wherein n is an integer between 1 and 30. In some embodiments, step a) further comprises determining the level of an auto-antibody against the target protein in a biological sample (e.g., serum sample) of the individual, and wherein the individual is determined as having a risk for the PAD if: (i) the level of the one or more SHD catabodies is lower than a control SHD catabody level; and (ii) the level of the auto-antibody against the target protein is lower than a control auto-antibody level.

Another aspect of the present application provides an isolated anti-Aβ catabody comprising a light chain variable region ($V_L$) comprising a light chain complementarity determining region (LC-CDR) 1 comprising the amino acid sequence of SEQ ID NO: 12, an LC-CDR2 comprising the amino acid sequence of SEQ ID NO: 13, and an LC-CDR3 comprising the amino acid sequence of SEQ ID NO: 14, or a variant thereof comprising up to about 5 amino acid substitutions in the LC-CDRs, wherein the amino acid residue at position 1 of the $V_L$ is D, the amino acid residue at position 27A of the $V_L$ is S, and the amino acid residue at position 93 of the $V_L$ is H, and wherein the numbering is according to the EU index of Kabat. In some embodiments, the anti-Aβ catabody comprises a heavy chain variable region ($V_H$) comprising a heavy chain complementarity determining region (HC-CDR) 1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11, or a variant thereof comprising up to about 5 amino acid substitutions in the HC-CDRs.

Also provided are compositions (such as pharmaceutical compositions), kits and articles of manufacture for diagnosis, treatment or prevention of PAD (e.g., AD).

I. Definitions

As used herein, "treatment" or "treating" is an approach for obtaining beneficial or desired results, including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. The methods of the invention contemplate any one or more of these aspects of treatment.

The term "antibody" includes full-length antibodies and antigen-binding fragments thereof. A full-length antibody comprises two heavy chains and two light chains. The variable regions of the light and heavy chains are responsible for antigen binding. The variable regions in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat. Chothia. or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The term "antigen-binding fragment" as used herein refers to an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain Fv (scFv), an scFv dimer (bivalent diabody), a multispecific antibody formed from a portion of an antibody comprising one or more CDRs, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

The term "epitope" as used herein refers to the specific group of atoms or amino acids on an antigen to which an antibody binds. Two antibodies may bind the same epitope within an antigen if they exhibit competitive binding for the antigen.

As use herein, the term "specifically binds," "specifically recognizing," or "is specific for" refers to measurable and reproducible interactions, such as binding between a target and an antibody (e.g., catabody), that is determinative of the presence of the target in the presence of a heterogeneous population of molecules, including biological molecules. For example, an antibody that specifically recognizes a target (which can be an epitope) is an antibody that binds this target with greater affinity, avidity, more readily, and/or with greater duration than its bindings to other targets. In some embodiments, an antibody that specifically recognizes an antigen reacts with one or more antigenic determinants of the antigen with a binding affinity that is at least about 10 times its binding affinity for other targets.

The term "catabody" as used herein refers to an antibody with catalytic activity. For example, a catabody can catalyze hydrolysis of the target antigen that it specifically recognizes. Exemplary catabodies include, but are not limited to, proteolytic antibodies. Catabodies are also known as catalytic antibodies, Abzymes and Catmabs.

The term "SHD catabody" as used herein refers to a proteolytic catabody having an SHD motif in the light chain variable region ($V_L$). The "SHD motif" refers to serine, histidine, and aspartate residues that together serve as the catalytic triad for peptide bond cleavage by the catabody. In some embodiments, the SHD motif is a non-linear motif, in which the serine, histidine and aspartate residues of the catalytic triad are not next to each other in the amino acid sequence.

An "isolated" antibody as used herein refers to an antibody that (1) is not associated with proteins found in nature, (2) is free of other proteins from the same source, (3) is expressed by a cell from a different species, or, (4) does not occur in nature.

The term "isolated nucleic acid" as used herein is intended to mean a nucleic acid of genomic, cDNA, or synthetic origin or some combination thereof, which by virtue of its origin the "isolated nucleic acid" (1) is not associated with all or a portion of a polynucleotide in which the "isolated nucleic acid" is found in nature. (2) is operably linked to a polynucleotide which it is not linked to in nature, or (3) does not occur in nature as part of a larger sequence.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); Chothia et al., J. Mol. Biol. 196: 901-917 (1987); Al-Lazikani B. et al., *J. Mol. Biol.,* 273: 927-948 (1997); MacCallum et al., J. Mol. Biol. 262:732-745 (1996); Abhinandan and Martin, *Mol. Immunol.,* 45: 3832-3839 (2008); Lefranc M. P. et al., *Dev. Comp. Immunol.,* 27: 55-77 (2003); and Honegger and Pluickthun, *J. Mol. Bio.,* 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison. CDR prediction algorithms and interfaces are known in the art, including, for example, Abhinandan and Martin, *Mol. Immunol.,* 45: 3832-3839 (2008); Ehrenmann F. et al., *Nucleic Acids Res.,* 38: D301-D307 (2010); and Adolf-Bryfogle J. et al, *Nucleic Acids Res.,* 43: D432-D438 (2015). The contents of the references cited in this paragraph are incorporated herein by reference in their entireties for use in the present invention and for possible inclusion in one or more claims herein.

TABLE 1

| CDR DEFINITIONS | | | | | |
|---|---|---|---|---|---|
| | Kabat[1] | Chothia[2] | MacCallum[3] | IMGT[4] | AHo[5] |
| $V_H$ CDR1 | 31-35 | 26-32 | 30-35 | 27-38 | 25-40 |
| $V_H$ CDR2 | 50-65 | 53-55 | 47-58 | 56-65 | 58-77 |

TABLE 1-continued

| CDR DEFINITIONS | | | | | |
|---|---|---|---|---|---|
| | Kabat[1] | Chothia[2] | MacCallum[3] | IMGT[4] | AHo[5] |
| $V_H$ CDR3 | 95-102 | 96-101 | 93-101 | 105-117 | 109-137 |
| $V_L$ CDR1 | 24-34 | 26-32 | 30-36 | 27-38 | 25-40 |
| $V_L$ CDR2 | 50-56 | 50-52 | 46-55 | 56-65 | 58-77 |
| $V_L$ CDR3 | 89-97 | 91-96 | 89-96 | 105-117 | 109-137 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Plückthun, supra The term "chimeric antibodies" refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., Proc. Natl. Acad. Sci. USA, 81:6851-6855 (1984)).

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the $V_H$ and $V_L$ antibody domains connected into a single polypeptide chain. In some embodiments, the scFv polypeptide further comprises a polypeptide linker between the $V_H$ and $V_L$ domains which enables the scFv to form the desired structure for antigen binding. For a review of scFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing scFv fragments (see preceding paragraph) typically with short linkers (such as about 5 to about 10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" scFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad Sci. USA,* 90:6444-6448 (1993).

"Humanized" forms of non-human (e.g., rodent) antibodies (e.g., catabodies) are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al, *Nature* 321:522-525 (1986); Riechmann et al., *Nature* 332: 323-329 (1988); and Presta, *Curr. Op. Struct. Biol.* 2:593-596 (1992).

"Percent (%) amino acid sequence identity" or "homology" with respect to the polypeptide and antibody (e.g., catabody) sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., *Nucleic Acids Research* 32(5): 1792-1797, 2004; Edgar, R. C., *BMC Bioinformatics* 5(1): 113, 2004).

The terms "Fc receptor" or "FcR" are used to describe a receptor that binds to the Fc region of an antibody. In some embodiments, an FcR of this invention is one that binds an IgG antibody (a γ receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.* 15:203-234 (1997)). The term includes allotypes, such as FcγRIIIA allotypes: FcγRIIIA-Phe158, FcγRIIIA-Val158. FcγRIIA-R131 and/or FcγRIIA-H131. FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The term "FcRn" refers to the neonatal Fc receptor (FcRn). FcRn is structurally similar to major histocompatibility complex (MHC) and consists of an α-chain noncovalently bound to β2-microglobulin. The multiple functions of the neonatal Fc receptor FcRn are reviewed in Ghetie and Ward (2000) *Annu. Rev. Immunol.* 18, 739-766. FcRn plays a role in the passive delivery of immunoglobulin IgGs from mother to young and the regulation of serum IgG levels. FcRn can act as a salvage receptor, binding and transporting pinocytosed IgGs in intact form both within and across cells, and rescuing them from a default degradative pathway.

The "CH1 domain" of a human IgG Fc region (also referred to as "C1" of "H1" domain) usually extends from about amino acid 118 to about amino acid 215 (EU numbering system).

"Hinge region" is generally defined as stretching from Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "CH2 domain" of a human IgG Fc region (also referred to as "C2" of "H2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec Immunol.* 22:161-206 (1985).

The "CH3 domain" (also referred to as "C2" or "H3" domain) comprises the stretch of residues C-terminal to a CH2 domain in an Fc region (i.e. from about amino acid residue 341 to the C-terminal end of an antibody sequence, typically at amino acid residue 446 or 447 of an IgG).

A "functional Fc fragment" possesses an "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art.

An antibody with a variant IgG Fc with "altered" FcR binding affinity or ADCC activity is one which has either enhanced or diminished FcR binding activity (e.g., FcγR or FcRn) and/or ADCC activity compared to a parent polypeptide or to a polypeptide comprising a native sequence Fc region. The variant Fc which "exhibits increased binding" to an FcR binds at least one FcR with higher affinity (e.g., lower apparent $K_d$ or $IC_{50}$ value) than the parent polypeptide or a native sequence IgG Fc. According to some embodiments, the improvement in binding compared to a parent polypeptide is about 3 fold, such as about any of 5, 10, 25, 50, 60, 100, 150, 200, or up to 500 fold, or about 25% to 1000% improvement in binding. The polypeptide variant which "exhibits decreased binding" to an FcR, binds at least one FcR with lower affinity (e.g., higher apparent $K_d$ or higher $IC_{50}$ value) than a parent polypeptide. The decrease in binding compared to a parent polypeptide may be about 40% or more decrease in binding.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS (USA)* 95:652-656 (1998).

The polypeptide comprising a variant Fc region which "exhibits increased ADCC" or mediates ADCC in the presence of human effector cells more effectively than a polypeptide having wild type IgG Fc or a parent polypeptide is one which in vitro or in vivo is substantially more effective at mediating ADCC, when the amounts of polypeptide with variant Fc region and the polypeptide with wild type Fc region (or the parent polypeptide) in the assay are essentially the same. Generally, such variants will be identified using any in vitro ADCC assay known in the art, such as assays or methods for determining ADCC activity, e.g., in an animal model etc. In some embodiments, the variant is from about 5 fold to about 100 fold, e.g. from about 25 to about 50 fold, more effective at mediating ADCC than the wild type Fc (or parent polypeptide).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al, *J. Immunol Methods* 202:163 (1996), may be performed. Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See also, Idusogie et al. *J. Immunol* 164: 4178-4184 (2000).

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

An "effective amount" of an antibody or composition as disclosed herein, is an amount sufficient to carry out a specifically stated purpose. An "effective amount" can be determined empirically and by known methods relating to the stated purpose.

As used herein, by "pharmaceutically acceptable" or"pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter.

As used herein and in the appended claims, the singular forms "a," "or," and "the" include plural referents unless the context clearly dictates otherwise.

II. Methods of Diagnosis and Treatment

The present application provides methods for determining levels of one or more catabodies (e.g., SHD catabodies) in a sample, and methods for diagnosing (including determining a risk), treating or preventing a protein aggregation disease (PAD) in an individual. In some embodiments, the level of one or more catabodies (e.g., SHD catabodies) is the protein level of the one or more catabodies. In some embodiments, the level of one or more catabodies is the mRNA level of the one or more catabodies. In some embodiments, the methods described herein use a substrate peptide in an immunoassay to detect binding of the substrate peptide with one or more catabodies (e.g., SHD catabodies) in a sample, thereby providing the level of one or more catabodies in the sample. In some embodiments, the level of one or more catabodies is the level of total catabodies, such as total SHD catabodies. In some embodiments, the level of one or more catabodies is the level of one or more (such as 1, 2, 3, 4, or more) catabodies (e.g., total SHD catabody levels) that specifically bind and cleave a target protein (e.g., Aβ) that is associated with a PAD.

In some embodiments, the level of total SHD catabodies is determined based on binding of the catabodies to a substrate peptide comprising the amino acid sequence $(EAR)_n$ (SEQ ID NO: 2), wherein n is an integer between 1 and 30. The substrate peptide may comprise any suitable number of EAR repeats, including, for example, about any one of, 1-10, 10-20, 20-30, 1-30, 1-5, 5-10, 5-15, or 15-30. In some embodiments, the substrate peptide comprises the amino acid sequence SEQ ID NO: 2, wherein n is about any one of 1, 2, 3, 4, 5, 6, 7, 8, 9, or 10. In some embodiments, the amino acid sequence of SEQ ID NO: 2 is at the N-terminus, C-terminus, or an internal position in the substrate peptide. In some embodiments, the substrate peptide comprises amino acid residues in addition to the amino acid sequence of SEQ ID NO: 2, e.g., at the N-terminus and/or C-terminus of the amino acid sequence of SEQ ID NO:2. In some embodiments, the substrate peptide comprises at least about any one of 1, 2, 3, 5, 10, 15, 20, 25, or 30 amino acids in addition to the amino acid sequence of SEQ ID NO: 2. In some embodiments, the substrate peptide has a total length of about 3-100 amino acids, such as about any one of 3-10, 10-20, 20-30, 30-40, 40-50, 50-60, 60-70, 70-80, 80-90, 90-100, 3-50, 50-100, 10-30, 30-60, 60-90, 20-40, 40-60, 60-80 or 80-100 amino acids. In some embodiments, the substrate peptide comprises a label, e.g., a fluorescent label, a peptide tag, or a biotin label. In some embodiments, the substrate peptide comprises the formula EAR-AMC (SEQ ID NO: 1).

Although EAR-AMC, i.e., a peptide having the amino acid sequence EAR conjugated to 7-amino-4-methylcoumarin (AMC), is a known proteolytic substrate of SHD catabodies, a substrate peptide comprising the amino acid sequence of SEQ ID NO: 2 has not been used to measure the binding activity and levels of catabodies in a biological sample. It is also unpredictable whether the binding between the EAR peptides and the SHD catabodies is strong and long-lasting enough to allow accurate determination of the level of SHD catabodies via a binding assay. The present application provides an immunoassay using a substrate peptide comprising the amino acid sequence of SEQ ID NO: 2, which provides accurate readout for the level of total SHD catabodies in a biological sample (e.g., serum sample).

Accordingly, in some embodiments, there is provided a method for determining the level of one or more SHD catabodies in a biological sample, comprising: a) contacting the biological sample with a substrate peptide immobilized on a solid support under conditions that allow formation of a catabody-substrate peptide complex, and b) determining the amount of the catabody-substrate peptide complex, thereby providing the level of one or more SHD catabodies in the biological sample, wherein the substrate peptide comprises the amino acid sequence $(EAR)_0$ (SEQ ID NO: 2), and wherein n is an integer between 1 and 30. In some embodiments, n is 1, 2, 3, 4, 5, 6, 7, 8, 9, or 10. In some embodiments, the substrate peptide has the formula EAR-AMC (SEQ ID NO: 1). In some embodiments, the substrate peptide comprises the amino acid sequence EAREAREAR (SEQ ID NO: 3). In some embodiments, the solid support is an ELISA plate.

In some embodiments, there is provided a method for determining the level of one or more SHD catabodies in a biological sample, comprising: a) contacting the biological sample with a substrate peptide immobilized on a solid support under conditions that allow formation of a catabody-substrate peptide complex, and b) determining the amount of the catabody-substrate peptide complex using an antibody that specifically binds to total Ig (e.g., total human Ig, such as total IgM, total IgG, total IgA, and/or total IgE), thereby providing the level of one or more SHD catabodies in the biological sample, wherein the substrate peptide comprises the amino acid sequence $(EAR)_n$ (SEQ ID NO: 2), and wherein n is an integer between 1 and 30 (e.g., n is 3). In some embodiments, the antibody is labeled with an enzyme (e.g., HRP) or a fluorescent label (e.g., FITC). In some embodiments, the solid support is an ELISA plate.

In some embodiments, there is provided a method for determining the level of one or more SHD catabodies in a biological sample, comprising: a) contacting the biological sample with a substrate peptide immobilized on a solid support under conditions that allow formation of a catabody-substrate peptide complex, and b) determining the amount of the catabody-substrate peptide complex using an antibody that specifically binds to total Ig (e.g., total human Ig, such as total IgM, total IgG, total IgA, and/or total IgE), thereby providing the level of one or more SHD catabodies in the biological sample, wherein the substrate peptide comprises the amino acid sequence of SEQ ID NO: 3. In some embodiments, the antibody is labeled with an enzyme (e.g., HRP) or a fluorescent label (e.g., FITC). In some embodiments, the solid support is an ELISA plate.

In some embodiments, there is provided a method for determining the level of one or more SHD catabodies in a biological sample, comprising: a) contacting a substrate peptide with an ELISA plate to coat the wells of the ELISA plate with the substrate peptide; b) contacting the biological sample with a coated well of the ELISA plate under conditions that allow formation of a catabody-substrate peptide complex, and b) determining the amount of the catabody-substrate peptide complex using an antibody that specifically binds to total Ig (e.g., total human Ig, such as total IgM, total IgG, total IgA, and/or total IgE) labeled with an enzyme (e.g., HRP) or a fluorescent label (e.g., FITC), thereby providing the level of one or more SHD catabodies in the biological sample, wherein the substrate peptide comprises the amino acid sequence of SEQ ID NO: 3.

In some embodiments, there is provided a method for determining a risk for a protein aggregation disease (PAD) in an individual, wherein the PAD is associated with aggregation of a target protein, comprising determining the level of one or more SHD catabodies in a biological sample (e.g., serum sample) of the individual, wherein the individual is determined as having a risk for the PAD if the level of the one or more SHD catabodies is lower than a control SHD catabody level. In some embodiments, the level of one or more SHD catabodies is the level of one or more SHD catabodies that specifically bind to the target protein. In some embodiments, the level of one or more SHD catabodies is the level of total SHD catabodies. In some embodiments, the level of total SHD catabodies is determined by contacting a serum sample of the individual with a substrate peptide under conditions that allow formation of a catabody-substrate peptide complex, and determining the amount of the catabody-substrate peptide complex. In some embodiments, the substrate peptide is immobilized on a solid support. In some embodiments, the level of the one or more SHD catabodies is determined using any one of the methods of determining SHD catabody levels described herein. In some embodiments, (i) the PAD is Alzheimer's disease, and the target protein is Aβ; (ii) the PAD is Parkinson's disease, and the target protein is α-synuclein; (iii) the PAD is Alzheimer's disease or dementia, and the target protein is Tau; (iv) the PAD is ATTR amyloidosis, and the target protein is transthyretin; (v) the PAD is AL amyloidosis, and the target protein is immunoglobulin light chain; (vi) the PAD is FTLD or ALS, and the target protein is TDP43; (vii) the PAD is Huntington's disease, and the target protein is Huntingtin; (viii) the PAD is Type II diabetes, and the target protein is IAPP; and (ix) the PAD is ALS, and the target protein is SOD1.

In some embodiments, there is provided a method for determining a risk for Alzheimer's disease (AD) in an individual, comprising: a) contacting a serum sample from the individual with a substrate peptide immobilized on a solid support under conditions that allow formation of a catabody-substrate peptide complex, and b) determining the amount of one or more SHD catabodies that specifically bind to Aβ, and wherein the individual is determined as having a risk for the AD if the level of one or more SHD catabodies is lower than a control SHD catabody level.

In some embodiments, there is provided a method for determining a risk for a PAD in an individual, wherein the PAD is associated with aggregation of a target protein, comprising a) determining the level of one or more SHD catabodies in a biological sample (e.g., serum sample) of the individual, and b) determining the level of an auto-antibody against the target protein in a biological sample (e.g., serum sample) of the individual, and wherein the individual is determined as having a risk for the PAD if: (i) the level of the one or more SHD catabodies is lower than a control SHD catabody level; and (ii) the level of the auto-antibody against the target protein is lower than a control auto-antibody level. In some embodiments, the level of one or more SHD catabodies is the level of one or more SHD catabodies that specifically bind to the target protein. In some embodiments, the level of one or more SHD catabodies is the level of total SHD catabodies. In some embodiments, the level of total SHD catabodies is determined by contacting a serum sample of the individual with a substrate peptide under conditions that allow formation of a catabody-substrate peptide complex, and determining the amount of the catabody-substrate peptide complex. In some embodiments, the substrate peptide is immobilized on a solid support. In some embodiments, the level of the one or more SHD catabodies is determined using any one of the methods of determining SHD catabody levels described herein. In some embodiments, the level of the auto-antibody is determined by contacting a serum sample of the individual with the target protein (or a fragment thereof) under conditions that allow formation of an auto-antibody-target protein complex, and determining the amount of the auto-antibody-target protein complex. In some embodiments, the level of the auto-antibody is determined using an ELISA assay. In some embodiments, (i) the PAD is Alzheimer's disease, and the target protein is Aβ; (ii) the PAD is Parkinson's disease, and the target protein is α-synuclein; (iii) the PAD is Alzheimer's disease or dementia, and the target protein is Tau; (iv) the PAD is ATTR amyloidosis, and the target protein is transthyretin; (v) the PAD is AL amyloidosis, and the target protein is immunoglobulin light chain; (vi) the PAD is FTLD or ALS, and the target protein is TDP43; (vii) the PAD is Huntington's disease, and the target protein is Huntingtin; (viii) the PAD is Type II diabetes, and the target protein is IAPP; and (ix) the PAD is ALS, and the target protein is SOD1.

In some embodiments, there is provided a method for determining a risk for a PAD in an individual, wherein the PAD is associated with aggregation of a target protein, comprising a) determining the level of one or more SHD catabodies in a biological sample (e.g., serum sample) of the individual, and b) determining the level of the target protein in a biological sample (e.g., serum sample or cerebrospinal fluid sample) of the individual, and wherein the individual is determined as having a risk for the PAD if: (i) the level of the one or more SHD catabodies is lower than a control SHD catabody level; and (ii) the level of the target protein is higher than a control target protein level. In some embodiments, the level of one or more SHD catabodies is the level of one or more SHD catabodies that specifically bind to the target protein. In some embodiments, the level of one or more SHD catabodies is the level of total SHD catabodies. In some embodiments, the level of total SHD catabodies is determined by contacting a serum sample of the individual with a substrate peptide under conditions that allow formation of a catabody-substrate peptide complex, and determining the amount of the catabody-substrate peptide complex. In some embodiments, the substrate peptide is immobilized on a solid support. In some embodiments, the level of the one or more SHD catabodies is determined using any one of the methods of determining SHD catabody levels described herein. In some embodiments, the level of the target protein is determined by contacting the biological sample of the individual with an antibody against the target protein under conditions that allow formation of an antibody-target protein complex, and determining the amount of the antibody-target protein complex. In some embodiments, the level of the target protein is determined using an ELISA assay. In some embodiments, (i) the PAD is Alzheimer's disease, and the target protein is Aβ; (ii) the PAD is Parkinson's disease, and the target protein is α-synuclein; (iii) the PAD is Alzheimer's disease or dementia, and the target protein is Tau; (iv) the PAD is ATTR amyloidosis, and the target protein is transthyretin; (v) the PAD is AL amyloidosis, and the target protein is immunoglobulin light chain; (vi) the PAD is FTLD or ALS, and the target protein is TDP43; (vii) the PAD is Huntington's disease, and the target protein is Huntingtin; (viii) the PAD is Type II diabetes, and the target protein is IAPP; and (ix) the PAD is ALS, and the target protein is SOD1.

In some embodiments, there is provided a method for determining a risk for a PAD in an individual, wherein the PAD is associated with aggregation of a target protein, comprising: a) contacting a serum sample of the individual with a substrate peptide immobilized on a solid support under conditions that allow formation of a catabody-substrate peptide complex, wherein the substrate peptide comprises the amino acid sequence $(EAR)_n$ (SEQ ID NO: 2), wherein n is an integer between 1 and 30 (e.g., n is 3); b) determining the amount of the catabody-substrate peptide complex, thereby providing the level of one or more SHD catabodies in the serum of the individual; and c) determining the level of an auto-antibody against the target protein in a biological sample (e.g., serum sample) of the individual, and wherein the individual is determined as having a risk for the PAD if: (i) the level of the one or more SHD catabodies is lower than a control SHD catabody level; and (ii) the level of the auto-antibody against the target protein is lower than a control auto-antibody level. In some embodiments, the solid support is an ELISA plate. In some embodiments, the level of the auto-antibody is determined by contacting a serum sample of the individual with the target protein (or a fragment thereof) under conditions that allow formation of an auto-antibody-target protein complex, and determining the amount of the auto-antibody-target protein complex. In some embodiments, the level of the auto-antibody is determined using an ELISA assay. In some embodiments, (i) the PAD is Alzheimer's disease, and the target protein is Aβ; (ii) the PAD is Parkinson's disease, and the target protein is α-synuclein; (iii) the PAD is Alzheimer's disease or dementia, and the target protein is Tau; (iv) the PAD is ATTR amyloidosis, and the target protein is transthyretin; (v) the PAD is AL amyloidosis, and the target protein is immunoglobulin light chain; (vi) the PAD is FTLD or ALS, and the target protein is TDP43; (vii) the PAD is Huntington's disease, and the target protein is Huntingtin; (viii) the PAD is Type II diabetes, and the target protein is IAPP; and (ix) the PAD is ALS, and the target protein is SOD1.

In some embodiments, there is provided a method for determining a risk for a PAD in an individual, wherein the PAD is associated with aggregation of a target protein, comprising: a) contacting a serum sample of the individual with a substrate peptide immobilized on a solid support under conditions that allow formation of a catabody-substrate peptide complex, wherein the substrate peptide comprises the amino acid sequence (EAR)$_n$ (SEQ ID NO: 2), wherein n is an integer between 1 and 30 (e.g., n is 3); b) determining the amount of the catabody-substrate peptide complex, thereby providing the level of one or more SHD catabodies in the serum of the individual; and c) determining the level of the target protein in a biological sample (e.g., serum sample or cerebrospinal fluid sample) of the individual, and wherein the individual is determined as having a risk for the PAD if: (i) the level of the one or more SHD catabodies is lower than a control SHD catabody level; and (ii) the level of the target protein is higher than a control target protein level. In some embodiments, the solid support is an ELISA plate. In some embodiments, the level of the target protein is determined by contacting the biological sample of the individual with an antibody against the target protein under conditions that allow formation of an antibody-target protein complex, and determining the amount of the antibody-target protein complex. In some embodiments, the level of the target protein is determined using an ELISA assay. In some embodiments, (i) the PAD is Alzheimer's disease, and the target protein is Aβ; (ii) the PAD is Parkinson's disease, and the target protein is α-synuclein; (iii) the PAD is Alzheimer's disease or dementia, and the target protein is Tau; (iv) the PAD is ATTR amyloidosis, and the target protein is transthyretin; (v) the PAD is AL amyloidosis, and the target protein is immunoglobulin light chain; (vi) the PAD is FTLD or ALS, and the target protein is TDP43; (vii) the PAD is Huntington's disease, and the target protein is Huntingtin; (viii) the PAD is Type II diabetes, and the target protein is IAPP; and (ix) the PAD is ALS, and the target protein is SOD1.

In some embodiments, there is provided a method for determining a risk for a PAD in an individual, wherein the PAD is associated with aggregation of a target protein, comprising: a) contacting a serum sample from the individual with a substrate peptide immobilized on a solid support under conditions that allow formation of a catabody-substrate peptide complex, wherein the substrate peptide comprises the amino acid sequence (EAR)$_n$ (SEQ ID NO: 2), wherein n is an integer between 1 and 30 (e.g., n is 3); b) determining the amount of the catabody-substrate peptide complex using an antibody that specifically binds to total Ig (e.g., total human Ig, such as total IgM, total IgG, total IgA, and/or total IgE), thereby providing the level of one or more SHD catabodies in the serum of the individual; and c) determining the level of an auto-antibody against the target protein in a biological sample (e.g., serum sample) of the individual, and wherein the individual is determined as having a risk for the PAD if: (i) the level of the one or more SHD catabodies is lower than a control SHD catabody level; and (ii) the level of the auto-antibody against the target protein is lower than a control auto-antibody level. In some embodiments, the antibody specifically binding to Ig is labeled with an enzyme (e.g., HRP) or a fluorescent label (e.g., FITC). In some embodiments, the solid support is an ELISA plate. In some embodiments, the level of the auto-antibody is determined by contacting a serum sample of the individual with the target protein (or a fragment thereof) under conditions that allow formation of an auto-antibody-target protein complex, and determining the amount of the auto-antibody-target protein complex. In some embodiments, the level of the auto-antibody is determined using an ELISA assay. In some embodiments, (i) the PAD is Alzheimer's disease, and the target protein is Aβ; (ii) the PAD is Parkinson's disease, and the target protein is α-synuclein; (iii) the PAD is Alzheimer's disease or dementia, and the target protein is Tau; (iv) the PAD is ATTR amyloidosis, and the target protein is transthyretin: (v) the PAD is AL amyloidosis, and the target protein is immunoglobulin light chain; (vi) the PAD is FTLD or ALS, and the target protein is TDP43; (vii) the PAD is Huntington's disease, and the target protein is Huntingtin; (viii) the PAD is Type II diabetes, and the target protein is IAPP; and (ix) the PAD is ALS, and the target protein is SOD1.

In some embodiments, there is provided a method for determining a risk for a PAD in an individual, wherein the PAD is associated with aggregation of a target protein, comprising: a) contacting a serum sample from the individual with a substrate peptide immobilized on a solid support under conditions that allow formation of a catabody-substrate peptide complex, wherein the substrate peptide comprises the amino acid sequence (EAR)$_n$ (SEQ ID NO: 2), wherein n is an integer between 1 and 30 (e.g., n is 3); b) determining the amount of the catabody-substrate peptide complex using an antibody that specifically binds to total Ig (e.g., total human Ig, such as total IgM, total IgG, total IgA, and/or total IgE), thereby providing the level of one or more SHD catabodies in the serum of the individual; and c) determining the level of the target protein in a biological sample (e.g., serum sample or cerebrospinal fluid sample) of the individual, and wherein the individual is determined as having a risk for the PAD if: (i) the level of the one or more SHD catabodies is lower than a control SHD catabody level; and (ii) the level of the target protein is higher than a control target protein level. In some embodiments, the solid support is an ELISA plate. In some embodiments, the level of the target protein is determined by contacting the biological sample of the individual with an antibody against the target protein under conditions that allow formation of an antibody-target protein complex, and determining the amount of the antibody-target protein complex. In some embodiments, the level of the target protein is determined using an ELISA assay. In some embodiments, (i) the PAD is Alzheimer's disease, and the target protein is Aβ; (ii) the PAD is Parkinson's disease, and the target protein is α-synuclein; (iii) the PAD is Alzheimer's disease or dementia, and the target protein is Tau, (iv) the PAD is ATTR amyloidosis, and the target protein is transthyretin; (v) the PAD is AL amyloidosis, and the target protein is immunoglobulin light chain; (vi) the PAD is FTLD or ALS, and the target protein is TDP43; (vii) the PAD is Huntington's disease, and the target protein is Huntingtin; (viii) the PAD is Type II diabetes, and the target protein is IAPP; and (ix) the PAD is ALS, and the target protein is SOD1.

In some embodiments, there is provided a method for determining a risk for Alzheimer's disease (AD) in an individual, comprising: a) contacting a serum sample from the individual with a substrate peptide immobilized on a solid support under conditions that allow formation of a catabody-substrate peptide complex, wherein the substrate peptide comprises the amino acid sequence of SEQ ID NO: 3; b) determining the amount of the catabody-substrate peptide complex using an antibody that specifically binds to total Ig (e.g., total human Ig, such as total IgM, total IgG, total IgA, and/or total IgE), thereby providing the level of one or more SHD catabodies in the serum of the individual; c) contacting a serum sample of the individual with Aβ (e.g., Aβ(1-42)) under conditions that allow formation of an auto-antibody-Aβ complex, and d) determining the amount of the auto-antibody-Aβ complex, thereby providing the level of the auto-antibody against Aβ; and wherein the individual is determined as having a risk for the AD if: (i) the level of the one or more SHD catabodies is lower than a control SHD catabody level; and (ii) the level of the auto-antibody against Aβ is lower than a control auto-antibody level. In some embodiments, the antibody specifically binding to Ig is labeled with an enzyme (e.g., HRP) or a fluorescent label (e.g., FITC). In some embodiments, the solid support is an ELISA plate. In some embodiments, the level of the auto-antibody is determined using an ELISA assay.

In some embodiments, there is provided a method for determining a risk for Alzheimer's disease (AD) in an individual, comprising: a) contacting a serum sample from the individual with a substrate peptide immobilized on a solid support under conditions that allow formation of a catabody-substrate peptide complex, wherein the substrate peptide comprises the amino acid sequence of SEQ ID NO: 3; b) determining the amount of the catabody-substrate peptide complex using an antibody that specifically binds to total Ig (e.g., total human Ig, such as total IgM, total IgG, total IgA, and/or total IgE), thereby providing the level of one or more SHD catabodies in the serum of the individual, c) contacting a cerebrospinal fluid sample of the individual with an anti-Aβ antibody under conditions that allow formation of an antibody-Aβ complex, and d) determining the amount of the antibody-Aβ complex, thereby providing the level of Aβ; and wherein the individual is determined as having a risk for the AD if: (i) the level of the one or more SHD catabodies is lower than a control SHD catabody level; and (ii) the level of Aβ is higher than a control Aβ level. In some embodiments, the antibody specifically binding to Ig is labeled with an enzyme (e.g., HRP) or a fluorescent label (e.g., FITC). In some embodiments, the solid support is an ELISA plate. In some embodiments, the level of Aβ is determined using an ELISA assay.

Any one of the diagnosis methods described herein may be used to inform treatment of the PAD using any known therapeutic agents for treating the PAD in the art, or any catabodies (such as anti-Aβ catabodies) described herein. The diagnosis methods described herein allow early detection of a risk of PAD in an individual, thereby allowing early intervention and prophylactic treatment of the PAD.

Thus, in some embodiments, there is provided a method of treating or preventing a PAD in an individual, wherein the PAD is associated with aggregation of a target protein, comprising: a) determining the individual as having a risk for the PAD according to any one of the methods of determining a risk as described herein; and b) administering to the individual an effective amount of a therapeutic agent that treats the PAD.

In some embodiments, there is provided a method of treating or preventing a PAD in an individual, wherein the PAD is associated with aggregation of a target protein, comprising: a) determining the individual as having a risk for the PAD according to any one of the methods of determining a risk as described herein; and b) administering to the individual an effective amount of a therapeutic catabody that specifically binds to the target protein. In some embodiments, the method is repeated at a frequency of no more than about every three months, e.g., about every three months, about every six months, or about every year. In some embodiments, the method is carried out only once.

In some embodiments, there is provided a method of treating or preventing AD in an individual, comprising: a) determining the individual as having a risk for AD according to any one of the methods of determining a risk as described herein; and b) administering to the individual an effective amount of an anti-Aβ catabody, such as any one of the anti-Aβ catabodies described in Section III. In some embodiments, the method is repeated at a frequency of no more than about every three months, e.g., about every three months, about every six months, or about every year.

In some embodiments, there is provided a method of treating or preventing a PAD in an individual, wherein the PAD is associated with aggregation of a target protein, comprising: a) determining the level of one or more SHD catabodies in a biological sample (e.g., serum sample) of the individual, wherein the individual is determined as having a risk for the PAD if the level of the one or more SHD catabodies is lower than a control SHD catabody level; and b) administering to the individual an effective amount of a therapeutic catabody that specifically binds to the target protein. In some embodiments, the level of one or more SHD catabodies is the level of one or more SHD catabodies that specifically bind to the target protein. In some embodiments, the level of one or more SHD catabodies is the level of total SHD catabodies. In some embodiments, the level of total SHD catabodies is determined by contacting a serum sample of the individual with a substrate peptide under conditions that allow formation of a catabody-substrate peptide complex, and determining the amount of the catabody-substrate peptide complex. In some embodiments, the substrate peptide is immobilized on a solid support. In some embodiments, (i) the PAD is Alzheimer's disease, and the target protein is Aβ; (ii) the PAD is Parkinson's disease, and the target protein is α-synuclein; (iii) the PAD is Alzheimer's disease or dementia, and the target protein is Tau; (iv) the PAD is ATTR amyloidosis, and the target protein is transthyretin; (v) the PAD is AL amyloidosis, and the target protein is immunoglobulin light chain; (vi) the PAD is FTLD or ALS, and the target protein is TDP43; (vii) the PAD is Huntington's disease, and the target protein is Huntingtin; (viii) the PAD is Type II diabetes, and the target protein is IAPP; and (ix) the PAD is ALS, and the target protein is SOD1. In some embodiments, the method is repeated at a frequency of no more than about every three months, e.g., about every three months, about every six months, or about every year.

In some embodiments, there is provided a method of treating or preventing AD in an individual, comprising: a) contacting a serum sample from the individual with a substrate peptide immobilized on a solid support under conditions that allow formation of a catabody-substrate peptide complex, and b) determining the amount of one or more SHD catabodies that specifically bind to Aβ, and c) administering to the individual an effective amount of an anti-Aβ catabody, if the level of the one or more SHD catabodies is lower than a control SHD catabody level. In some embodiments, the method is repeated at a frequency of no more than about every three months, e.g., about every three months, about every six months, or about every year.

In some embodiments, there is provided a method of treating or preventing a PAD in an individual, wherein the PAD is associated with aggregation of a target protein, comprising: a) determining the level of one or more SHD catabodies in a biological sample (e.g., serum sample) of the individual, b) determining the level of an auto-antibody against the target protein a biological sample (e.g., serum sample) of the individual, and c) administering to the individual an effective amount of a therapeutic catabody that specifically binds to the target protein if: (i) the level of the one or more SHD catabodies is lower than a control SHD catabody level; and (ii) the level of the auto-antibody against the target protein is lower than a control auto-antibody level. In some embodiments, the level of one or more SHD catabodies is the level of one or more SHD catabodies that specifically bind to the target protein. In some embodiments, the level of one or more SHD catabodies is the level of total SHD catabodies. In some embodiments, the level of total catabodies is determined by contacting a serum sample of the individual with a substrate peptide under conditions that allow formation of a catabody-substrate peptide complex, and determining the amount of the catabody-substrate peptide complex. In some embodiments, the substrate peptide is immobilized on a solid support. In some embodiments, the level of the auto-antibody is determined by contacting a serum sample of the individual with the target protein under conditions that allow formation of an auto-antibody-target protein complex, and determining the amount of the auto-antibody-target protein complex. In some embodiments, the level of the auto-antibody is determined using an ELISA assay. In some embodiments, (i) the PAD is Alzheimer's disease, and the target protein is Aβ; (ii) the PAD is Parkinson's disease, and the target protein is α-synuclein; (iii) the PAD is Alzheimer's disease or dementia, and the target protein is Tau; (iv) the PAD is ATTR amyloidosis, and the target protein is transthyretin; (v) the PAD is AL amyloidosis, and the target protein is immunoglobulin light chain; (vi) the PAD is FTLD or ALS, and the target protein is TDP43; (vii) the PAD is Huntington's disease, and the target protein is Huntingtin; (viii) the PAD is Type II diabetes, and the target protein is IAPP; and (ix) the PAD is ALS, and the target protein is SOD1. In some embodiments, the method is repeated at a frequency of no more than about every three months, e.g., about every three months, about every six months, or about every year.

In some embodiments, there is provided a method of treating or preventing a PAD in an individual, wherein the PAD is associated with aggregation of a target protein, comprising: a) contacting a serum sample of the individual with a substrate peptide immobilized on a solid support under conditions that allow formation of a catabody-substrate peptide complex, wherein the substrate peptide comprises the amino acid sequence (EAR)$_n$ (SEQ ID NO: 2), wherein n is an integer between 1 and 30 (e.g., n is 3); b) determining the amount of the catabody-substrate peptide complex, thereby providing the level of one or more SHD catabodies in the serum of the individual; c) determining the level of an auto-antibody against the target protein in a biological sample (e.g., serum sample) of the individual, and d) administering to the individual an effective amount of a therapeutic catabody that specifically binds to the target protein if: (i) the level of the one or more SHD catabodies is lower than a control SHD catabody level; and (ii) the level of the auto-antibody against the target protein is lower than a control auto-antibody level. In some embodiments, the amount of the catabody-substrate peptide complex is determined using an antibody that specifically binds to total Ig (e.g., total human Ig, such as total IgM, total IgG, total IgA, and/or total IgE). In some embodiments, the antibody specifically binding to Ig is labeled with an enzyme (e.g., HRP) or a fluorescent label (e.g., FITC). In some embodiments, the solid support is an ELISA plate. In some embodiments, the level of the auto-antibody is determined by contacting a serum sample of the individual with the target protein under conditions that allow formation of an auto-antibody-target protein complex, and determining the amount of the auto-antibody-target protein complex. In some embodiments, the level of the auto-antibody is determined using an ELISA assay. In some embodiments, (i) the PAD is Alzheimer's disease, and the target protein is Aβ; (ii) the PAD is Parkinson's disease, and the target protein is α-synuclein; (iii) the PAD is Alzheimer's disease or dementia, and the target protein is Tau; (iv) the PAD is ATTR amyloidosis, and the target protein is transthyretin; (v) the PAD is AL amyloidosis, and the target protein is immunoglobulin light chain; (vi) the PAD is FTLD or ALS, and the target protein is TDP43; (vii) the PAD is Huntington's disease, and the target protein is Huntingtin; (viii) the PAD is Type II diabetes, and the target protein is IAPP; and (ix) the PAD is ALS, and the target protein is SOD1. In some embodiments, the method is repeated at a frequency of no more than about every three months, e.g., about every three months, about every six months, or about every year.

In some embodiments, there is provided a method of treating or preventing Alzheimer's disease (AD) in an individual, comprising: a) contacting a serum sample from the individual with a substrate peptide immobilized on a solid support under conditions that allow formation of a catabody-substrate peptide complex, wherein the substrate peptide comprises the amino acid sequence of SEQ ID NO: 3; b) determining the amount of the catabody-substrate peptide complex using an antibody that specifically binds to total Ig (e.g., total human Ig, such as total IgM, total IgG, total IgA, and/or total IgE), thereby providing the level of one or more SHD catabodies in the serum of the individual, c) contacting a serum sample of the individual with Aβ (e.g., Aβ(1-42)) under conditions that allow formation of an auto-antibody-Aβ complex, d) determining the amount of the auto-antibody-Aβ complex using an antibody that specifically binds to total Ig (e.g., total human Ig, such as total IgM, total IgG, total IgA, and/or total IgE), thereby providing the level of the auto-antibody against Aβ; and e) administering to the individual an effective amount of an anti-Aβ catabody, if: (i) the level of the one or more SHD catabodies is lower than a control SHD catabody level; and (ii) the level of the auto-antibody against Aβ is lower than a control auto-antibody level. In some embodiments, the antibody specifically binding to Ig is labeled with an enzyme (e.g., HRP) or a fluorescent label (e.g., FITC). In some embodiments, the solid support is an ELISA plate. In some embodiments, the method is repeated at a frequency of no more than about every three months, e.g., about every three months, about every six months, or about every year.

In some embodiments, there is provided a method of treating or preventing Alzheimer's disease (AD) in an individual, comprising: a) determining the level of one or more SHD catabodies in a biological sample (e.g., serum sample)

of the individual, b) determining the level of an auto-antibody against Aβ in a biological sample (e.g., serum sample) of the individual, and c) administering to the individual an effective amount of an anti-Aβ catabody, if: (i) the level of the one or more SHD catabodies is lower than a control SHD catabody level; and (ii) the level of the auto-antibody against Aβ is lower than a control auto-antibody level, wherein the anti-Aβ catabody comprises: a light chain variable region ($V_L$) comprising a light chain complementarity determining region (LC-CDR) 1 comprising the amino acid sequence of SEQ ID NO: 12, an LC-CDR2 comprising the amino acid sequence of SEQ ID NO: 13, and an LC-CDR3 comprising the amino acid sequence of SEQ ID NO: 14, or a variant thereof comprising up to about 5 amino acid substitutions in the LC-CDRs, wherein the amino acid residue at position 1 of the $V_L$ is D, the amino acid residue at position 27A of the $V_L$ is S, and the amino acid residue at position 93 of the $V_L$ is H, and wherein the numbering is according to the EU index of Kabat. In some embodiments, the anti-Aβ catabody comprises: a heavy chain variable region ($V_H$) comprising a heavy chain complementarity determining region (HC-CDR) 1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11, or a variant thereof comprising up to about 5 amino acid substitutions in the HC-CDRs. In some embodiments, the amino acid residue at position 26 of the $V_L$ is S, the amino acid residue at position 27D of the $V_L$ is D, E or H, and/or the amino acid residue at position 28 of the $V_L$ is D or N, and wherein the numbering is according to the EU index of Kabat. In some embodiments, the anti-Aβ catabody comprises: a $V_H$ comprising an amino acid sequence having at least about 85% sequence identity to the amino acid sequence of SEQ ID NO: 4, 6, 19 or 20; and/or a $V_L$ comprising an amino acid sequence having at least about 85% sequence identity to the amino acid sequence of SEQ ID NO: 5, 7, 8, 21 or 22. In some embodiments, the anti-Aβ catabody comprises: (i) a $V_H$ comprising the amino acid sequence of SEQ ID NO: 4, and a $V_L$ comprising the amino acid sequence of SEQ ID NO: 5; (ii) a $V_H$ comprising the amino acid sequence of SEQ ID NO: 6, and a $V_L$ comprising the amino acid sequence of SEQ ID NO: 7; (iii) a $V_H$ comprising the amino acid sequence of SEQ ID NO: 6, and a $V_L$ comprising the amino acid sequence of SEQ ID NO: 8; (iv) a $V_H$ comprising the amino acid sequence of SEQ ID NO: 19, and a $V_L$ comprising the amino acid sequence of SEQ ID NO: 21; (v) a $V_H$ comprising the amino acid sequence of SEQ ID NO: 20, and a $V_L$ comprising the amino acid sequence of SEQ ID NO: 21; (vi) a $V_H$ comprising the amino acid sequence of SEQ ID NO: 19, and a $V_L$ comprising the amino acid sequence of SEQ ID NO: 22; or (vii) a $V_H$ comprising the amino acid sequence of SEQ ID NO: 20, and a $V_L$ comprising the amino acid sequence of SEQ ID NO: 22. In some embodiments, the anti-Aβ catabody is a full-length antibody, such as an IgG1 or IgG4 antibody. In some embodiments, the method is repeated at a frequency of no more than about every three months, e.g., about every three months, about every six months, or about every year.

In some embodiments, there is provided a method of treating or preventing AD in an individual, comprising: a) contacting a serum sample from the individual with a substrate peptide immobilized on a solid support under conditions that allow formation of a catabody-substrate peptide complex, wherein the substrate peptide comprises the amino acid sequence of SEQ ID NO: 3; b) determining the amount of the catabody-substrate peptide complex using an antibody that specifically binds to total Ig (e.g., total human Ig, such as total IgM, total IgG, total IgA, and/or total IgE), thereby providing the level of one or more SHD catabodies in the serum of the individual; c) contacting a serum sample of the individual with Aβ (e.g., Aβ(1-42)) under conditions that allow formation of an auto-antibody-Aβ complex, d) determining the amount of the auto-antibody-Aβ complex using an antibody that specifically binds to total Ig (e.g., total human Ig, such as total IgM, total IgG, total IgA, and/or total IgE), thereby providing the level of the auto-antibody against Aβ; and e) administering to the individual an effective amount of an anti-Aβ catabody, if: (i) the level of the one or more SHD catabodies is lower than a control SHD catabody level; and (ii) the level of the auto-antibody against Aβ is lower than a control auto-antibody level, wherein the anti-Aβ catabody comprises: a $V_L$ comprising a light chain complementarity determining region (LC-CDR) 1 comprising the amino acid sequence of SEQ ID NO: 12, an LC-CDR2 comprising the amino acid sequence of SEQ ID NO: 13, and an LC-CDR3 comprising the amino acid sequence of SEQ ID NO: 14, or a variant thereof comprising up to about 5 amino acid substitutions in the LC-CDRs, wherein the amino acid residue at position 1 of the $V_L$ is D, the amino acid residue at position 27A of the $V_L$ is S, and the amino acid residue at position 93 of the $V_L$ is H, and wherein the numbering is according to the EU index of Kabat; and a $V_H$ comprising a HC-CDR1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11, or a variant thereof comprising up to about 5 amino acid substitutions in the HC-CDRs. In some embodiments, the amino acid residue at position 26 of the $V_L$ is S, the amino acid residue at position 27D of the $V_L$ is D, E or H, and/or the amino acid residue at position 28 of the $V_L$ is D or N. and wherein the numbering is according to the EU index of Kabat. In some embodiments, the anti-Aβ catabody comprises: a $V_H$ comprising an amino acid sequence having at least about 85% sequence identity to the amino acid sequence of SEQ ID NO: 4, 6, 19 or 20; and/or a $V_L$ comprising an amino acid sequence having at least about 85% sequence identity to the amino acid sequence of SEQ ID NO: 5, 7, 8, 21 or 22. In some embodiments, the anti-Aβ catabody comprises: (i) a $V_H$ comprising the amino acid sequence of SEQ ID NO: 4, and a $V_L$ comprising the amino acid sequence of SEQ ID NO: 5; (ii) a $V_H$ comprising the amino acid sequence of SEQ ID NO: 6, and a $V_L$ comprising the amino acid sequence of SEQ ID NO: 7; (iii) a $V_H$ comprising the amino acid sequence of SEQ ID NO: 6, and a $V_L$ comprising the amino acid sequence of SEQ ID NO: 8; (iv) a $V_H$ comprising the amino acid sequence of SEQ ID NO: 19, and a $V_L$ comprising the amino acid sequence of SEQ ID NO: 21; (v) a $V_H$ comprising the amino acid sequence of SEQ ID NO: 20, and a $V_L$ comprising the amino acid sequence of SEQ ID NO: 21; (vi) a $V_H$ comprising the amino acid sequence of SEQ ID NO: 19, and a $V_L$ comprising the amino acid sequence of SEQ ID NO: 22; or (vii) a $V_H$ comprising the amino acid sequence of SEQ ID NO: 20, and a $V_L$ comprising the amino acid sequence of SEQ ID NO: 22. In some embodiments, the anti-Aβ catabody is a full-length antibody, such as an IgG1 or IgG4 antibody. In some embodiments, the antibody specifically binding to Ig is labeled with an enzyme (e.g., HRP) or a fluorescent label (e.g., FITC). In some embodiments, the solid support is an ELISA plate. In some embodiments, the method is repeated at a frequency of no more than about every three months, e.g., about every three months, about every six months, or about every year.

The methods described herein detect the levels of one or more SHD catabodies, auto-antibodies against target proteins, and target proteins, including, but not limited to, protein levels and mRNA levels. Protein levels may be detected using immunoassays, mass spectroscopy or other molecular biology techniques. Levels of mRNA may be detected using quantitative PCR or other molecular biology techniques.

In some embodiments, the method comprises detecting the level of one or more SHD catabodies using a substrate peptide comprising the amino acid sequence of SEQ ID NO: 2. In some embodiments, the level of one or more SHD catabodies is the level of total SHD catabodies. In some embodiments, the level of one or more SHD catabodies is the level of one or more SHD catabodies that specifically bind to the target protein. In some embodiments, the level of one or more SHD catabodies specifically binding to the target protein is determined by: a) extracting (e.g., immunologically pulling down) antibodies that specifically bind to the target protein from the biological sample, and b) contacting the extracted antibodies with the substrate peptide. In some embodiments, the level of one or more SHD catabodies that specifically bind to the target protein is determined by: a) contacting the biological sample with a target protein (e.g., Aβ) immobilized on a solid support under conditions that allow formation of a catabody-target protein complex; b) contacting the catabody-target protein complex with a substrate peptide comprising a label (e.g., AMC or biotin) under conditions that allow formation of a catabody-target protein-substrate peptide complex; c) contacting the catabody-target protein-substrate peptide with an antibody against the label; and d) determining the amount of antibody against the label bound to the catabody-target protein-substrate peptide, thereby providing the level of one or more SHD catabodies that specifically bind to the target protein.

The substrate peptide or the target protein (or fragment thereof, e.g., Aβ) may be obtained by chemical synthesis. The substrate peptide or the target protein (or fragment thereof, e.g., Aβ) may be immobilized to a solid support via an immobilization moiety such as biotin, streptavidin, avidin, or a peptide tag. In some embodiments, the solid support is functionalized for conjugation with the substrate peptide. In some embodiments, the solid support is an ELISA plate. The ELISA plate may be a flat-bottomed, multi-well (e.g., 96-well) plates, made from polystyrene or polyvinyl chloride. The substrate peptide or the target protein (or fragment thereof, e.g., Aβ) may be coated onto an ELISA plate via passive adsorption. Adsorption occurs passively as the result of hydrophobic interactions between the amino acids side chains on the substrate peptides or the target protein (or fragment thereof, e.g., Aβ) and the plastic surface of the ELISA plate. In some embodiments, the substrate peptide is coated on the surface of an ELISA plate at the density of about 1-2 μg/well.

Exemplary coating conditions on an ELISA plate involve adding 50-100 μl of coating buffer, containing the substrate peptide at a concentration of 1-10 μg/ml, and incubating overnight at 4° C. or for 1-3 hours at 37° C. Alternative temperatures, times, buffers, and coating agent concentrations can be used and should be tested by experimentation. Exemplary coating buffers include bicarbonate buffer at pH 9.6 and phosphate buffer saline (PBS). In some embodiments, the solid support (e.g., ELISA plate) is washed (e.g., three times) after the substrate peptide or the target protein (or fragment thereof. e.g., Aβ) is immobilized using a wash buffer, such as PBS or PBST (0.1% TWEEN-20 in PBS). In some embodiments, the solid support (e.g., ELISA plate) is blocked with a blocking buffer, such as 10% fetal bovine serum (FBS) in PBS, or 1% BSA in PBS. In some embodiments, the solid support (e.g., ELISA plate) is washed (e.g., three times) after the blocking using a wash buffer, such as PBS or PBST.

The levels of one or more catabodies, auto-antibodies against the target protein and the target protein are determined using a sample (e.g., a sample from an individual or a reference sample). In some embodiments, the sample is a biological sample. In some embodiments, the biological sample is a biological fluid sample or a biological tissue sample. In some embodiments, the biological fluid sample is a bodily fluid, such as blood, plasma, serum, cerebrospinal fluid (CSF) or brain interstitial fluid (ISF). In some embodiments, the biological sample is a biopsy sample. In some embodiments, the biological sample is a tissue or cell sample. In some embodiments, the biological sample is a B cell sample. In some embodiments, the biological sample is a sample enriched for certain molecules, such as immunoglobulin or target protein-binding molecules, for example by immunoprecipitation.

In some embodiments, a plurality of sample is obtained during the course of the treatment, e.g., every month, every 2 months, every three months, every 4 months, every 5 months, every 6 months, or every year. In some embodiments, the sample for determining the level of one or more catabodies and the sample for determining the level of auto-antibodies or target protein are obtained from the individual at the same time, or are aliquots from the same sample. In some embodiments, the sample for determining the level of one or more catabodies and the sample for determining the level of auto-antibodies or target protein are obtained from the individual at different time and/or from different sources. In some embodiments, the same sample is used for determining the level of one or more SHD catabodies and the level of auto-antibodies against the target protein (e.g., Aβ). In some embodiments, a serum sample is used for determining the level of one or more SHD catabodies, and a CSF sample is used for determining the level of Aβ.

In some embodiments, the biological sample is a serum sample. In some embodiments, the serum sample contains at least about 1 μg/mL, such as at least about any one of 2, 5, 10, 15, 20, 25, 30, 40, 50, 60, 70, 80, 90, 100, 150, 200, 250, or more μg/mL Ig. In some embodiments, the serum sample contains at least about 100 μg/mL Ig. In some embodiments, the serum sample contains no more than about any one of 500, 400, 300, 250, 200, or 150 μg/mL Ig.

In some embodiments, the biological sample is incubated with the substrate peptide or the target protein (or fragment thereof. e.g., Aβ) for about 1 hour to about 16 hours, including, for example, about any one of 1, 2, 3, 4, 5, 6, 7, 8, 9, 10, 11, 12, 13, 14, 15, or 16 hours. In some embodiments, the biological sample is incubated with the substrate peptide or the target protein (or fragment thereof, e.g., Aβ) for at least about any one of 1, 2, 3, 4, 5, 6, 7, 8, 9, 10, 11, 12, 13, 14, 15, or 16 hours. In some embodiments, the biological sample is incubated with the substrate peptide or the target protein (or fragment thereof, e.g., Aβ) for no more than about any one of 16, 15, 14, 13, 12, 11, 10, 9, 8, 7, 6, 5, 4, 3, 2, or 1 hour(s). In some embodiments, the biological sample is incubated with the substrate peptide or the target protein (or fragment thereof. e.g., Aβ) for about 1 hour to about 3 hours. In some embodiments, the biological sample is incubated with the substrate peptide or the target protein (or fragment thereof, e.g., Aβ) overnight. In some embodiments, the incubation is carried out at room temperature. In some embodiments, the incubation is carried out at 4° C.

In some embodiments, after the biological sample is incubated with the substrate peptide or the target protein (or fragment thereof, e.g., Aβ), the solid support (e.g., ELISA plate) is washed (e.g., three times) with a wash buffer, such as PBS or PBST. In some embodiments, the solid support (e.g., ELISA plate) is blocked with a blocking buffer, such as 10% fetal bovine serum (FBS) in PBS, or 1% BSA in PBS. In some embodiments, the solid support (e.g., ELISA plate) is washed (e.g., three times) after the blocking using a wash buffer, such as PBS or PBST.

The amount of the catabody-substrate peptide complex or the auto-antibody-target protein complex can be detected using an antibody that specifically binds to species-specific immunoglobulin molecules, such as human Ig. In some embodiments, the antibody specifically binds to total IgM, total IgG, total IgA, and/or total IgE. Exemplary antibodies specifically binding to human Ig include, but are not limited to, goat anti-human Ig. The antibody that specifically binds to Ig may be labeled with an enzyme (e.g., HRP) for detection using enhanced chemo-luminescence (ECL) substrates. Alternatively, the antibody that specifically binds to Ig may be labeled with a fluorescent label, e.g., FITC, for direct detection. A plate reader may be used to detect the ECL signal or the fluorescence signal using suitable excitation, emission and cutoff wavelength settings.

Other methods for determining the level of one or more auto-antibodies against Aβ are known in the art, and such methods can be used in any one of the methods of diagnosis, treatment or prevention of AD described herein. See, for example, Weksler M E, et al. "Patients with Alzheimer disease have lower levels of serum anti-amyloid peptide antibodies than healthy elderly individuals." *Exp Gerontol.* 37:943-948 (2002); Mruthinti S, et al. "Autoimmunity in Alzheimer's disease: increased levels of circulating IgGs binding Abeta and RAGE peptides." *Neurobiol. Aging,* 25:1023-1032 (2004); Kellner A., et al. "Autoantibodies against beta-amyloid are common in Alzheimer's disease and help control plaque burden," *Ann. Neurol.* 65:24-31 (2009); Britschgi M, Olin C E, Johns H T, Takeda-Uchimura Y, et al. "Neuroprotective natural antibodies to assemblies of amyloidogenic peptides decrease with normal aging and advancing Alzheimer's disease," *Proc. Natl. Acad. Sci. USA.* 106:12145-12150 (2009), which are incorporated herein by reference. In some embodiments, the level of one or more auto-antibodies against the target protein (e.g., Aβ) is determined using an ELISA assay.

The level of the target protein (e.g., Aβ) in a biological sample (e.g., serum sample or cerebrospinal sample) can be determined using an ELISA assay or a liquid chromatography/tandem mass spectrometry assay.

In some embodiments, the level of one or more SHD catabodies is compared to a control SHD catabody level. In some embodiments, the level of one or more SHD catabodies is compared to the level of one or more SHD catabodies in a control sample. In some embodiments, the level of one or more SHD catabodies is compared to the level of one or more SHD catabodies in a plurality of control samples. In some embodiments, the plurality of control samples is used to generate a statistical distribution that is used to classify or rank the levels of one or more SHD catabodies in individuals of the same age or the same age group.

In some embodiments, the level of an auto-antibody against a target protein (e.g., Aβ) is compared to a control auto-antibody level. In some embodiments, the level of an auto-antibody against a target protein (e.g., Aβ) is compared to the level of the auto-antibody against the target protein (e.g., Aβ) in a control sample. In some embodiments, the level of an auto-antibody against a target protein (e.g., Aβ) is compared to the level of the auto-antibody against the target protein (e.g., Aβ) in a plurality of control samples. In some embodiments, the plurality of control samples are used to generate a statistical distribution that is used to classify or rank the levels of the auto-antibody against the target protein (e.g., Aβ) in a certain population of individuals, such as healthy individuals, individuals having a PAD (e.g., AD), or individuals of the same age or the same age group.

In some embodiments, the level of the target protein (e.g., Aβ) is compared to a control target protein level. In some embodiments, the level of the target protein (e.g., Aβ) is compared to the level of the target protein (e.g., Aβ) in a control sample. In some embodiments, the level of the target protein (e.g., Aβ) is compared to the level of the target protein (e.g., Aβ) in a plurality of control samples. In some embodiments, the plurality of control samples are used to generate a statistical distribution that is used to classify or rank the levels of the target protein (e.g., Aβ) in a certain population of individuals, such as healthy individuals, individuals having a PAD (e.g., AD), or individuals of the same age or the same age group.

Exemplary age groups include, but are not limited to, 18-30 years old, 30-40 years old, 40-50 years old, 50-60 years old, 60-70 years old, 70-80 years old, 80-90 years old, 18-40 years old, 40-90 years old, 18-60 years old, 60-90 years old, 60 years or older, 70 years or older, 75 years or older, 80 years or older, 85 years or older, or 90 years or older.

Control samples can be obtained using the same methods as non-control samples. In some embodiments, the control sample is obtained from a different individual, such as a healthy individual or an individual not having a PAD, and/or an individual sharing similar ethnic, age, and gender. In some embodiments, a plurality of control samples (for example from different individuals) is used to determine a range of levels of one or more SHD catabodies, auto-antibodies against the target protein (e.g., Aβ), or the target protein (e.g., Aβ).

In some embodiments, the control SHD catabody level is the level of one or more SHD catabodies in a healthy individual. In some embodiments, the control SHD catabody level is the average or median level of one or more SHD catabodies in a population of individuals, e.g., individuals of the same age group, or individuals of about 18 years old to about 50 years old (e.g., about 18 years old to about 40 years old, or about 18 years old to about 30 years old). In some embodiments, the control auto-antibody level is the level of the auto-antibody against the target protein (e.g., Aβ) in a healthy individual. In some embodiments, the control auto-antibody level is the median level of the auto-antibody against the target protein in a population of individuals, e.g., individuals of the same age group. In some embodiments, the control target protein level is the level of the target protein (e.g., Aβ) in a healthy individual. In some embodiments, the control target protein level is the median level of the target protein in a population of individuals, e.g., individuals of the same age group.

In some embodiments, the level of the one or more SHD catabodies, auto-antibodies against the target protein (e.g., Aβ), or the target protein (e.g., Aβ) is compared to a control or reference (e.g., the median or average level for a population of individuals or level of a healthy individual). In some embodiments, the control level is a pre-determined threshold level. For example, if the level of one or more SHD catabodies for an individual is determined to be no more than about any one of 90%, 80%, 75%, 70%, 60%, 50%, 40%, 30%, 20%, 10% or lower of the median level of a population of individuals in the same age or the same age group, that individual is determined to have a low level of the one or more SHD catabodies. Alternatively, if the level of the one or more SHD catabodies for an individual is determined to be more than about any one of 20%, 50%, 75%, 2×, 3×, 5×, 10× or more than the median level of a population of individuals in the same age group, that individual is determined to have a high level of the one or more SHD catabodies.

If the level of one or more auto-antibodies against the target protein (e.g., Aβ) for an individual is determined to be no more than about any one of 90%, 80%, 75%, 70%, 60%, 50%, 40%, 30%, 20%, 10% or lower of the median level of a population of individuals in the same age group, that individual is determined to have a low level of the one or more auto-antibodies against the target protein (e.g., Aβ). Alternatively, if the level of the one or more auto-antibodies against the target protein (e.g., Aβ) for an individual is determined to be more than about any one of 20%, 50%, 75%, 2×, 3×, 5×, 10× or more than the median level of a population of individuals in the same age group, that individual is determined to have a high level of the one or more auto-antibodies against the target protein (e.g., Aβ).

If the level of the target protein (e.g., Aβ) for an individual is determined to be no more than about any one of 90%, 80%, 75%, 70%, 60%, 50%, 40%, 30%, 20%, 10% or lower of the median level of a population of individuals in the same age group, that individual is determined to have a low level of the target protein (e.g., Aβ). Alternatively, if the level of the target protein (e.g., Aβ) for an individual is determined to be more than about any one of 20%, 50%, 75%, 2×, 3×, 5×, 10× or more than the median level of a population of individuals in the same age group, that individual is determined to have a high level of the target protein (e.g., Aβ).

In some embodiments, an individual is determined as having a risk for a PAD (e.g., AD) if: (i) the level of the one or more SHD catabodies is lower than a control SHD catabody level; and (ii) the level of the auto-antibody against the target protein (e.g., Aβ) is lower than a control auto-antibody level. In some embodiments, the level of the one or more SHD catabodies in an individual having a risk for a PAD (e.g., AD) is no more than about any one of 90%, 80%, 75%, 70%, 60%, 50%, 40%, 30%, 20%, 10% or lower of the median of a population of individuals in the same age group. In some embodiments, the level of the auto-antibody against the target protein (e.g., Aβ) in an individual having a risk for a PAD (e.g., AD) is no more than about any one of 90%, 80%, 75%, 70%, 60%, 50%, 40%, 30%, 20%, 10% or lower of the median of a population of individuals in the same age group.

In some embodiments, an individual is determined as having a risk for a PAD (e.g., AD) if: (i) the level of the one or more SHD catabodies is lower than a control SHD catabody level; and (ii) the level of the target protein (e.g., Aβ) is higher than a control target protein level. In some embodiments, the level of the one or more SHD catabodies in an individual having a risk for a PAD (e.g., AD) is no more than about any one of 90%, 80%, 75%, 70%, 60%, 50%, 40%, 30%, 20%, 10% or lower of the median of a population of individuals in the same age group. In some embodiments, the level of the target protein (e.g., Aβ) in an individual having a risk for a PAD (e.g., AD) is more than about any one of 20%, 50%, 75%, 2×, 3×, 5×, 10× or more of the median of a population of individuals in the same age group.

The methods of diagnosis and treatment described herein can be applied to individuals having a PAD or a risk of PAD. In some embodiments, the individual is a mammal and includes, but is not limited to, human, bovine, horse, feline, canine, rodent (mouse, rat or hamster), or non-human primate. In some embodiments, the individual is a human. In some embodiments, the individual is a young human individual, such as a human individual no more than about any one of 60, 50, 40, 30, or 25 years old. In some embodiments, the individual is an old human individual, such as a human individual older than about any one of 50, 60, 70, or 80 years old. As used herein, an "at risk" individual is an individual who is at risk of developing a PAD (e.g., AD). An individual "at risk" may or may not have detectable disease, and may or may not have displayed detectable disease prior to the treatment methods described herein. "At risk" denotes that an individual has one or more so-called risk factors, which are measurable parameters that correlate with development of a PAD (e.g., AD), which are described herein. An individual having one or more of these risk factors has a higher probability of developing a PAD (e.g., AD) than an individual without these risk factor(s).

Many PADs are known in the art and can be diagnosed, treated or prevented with the methods described herein. Exemplary PADs include, but are not limited to, Alzheimer's disease associated with accumulation of Aβ; Parkinson's disease associated with accumulation of α-synuclein; Alzheimer's disease or dementia associated with accumulation of Tau; ATTR amyloidosis associated with accumulation of transthyretin; AL amyloidosis associated with accumulation of immunoglobulin light chain: ubiquitin-positive neuronal and glial inclusions (such as FTLD or ALS) associated with accumulation of TDP43 (TAR DNA-binding protein of 43 kDa); Huntington's disease associated with accumulation of Huntingtin; Type II diabetes associated with accumulation of IAPP; and ALS associated with accumulation of SOD1.

An therapeutic catabody that specifically bind to and cleave the target protein (e.g., Aβ) can be administered to the individual if the individual is determined as having a PAD or having a risk of PAD, for example, if: (i) the level of the one or more SHD catabodies is lower than a control SHD catabody level; and (ii) the level of the auto-antibody against the target protein (e.g., Aβ) is lower than a control auto-antibody level, or the level of the target protein (e.g., Aβ) is higher than a control target protein level. The therapeutic catabody may be administered to the individual using any suitable dosage (including dosage amount and dosing schedule/frequency) and routes of administration. The dosage (or effective amount of the therapeutic catabody) may be determined according to the size and condition of the individual, and according to standard therapeutic practice. The route of administration is in accordance with known and accepted methods, such as by single or multiple bolus or infusion over a period of time in a suitable manner, e.g., injection or infusion by subcutaneous, intravenous, intraperitoneal, intramuscular, intra-arterial, intralesional, intraarticular, or oral routes. Animal experiments provide reliable guidance for the determination of effective doses for human diagnostic applications. Interspecies scaling of effective doses can be performed following the principles laid down by Mordenti. J. and Chappell, W. "Me Use of Interspecies Scaling in Toxicokinetics," In *Toxicokinetics and New Drug Development*, Yacobi et al., Eds, Pergamon Press, New York 1989, pp. 4246.

In some embodiments, the effective amount of a therapeutic catabody (e.g., an anti-Aβ catabody) is about 1 µg/m² to about 100 mg/m², or about 1 µg/kg to about 100 mg/kg. In some embodiments, the dosing frequency for the administration of the therapeutic catabody (e.g., anti-Aβ catabody) is from daily to about once every three months. In some embodiments, the administration of the therapeutic catabody can be extended over an extended period of time, such as from about a month up to years.

In some embodiments, the level of one or more SHD catabodies, auto-antibodies against the target protein (e.g., Aβ) and/or the target protein (e.g., Aβ) is assessed periodically to adjust the dosage and dosing frequency of the therapeutic catabody. In some embodiments, the level of one or more SHD catabodies, auto-antibodies against the target protein (e.g., Aβ) and/or the target protein (e.g., Aβ) is assessed about every month, every 2 months, every 3 months, every 4 months, every 6 months, or every year. In some embodiments, administration of the therapeutic catabody (e.g., anti-Aβ catabody) is repeated if: (i) the level of the one or more catabodies is lower than a control catabody level; and (ii) the level of the auto-antibody against the target protein (e.g., Aβ) is lower than a control auto-antibody level, or the level of the target protein (e.g., Aβ) is higher than a control target protein level.

III. Anti-Aβ Catabodies

The present application provides therapeutic catabodies that specifically bind and cleavage a target protein associated with a PAD. The methods of treatment described in Section II may use any one of the therapeutic catabodies (e.g., anti-Aβ catabodies) described in this section. In some embodiments, the therapeutic catabody cleaves a substrate having the formula EAR-AMC (SEQ ID NO: 1). In some embodiments, the therapeutic catabody is a catabody having an SHD motif in the light chain variable region ($V_L$).

In some embodiments, there is provided a catabody specifically bind and cleave amyloid beta (Aβ) peptides. In some embodiments, the anti-Aβ catabody cleaves a substrate having the formula EAR-AMC (SEQ ID NO: 1). In some embodiments, the anti-Aβ catabody comprises an SHD motif in the light chain variable region ($V_L$).

In some embodiments, there is provided an isolated anti-Aβ catabody derived from 3D6. In some embodiments, the $V_L$ of the anti-Aβ catabody is derived from 3D6, wherein the amino acid at position 1 of the $V_L$ is an Asp (D), and wherein the numbering is according to the EU index of Kabat. In some embodiments, the amino acid residue at position 26 of the $V_L$ is Ser (S), the amino acid residue at position 27D of the $V_L$ is D, Glu (E) or His (H), and/or the amino acid residue at position 28 of the $V_L$ is D or Gln (N), and wherein the numbering is according to the EU index of Kabat. In some embodiments, the heavy chain variable region ($V_H$) of the anti-Aβ catabody is derived from 3D6. In some embodiments, the $V_H$ of the anti-Aβ catabody is screened from a phage library with human germline $V_H$ sequences based on binding affinity to Aβ. In some embodiments, the anti-Aβ catabody specifically binds to Aβ competitively with 3D6.

In some embodiments, there is provided an isolated anti-Aβ catabody comprising: a $V_L$ comprising one, two, or three LC-CDRs of 3D6, wherein the amino acid residue at position 1 of the $V_L$ is D, the amino acid residue at position 27A of the $V_L$ is S, and the amino acid residue at position 93 of the $V_L$ is H, and wherein the numbering is according to the EU index of Kabat. In some embodiments, there is provided an isolated anti-Aβ catabody comprising: a $V_L$ comprising a LC-CDR1, LC-CDR2, and LC-CDR3 of 3D6, wherein the amino acid residue at position 1 of the $V_L$ is D, the amino acid residue at position 27A of the $V_L$ is S, and the amino acid residue at position 93 of the $V_L$ is H, and wherein the numbering is according to the EU index of Kabat. In some embodiments, the amino acid residue at position 26 of the $V_L$ is Ser (S), the amino acid residue at position 27D of the $V_L$ is D, E or H, and/or the amino acid residue at position 28 of the $V_L$ is D or N, and wherein the numbering is according to the EU index of Kabat. In some embodiments, the anti-Aβ catabody comprises a $V_H$ comprising one, two, or three HC-CDRs of 3D6. In some embodiments, the anti-Aβ catabody comprises HC-CDR1, HC-CDR2, and HC-CDR3 of 3D6. In some embodiments, the $V_H$ of the anti-Aβ catabody is screened from a phage library with human germline $V_H$ sequences based on binding affinity to Aβ.

In some embodiments, there is provided an isolated anti-Aβ catabody comprising: a $V_L$ comprising a LC-CDR1 comprising the amino acid sequence of SEQ ID NO: 12, LC-CDR2 comprising the amino acid sequence of SEQ ID NO: 13, and an LC-CDR3 comprising the amino acid sequence of SEQ ID NO: 14, or a variant thereof comprising up to about 5 (e.g., 1, 2, 3, 4, or 5) amino acid substitutions in the LC-CDRs, wherein the amino acid residue at position 1 of the $V_L$ is D, the amino acid residue at position 27A of the $V_L$ is S, and the amino acid residue at position 93 of the $V_L$ is H. and wherein the numbering is according to the EU index of Kabat. In some embodiments, the amino acid residue at position 26 of the $V_L$ is Ser (S), the amino acid residue at position 27D of the $V_L$ is D. E or H, and/or the amino acid residue at position 28 of the $V_L$ is D or N, and wherein the numbering is according to the EU index of Kabat. In some embodiments, the anti-Aβ catabody comprises a $V_H$ comprising an HC-CDR1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11, or a variant thereof comprising up to about 5 (e.g., 1, 2, 3, 4, or 5) amino acid substitutions in the HC-CDRs. In some embodiments, the $V_H$ of the anti-Aβ catabody is screened from a phage library with human germline $V_H$ sequences based on binding affinity to Aβ.

In some embodiments, there is provided an isolated anti-Aβ catabody comprising: a $V_L$ comprising a LC-CDR1 comprising the amino acid sequence of SEQ ID NO: 12, LC-CDR2 comprising the amino acid sequence of SEQ ID NO: 13, and an LC-CDR3 comprising the amino acid sequence of SEQ ID NO: 14, wherein the amino acid residue at position 1 of the $V_L$ is D, the amino acid residue at position 27A of the $V_L$ is S, and the amino acid residue at position 93 of the $V_L$ is H, and wherein the numbering is according to the EU index of Kabat. In some embodiments, the amino acid residue at position 26 of the $V_L$ is Ser (S), the amino acid residue at position 27D of the $V_L$ is D, E or H, and/or the amino acid residue at position 28 of the $V_L$ is D or N, and wherein the numbering is according to the EU index of Kabat. In some embodiments, the anti-Aβ catabody comprises a $V_H$ comprising an HC-CDR1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11. In some embodiments, the $V_H$ of the anti-Aβ catabody is screened from a phage library with human germline $V_H$ sequences based on binding affinity to Aβ.

In some embodiments, there is provided an isolated anti-Aβ catabody comprising: a $V_L$ comprising a LC-CDR1 comprising the amino acid sequence of SEQ ID NO: 12, LC-CDR2 comprising the amino acid sequence of SEQ ID NO: 13, and an LC-CDR3 comprising the amino acid sequence of SEQ ID NO: 14, wherein the amino acid residue at position 1 of the $V_L$ is D, the amino acid residue at position 27A of the $V_L$ is S, and the amino acid residue at position 93 of the $V_L$ is H, and wherein the numbering is according to the EU index of Kabat; and a $V_H$ comprising an HC-CDR1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11. In some embodiments, the amino acid residue at position 26 of the $V_L$ is Ser (S), the amino acid residue at position 27D of the $V_L$ is D, E or H, and/or the amino acid residue at position 28 of the $V_L$ is D or N, and wherein the numbering is according to the EU index of Kabat.

In some embodiments, there is provided an isolated anti-Aβ catabody comprising: a $V_L$ comprising a LC-CDR1 comprising the amino acid sequence of SEQ ID NO: 12, LC-CDR2 comprising the amino acid sequence of SEQ ID NO: 13, and an LC-CDR3 comprising the amino acid sequence of SEQ ID NO: 14, wherein the amino acid residue at position 1 of the $V_L$ is D, the amino acid residue at position 27A of the $V_L$ is S, and the amino acid residue at position 93 of the $V_L$ is H, the amino acid residue at position 26 of the $V_L$ is S, the amino acid residue at position 27D of the $V_L$ is D, E or H, and/or the amino acid residue at position 28 of the $V_L$ is D or N, and wherein the numbering is according to the EU index of Kabat; and a $V_H$ comprising an HC-CDR1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11.

In some embodiments, there is provided an isolated anti-Aβ catabody comprising: a $V_L$ comprising the amino acid sequences of SEQ ID NOs: 12, 13 and 14, wherein the amino acid residue at position 1 of the $V_L$ is D, the amino acid residue at position 27A of the $V_L$ is S, and the amino acid residue at position 93 of the $V_L$ is H, and wherein the numbering is according to the EU index of Kabat. In some embodiments, the anti-Aβ catabody comprises a $V_H$ comprising the amino acid sequences of SEQ ID NOs: 9, 10 and 11. In some embodiments, the amino acid residue at position 26 of the $V_L$ is Ser (S), the amino acid residue at position 27D of the $V_L$ is D, E or H, and/or the amino acid residue at position 28 of the $V_L$ is D or N, and wherein the numbering is according to the EU index of Kabat. In some embodiments, the $V_H$ of the anti-Aβ catabody is screened from a phage library with human germline $V_H$ sequences based on binding affinity to AP.

In some embodiments, there is provided an isolated anti-Aβ catabody comprising: a $V_L$ comprising an amino acid sequence having at least about 85% (e.g., at least about any one of 85%, 86%, 87%, 88%, 89%, 90%, 91%, 92%, 93%, 94%, 95%, 96%, 97%, 98%, 99% or 100%) sequence identity to the amino acid sequence of SEQ ID NO: 5, 7 or 8, wherein the amino acid residue at position 1 of the $V_L$ is D, the amino acid residue at position 27A of the $V_L$ is S, and the amino acid residue at position 93 of the $V_L$ is H, and wherein the numbering is according to the EU index of Kabat. In some embodiments, the amino acid residue at position 26 of the $V_L$ is Ser (S), the amino acid residue at position 27D of the $V_L$ is D, E or H, and/or the amino acid residue at position 28 of the $V_L$ is D or N, and wherein the numbering is according to the EU index of Kabat. In some embodiments, the anti-Aβ catabody comprises a $V_H$ comprising an amino acid sequence having at least about 85% (e.g., at least about any one of 85%, 86%, 87%, 88%, 89%, 90%, 91%, 92%, 93%, 94%, 95%, 96%, 97%, 98%, 99% or 100%) sequence identity to the amino acid sequence of SEQ ID NO: 4 or 6. In some embodiments, the $V_H$ of the anti-Aβ catabody is screened from a phage library with human germline $V_H$ sequences based on binding affinity to Aβ.

In some embodiments, there is provided an isolated anti-Aβ catabody comprising a $V_H$ comprising the amino acid sequence of SEQ ID NO: 4, and a $V_L$ comprising the amino acid sequence of SEQ ID NO: 5. In some embodiments, there is provided an isolated anti-Aβ catabody comprising a $V_H$ comprising the amino acid sequence of SEQ ID NO: 6, and a $V_L$ comprising the amino acid sequence of SEQ ID NO: 7. In some embodiments, there is provided an isolated anti-Aβ catabody comprising a $V_H$ comprising the amino acid sequence of SEQ ID NO: 6, and a $V_L$ comprising the amino acid sequence of SEQ ID NO: 8. In some embodiments, there is provided an isolated anti-Aβ catabody comprising a $V_H$ comprising the amino acid sequence of SEQ ID NO: 6, and a $V_L$ comprising the amino acid sequence of SEQ ID NO: 21. In some embodiments, there is provided an isolated anti-Aβ catabody comprising a $V_H$ comprising the amino acid sequence of SEQ ID NO: 6, and a $V_L$ comprising the amino acid sequence of SEQ ID NO: 22. In some embodiments, there is provided an isolated anti-Aβ catabody comprising a $V_H$ comprising the amino acid sequence of SEQ ID NO: 19, and a $V_L$ comprising the amino acid sequence of SEQ ID NO: 7. In some embodiments, there is provided an isolated anti-Aβ catabody comprising a $V_H$ comprising the amino acid sequence of SEQ ID NO: 19, and a $V_L$ comprising the amino acid sequence of SEQ ID NO: 8. In some embodiments, there is provided an isolated anti-Aβ catabody comprising a $V_H$ comprising the amino acid sequence of SEQ ID NO: 19, and a $V_L$ comprising the amino acid sequence of SEQ ID NO: 21. In some embodiments, there is provided an isolated anti-Aβ catabody comprising a $V_H$ comprising the amino acid sequence of SEQ ID NO: 19, and a $V_L$ comprising the amino acid sequence of SEQ ID NO: 22. In some embodiments, there is provided an isolated anti-Aβ catabody comprising a $V_H$ comprising the amino acid sequence of SEQ ID NO: 20, and a $V_L$ comprising the amino acid sequence of SEQ ID NO: 7. In some embodiments, there is provided an isolated anti-Aβ catabody comprising a $V_H$ comprising the amino acid sequence of SEQ ID NO: 20, and a $V_L$ comprising the amino acid sequence of SEQ ID NO: 8. In some embodiments, there is provided an isolated anti-Aβ catabody comprising a $V_H$ comprising the amino acid sequence of SEQ ID NO: 20, and a $V_L$ comprising the amino acid sequence of SEQ ID NO: 21. In some embodiments, there is provided an isolated anti-Aβ catabody comprising a $V_H$ comprising the amino acid sequence of SEQ ID NO: 20, and a $V_L$ comprising the amino acid sequence of SEQ ID NO: 22.

In some embodiments, there is provided an isolated anti-Aβ catabody that specifically binds to and cleaves Aβ competitively with any one of the anti-Aβ catabodies described herein.

In some embodiments, the anti-Aβ catabody is an antigen binding fragment, such as an scFv or a Fab. In some embodiments, the anti-Aβ catabody comprises an antibody heavy chain constant region and an antibody light chain constant region. In some embodiments, the anti-Aβ catabody is a full-length antibody, such as a full-length IgG antibody. In some embodiments, the full-length anti-Aβ catabody is an IgA, IgD, IgE, IgG, or IgM antibody. In some embodiments, the full-length anti-Aβ catabody comprises IgG constant domains, such as constant domains of any of IgG1, IgG2, IgG3, and IgG4 including variants thereof. In some embodiments, the anti-Aβ catabody comprises an IgG1 heavy chain constant region. In some embodiments, the anti-Aβ catabody comprises an IgG2 heavy chain constant region. In some embodiments, the anti-Aβ catabody comprises an IgG3 heavy chain constant region. In some embodiments, the anti-Aβ catabody comprises an IgG4 heavy chain constant region. In some embodiments, the heavy chain constant region comprises or consists of the amino acid sequence of SEQ ID NO: 15. In some embodiments, the heavy chain constant region comprises or consists of the amino acid sequence of SEQ ID NO: 16. In some embodiments, the anti-Aβ catabody comprises a kappa light chain constant region. In some embodiments, the light chain constant region comprises or consists of the amino acid sequence of SEQ ID NO: 17. In some embodiments, the anti-Aβ catabody comprises a lambda light chain constant region. In some embodiments, the light chain constant region comprises or consists of the amino acid sequence of SEQ ID NO: 18. In some embodiments, the anti-Aβ catabody comprises a kappa light chain constant region.

In some embodiments, the anti-Aβ catabody comprises an Fc region. In some embodiments, the anti-Aβ catabody comprises an Fc region of a human IgG. In some embodiments, the anti-Aβ catabody comprises an Fc region with enhanced antibody dependent cellular cytotoxicity (ADCC) and/or complement dependent cytotoxicity (CDC) effector function. In some embodiments, the anti-Aβ catabody comprises an Fc region with reduced ADCC and/or CDC effector function.

In some embodiments, the anti-Aβ catabody is murine, chimeric, humanized, or human.

In some embodiments, there is provided a full-length anti-Aβ catabody comprising IgG1 constant domains, wherein the anti-Aβ catabody comprises: a $V_L$ comprising a LC-CDR1 comprising the amino acid sequence of SEQ ID NO: 12, LC-CDR2 comprising the amino acid sequence of SEQ ID NO: 13, and an LC-CDR3 comprising the amino acid sequence of SEQ ID NO: 14, or a variant thereof comprising up to about 5 (e.g., 1, 2, 3, 4, or 5) amino acid substitutions in the LC-CDRs, wherein the amino acid residue at position 1 of the $V_L$ is D, the amino acid residue at position 27A of the $V_L$ is S, and the amino acid residue at position 93 of the $V_L$ is H, and wherein the numbering is according to the EU index of Kabat. In some embodiments, the amino acid residue at position 26 of the $V_L$ is Ser (S), the amino acid residue at position 27D of the $V_L$ is D, E or H, and/or the amino acid residue at position 28 of the $V_L$ is D or N, and wherein the numbering is according to the EU index of Kabat. In some embodiments, the anti-Aβ catabody comprises a $V_H$ comprising an HC-CDR1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11, or a variant thereof comprising up to about 5 (e.g., 1, 2, 3, 4, or 5) amino acid substitutions in the HC-CDRs. In some embodiments, the $V_H$ of the anti-Aβ catabody is screened from a phage library with human germline $V_H$ sequences based on binding affinity to Aβ. In some embodiments, the anti-Aβ catabody comprises a $V_L$ comprising an amino acid sequence having at least about 85% sequence identity to the amino acid sequence of SEQ ID NO: 5, 7, 8, 21 or 22. In some embodiments, the anti-Aβ catabody comprises a $V_H$ comprising an amino acid sequence having at least about 85% sequence identity to the amino acid sequence of SEQ ID NO: 4, 6, 19 or 20. In some embodiments, the anti-Aβ catabody comprises: (i) a $V_H$ comprising the amino acid sequence of SEQ ID NO: 4, and a $V_L$ comprising the amino acid sequence of SEQ ID NO: 5; (ii) a $V_H$ comprising the amino acid sequence of SEQ ID NO: 6, and a $V_L$ comprising the amino acid sequence of SEQ ID NO: 7; (iii) a $V_H$ comprising the amino acid sequence of SEQ ID NO: 6, and a $V_L$ comprising the amino acid sequence of SEQ ID NO: 8; (iv) a $V_H$ comprising the amino acid sequence of SEQ ID NO: 19, and a $V_L$ comprising the amino acid sequence of SEQ ID NO: 21; (v) a $V_H$ comprising the amino acid sequence of SEQ ID NO: 20, and a $V_L$ comprising the amino acid sequence of SEQ ID NO: 21; (vi) a $V_H$ comprising the amino acid sequence of SEQ ID NO: 19, and a $V_L$ comprising the amino acid sequence of SEQ ID NO: 22, or (vii) a $V_H$ comprising the amino acid sequence of SEQ ID NO: 20, and a $V_L$ comprising the amino acid sequence of SEQ ID NO: 22.

In some embodiments, there is provided a full-length anti-Aβ catabody comprising IgG4 constant domains, wherein the anti-Aβ catabody comprises: a $V_L$ comprising a LC-CDR1 comprising the amino acid sequence of SEQ ID NO: 12, LC-CDR2 comprising the amino acid sequence of SEQ ID NO: 13, and an LC-CDR3 comprising the amino acid sequence of SEQ ID NO: 14, or a variant thereof comprising up to about 5 (e.g., 1, 2, 3, 4, or 5) amino acid substitutions in the LC-CDRs, wherein the amino acid residue at position 1 of the $V_L$ is D, the amino acid residue at position 27A of the $V_L$ is S, and the amino acid residue at position 93 of the $V_L$ is H, and wherein the numbering is according to the EU index of Kabat. In some embodiments, the amino acid residue at position 26 of the $V_L$ is Ser (S), the amino acid residue at position 27D of the $V_L$ is D, E or H, and/or the amino acid residue at position 28 of the $V_L$ is D or N, and wherein the numbering is according to the EU index of Kabat. In some embodiments, the anti-Aβ catabody comprises a $V_H$ comprising an HC-CDR1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11, or a variant thereof comprising up to about 5 (e.g., 1, 2, 3, 4, or 5) amino acid substitutions in the HC-CDRs. In some embodiments, the $V_H$ of the anti-Aβ catabody is screened from a phage library with human germline $V_H$ sequences based on binding affinity to Aβ. In some embodiments, the anti-Aβ catabody comprises a $V_L$ comprising an amino acid sequence having at least about 85% sequence identity to the amino acid sequence of SEQ ID NO: 5, 7, 8, 21 or 22. In some embodiments, the anti-Aβ catabody comprises a $V_H$ comprising an amino acid sequence having at least about 85% sequence identity to the amino acid sequence of SEQ ID NO: 4, 6, 19 or 20. In some embodiments, the anti-Aβ catabody comprises: (i) a $V_H$ comprising the amino acid sequence of SEQ ID NO: 4, and a $V_L$ comprising the amino acid sequence of SEQ ID NO: 5; (ii) a $V_H$ comprising the amino acid sequence of SEQ ID NO: 6, and a $V_L$ comprising the amino acid sequence of SEQ ID NO: 7; (iii) a $V_H$ comprising the amino acid sequence of SEQ ID NO: 6, and a $V_L$ comprising the amino acid sequence of SEQ ID NO: 8; (iv) a $V_H$ comprising the amino acid sequence of SEQ ID NO: 19, and a $V_L$ comprising the amino acid sequence of SEQ ID NO: 21; (v) a $V_H$ comprising the amino acid sequence of SEQ ID NO: 20, and a $V_L$ comprising the amino acid sequence of SEQ ID NO: 21; (vi) a $V_H$ comprising the amino acid sequence of SEQ ID NO: 19, and a $V_L$ comprising the amino acid sequence of SEQ ID NO: 22, or (vii) a $V_H$ comprising the amino acid sequence of SEQ ID NO: 20, and a $V_L$ comprising the amino acid sequence of SEQ ID NO: 22.

Exemplary antibody sequences are shown in Table 2 below. Those skilled in the art will recognize that many algorithms are known for prediction of CDR positions in antibody heavy chain and light chain variable regions, and catabodies comprising CDRs from catabodies described herein based on alternative prediction algorithms are within the scope of this invention. Those skilled in the art will also recognize that catabodies comprising $V_H$ or $V_L$ sequences from catabodies described herein, but based on alternative algorithms are within the scope of this invention.

TABLE 2

Exemplary anti-Aβ catabody sequences.

| SEQ ID NO | Description | Sequence |
|---|---|---|
| 4 | 3D6 $V_H$ | EVKLVESGGGLVKPGASLKLSCAASGFTFSNYGMSWVRQNSDKRLEWV ASIRSGGGRTYYSDNVKGRFTISRENAKNTLYLQMSSLKSEDTALYYCV RYDHYSGSSDYWGQGTTVTVSS |
| 5 | 3D6-D $V_L$ | DVVMTQTPLTLSVTIGQPASISCKSSQSLLDSDGKTYLNWLLQRPGQSPK RLIYLVSKLDSGVPDRFTGSGSGTDFTLKISRIEAEDLGLYYCWQGTHFPR TFGGGTKLEIKR |
| 6 | hu3D6-D $V_H$ v1 ("H1") | EVQLVESGGGLVQPGGSLRLSCAASGFTFSNYGMSWVRQAPDKRLEWV ASIRSGGGRTYYSDNVKGRFTISRDNAKNTLYLQMNSLRAEDTALYYCV RYDHYSGSSDYWGQGTLVTVSS |
| 7 | hu3D6-D $V_L$ v1 ("L1") | DVVMTQSPLSLPVTLGEPASISCKSSQSLLDSDGKTYLNWLLQRPGQSPK RLIYLVSKLDSGVPDRFSGSGSGTDFTLKISRVEAEDVGVYYCWQGTHFP RTFGGGTKLEIKR |
| 8 | hu3D6-D $V_L$ v2 ("L2") | DVVMTQSPLSLPVTLGEPASISCKSSQSLLDSDGKTYLNWLLQRPGQSPK RLIYLVSKLDSGVPDRFSGSGSGTDFTLKISRIEAEDVGLYYCWQGTHFP RTFGGGTKLEIKR |
| 9 | HC-CDR1 | NYGMS |
| 10 | HC-CDR2 | SIRSGGGRTYYSDNVKG |
| 11 | HC-CDR3 | YDHYSGSSDY |
| 12 | LC-CDR1 | KSSQSLLDSDGKTYLN |
| 13 | LC-CDR2 | LVSKLDS |
| 14 | LC-CDR3 | WQGTHFPRT |
| 15 | IgG1 heavy chain constant region | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLN GKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKS RWQQGNVFSCSVMHEALHNHYTQKSLSLSPGK |
| 16 | IgG4 heavy chain constant region | ASTKGPSVFPLAPCSRSTSESTAALGCLVKDYFPEPVTVSWNSGALTSGV HTFPAVLQSSGLYSLSSVVTVPSSSLGTKTYTCNVDHKPSNTKVDKRVES KYGPPCPSCPAPEFLGGPSVFLFPPKPKDTLMISRTPEVTCVVVDVSQEDP EVQFNWYVDGVEVHNAKTKPREEQFNSTYRVVSVLTVLHQDWLNGKE YKCKVSNKGLPSSIEKTISKAKGQPREPQVYTLPPSQEEMTKNQVSLTCL VKGFYPSDIAVEWESNGQPENNYKTTPPVLDSDGSFFLYSRLTVDKSRW QEGNVFSCSVMHEALHNHYTQKSLSLSLGK |
| 17 | Light chain kappa constant region | TVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVT KSFNRGEC |
| 18 | Light chain lambda constant region | QPKANPTVTLFPPSSEELQANKATLVCLISDFYPGAVTVAWKADGSPVK AGVETTKPSKQSNNKYAASSYLSLTPEQWKSHRSYSCQVTHEGSTVEKT VAPTECS |
| 19 | hu3D6-D $V_H$ v2 | EVQLVESGGGLVQPGGSLRLSCAASGFTFSNYGMSWVRQASDKRLEWV ASIRSGGGRTYYSDNVKGRFTISRDNSKNTLYLQMNSLRAEDTALYYCV RYDHYSGSSDYWGQGTLVTVSS |

TABLE 2-continued

Exemplary anti-Aβ catabody sequences.

| SEQ ID NO | Description | Sequence |
|---|---|---|
| 20 | hu3D6-D V$_H$ v3 | EVQLVESGGGLVQPGGSLRLSCAASGFTFSNYGMSWVRQNSDKRLEWV ASIRSGGGRTYYSDNVKGRFTISRDNSKNTLYLQMNSLRAEDTALYYCV RYDHYSGSSDYWGQGTLVTVSS |
| 21 | bu3D6-D V$_L$ v3 | DVVMTQSPLSLPVTLGQPASISCKSSQSLLDSDGKTYLNWLLQRPGQSPR RLIYLVSKLDSGVPDRFSGSGSGTDFTLKISRVEAEDVGVYYCWQGTHFP RTFGGGTKVEIKR |
| 22 | hu3D6-D V$_L$ v4 | DVVMTQSPLSLPVTLGQPASISCKSSQSLLDSDGKTYLNWLLQRPGQSPR RLIYLVSKLDSGVPDRFSGSGSGTDFTLKISRIEAEDVGVYYCWQGTHFP RTFGGGTKVEIKR |

Also provided is a method of treating or preventing Alzheimer's disease in an individual, comprising administering to the individual an effective amount of any one of the anti-Aβ catabodies (or pharmaceutical compositions thereof) described herein.

Aβ Peptides

In some embodiments, the anti-Aβ catabody specifically binds to and cleaves an Aβ peptide. In some embodiments, the anti-Aβ catabody specifically binds to and cleaves a human Aβ peptide, such as Aβ(1-40) or Aβ(1-42). In some embodiments, the anti-Aβ catabody specifically binds to and cleaves an Aβ peptide in helical conformation. In some embodiments, the anti-Aβ catabody specifically binds to the N-terminus of Aβ, such as N-terminal 3, 4, 5, 6, 7, 8, 9, 10, or more amino acids of Aβ(1-40).

In some embodiments, the anti-Aβ catabody specifically binds to and cleaves an Aβ oligomer. In some embodiments, the anti-Aβ catabody specifically binds to and cleaves soluble Aβ. In some embodiments, the anti-Aβ catabody specifically binds to and cleaves Aβ in amyloid plaques. In some embodiments, the anti-Aβ catabody specifically binds to and cleaves Aβ in the brain. In some embodiments, the anti-Aβ catabody specifically binds to and cleaves vascular Aβ.

In some embodiments, the anti-Aβ catabody cross-reacts with Aβ from species other than human, such as mouse or rat. In some embodiments, the anti-Aβ catabody is completely specific for human Aβ and does not exhibit species or other types of non-human cross-reactivity. In some embodiments, the anti-Aβ catabody cross-reacts with at least one allelic variant of Aβ. In some embodiments, the anti-Aβ catabody does not cross-react with any allelic variant of Aβ.

As are peptides of 36-43 amino acids that have been implicated as the main component of amyloid plaques found in the brains of Alzheimer patients. Aβ peptides are derived from amyloid precursor protein (APP), which is cleaved by beta secretase and gamma secretase to yield Aβ. Aβ molecules can aggregate to form flexible soluble oligomers which may exist in several forms and are toxic to neurons.

Recent research suggests that soluble oligomeric forms of the peptide may be causative agents in the development of Alzheimer's disease. Accordingly to the "amyloid hypothesis", the Aβ plaques are responsible for the pathology of Alzheimer's disease. Brain Aβ is elevated in patients with sporadic Alzheimer's disease. Aβ is the main constituent of brain parenchymal and vascular amyloid and it contributes to cerebrovascular lesions and is neurotoxic. Aβ circulates in plasma, cerebrospinal fluid (CSF) and brain interstitial fluid (ISF) mainly as soluble Aβ40. Senile amyloid plaques contain both Aβ40 and Aβ42, while vascular amyloid is predominantly the shorter Aβ40. Several sequences of Aβ were found in both lesions. Increases in either total Aβ levels or the relative concentration of both Aβ40 and Aβ42 have been implicated in the pathogenesis of both familial and sporadic Alzheimer's disease. Due to its more hydrophobic nature, the Aβ42 is the most amyloidogenic form of the peptide. Aβ42 is also referred to as Aβ(1-42). Aβ40 is also referred to as Aβ(1-40).

Bapineuzumab is a humanized form of murine monoclonal antibody 3D6, which targets the N-terminal 5 residues of A peptide in a helical conformation. Large scale phase III clinical trials of Bapineuzumab in patients having mild to moderate Alzheimer's disease were halted in August 2012 when the antibody failed to arrest cognitive decline. Also, Bapineuzumab was the first antibody to be found to cause amyloid-related imaging abnormalities, including an accumulation of fluid in brain tissue in patients receiving high doses. No health risks were found in patients receiving either 0.5 or 1 mg of bapineuzumab.

The V$_H$ of 3D6 comprises the amino acid sequence of SEQ ID NO: 4. The V$_L$ of 3D6 comprises the amino acid sequence of SEQ ID NO: 23. The V$_H$ of bapineuzumab comprises the amino acid sequence of SEQ ID NO: 24. The V$_L$ of bapineuzumab comprises the amino acid sequence of SEQ ID NO: 25.

3D6 V$_L$
SEQ ID NO: 23
YVVMTQTPLTLSVTIGQPASISCKSSQSLLDSDGKTYLNWLLQRPGQSPK

RLIYLVSKLDSGVPDRFTGSGSGTDFTLKISRIEAEDLGLYYCWQGTHFP

RTFGGGTKLEIKR bapineuzumab VH
SEQ ID NO: 24
EVQLLESGGGLVQPGGSLRLSCAASGFTFSNYGMSWVRQAPGKGLEWVAS

IRSGGGRTYYSDNVKGRFTISRDNAKNSLYLQMNSLRAEDTALYYCVRYD

HYSGSSDYWGQGTLVTVSS bapineuzumab VL
SEQ ID NO: 25
YVVMTQSPLSLPVTPGEPASISCKSSQSLLDSDGKTYLNWLLQKPGQSPQ

RLIYLVSKLDSGVPDRFSGSGSGTDFTLKISRVEAEDVGVYYCWQGTHFP

RTFGQGTKVEIKR

Antibody Variants

Variants and derivatives of any one of the therapeutic catabodies (such as anti-Aβ catabodies) described above are also provided herein.

Substitution, Insertion, Deletion and Variants

In some embodiments, amino acid sequence variants of the therapeutic catabodies (such as anti-Aβ catabodies) provided herein are contemplated. For example, it may be desirable to improve the binding affinity and/or other biological properties of the catabodies. Amino acid sequence variants of a catabody may be prepared by introducing appropriate modifications into the nucleotide sequence encoding the catabody, or by peptide synthesis. Such modifications include, for example, deletions from, and/or insertions into and/or substitutions of residues within the amino acid sequences of the catabody. Any combination of deletion, insertion, and substitution can be made to arrive at the final construct, provided that the final construct possesses the desired characteristics, e.g., antigen-binding and cleavage.

In some embodiments, the catabody variants having one or more amino acid substitutions are provided. Sites of interest for substitutional mutagenesis include the CDRs and FRs. Amino acid substitutions may be introduced into a catabody of interest and the products screened for a desired activity, e.g., retained/improved antigen binding and cleavage, decreased immunogenicity, or improved ADCC or CDC.

Conservative substitutions are shown in Table 3 below.

TABLE 3

CONSERVATIVE SUBSTITITIONS

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr, Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties:
 a. hydrophobic: Norleucine, Met, Ala, Val, Leu, Ile;
 b. neutral hydrophilic: Cys, Ser, Thr, Asn, Gln;
 c. acidic: Asp, Glu;
 d. basic: His, Lys, Arg;
 e. residues that influence chain orientation: Gly, Pro;
 f. aromatic: Trp, Tyr, Phe.

Non-conservative substitutions will entail exchanging a member of one of these classes for another class.

An exemplary substitutional variant is an affinity matured catabody, which may be conveniently generated, e.g., using phage display-based affinity maturation techniques. Briefly, one or more CDR residues are mutated and the variant catabodies displayed on phage and screened for a particular biological activity (e.g., binding affinity). Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or specificity determining residues (SDRs), with the resulting variant $V_H$ or $V_L$ being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, NJ, (2001).)

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more CDRs so long as such alterations do not substantially reduce the ability of the catabody to bind and cleave antigen. For example, conservative alterations (e.g., conservative substitutions as provided herein) that do not substantially reduce binding affinity or antigen-cleavage activity may be made in CDRs. Such alterations may be outside of HVR "hotspots" or SDRs. In some embodiments of the variant $V_H$ and $V_L$ sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys. and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex can be determined to identify contact points between the antibody and antigen. Such contact residues and neighboring residues may be targeted or eliminated as candidates for substitution. Variants may be screened to determine whether they contain the desired properties.

The catabody variants described herein maintain their catalytic activity against the target protein (e.g., Aβ). The catalytic triad, i.e. the SHD motif in the $V_L$ of the therapeutic catabody cannot be substituted. In some embodiments, one or more amino acid residues in the $V_L$ of the therapeutic catabody that support its catalytic activity cannot be substituted, including, for example, the amino acid residue at positions 26, 27D, and 28 of the $V_L$, wherein the numbering is according to the EU index of Kabat.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a catabody with an N-terminal methionyl residue. Other insertional variants of the catabody include the fusion to the N- or C-terminus of the antibody to an enzyme (e.g. for ADEPT) or a polypeptide which increases the serum half-life of the antibody.

Catabody variants are also provided with amino-terminal leader extensions. For example, one or more amino acid residues of the amino-terminal leader sequence are present at the amino-terminus of any one or more heavy or light chains of an antibody. An exemplary amino-terminal leader extension comprises or consists of three amino acid residues, VHS, present on one or both light chains of an antibody variant.

Chimeric and Humanized Catabodies

In some embodiments, the therapeutic catabody provided herein is a chimeric antibody. Certain chimeric antibodies are described, e.g., in U.S. Pat. No. 4,816,567; and Morrison et al., (1984) *Proc. Natl. Acad. Sci. USA*, 81:6851-6855 (1984)). In one example, a chimeric antibody comprises a non-human variable region (e.g., a variable region derived from a mouse) and a human constant region. In a further example, a chimeric antibody is a "class switched" antibody in which the class or subclass has been changed from that of the parent antibody. Chimeric antibodies include antigen-binding fragments thereof.

In some embodiments, humanized catabodies are provided. Humanized antibodies are useful as therapeutic molecules because humanized antibodies reduce or eliminate the human immune response to non-human antibodies (such as the human anti-mouse antibody (HAMA) response), which can result in an immune response to an antibody therapeutic, and decreased effectiveness of the therapeutic.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, (2008) *Front. Biosci.* 13: 1619-1633, and are further described, e.g., in Riechmann et al., (1988) *Nature* 332:323-329; Queen et al., (1989) *Proc. Natl Acad Sci. USA* 86: 10029-10033; U.S. Pat. Nos. 5,821,337, 7,527,791, 6,982,321, and 7,087,409; Kashmiri et al., (2005) *Methods* 36:25-34 (describing SDR (a-CDR) grafting); Padlan, (1991) *Mol. Immunol.* 28:489-498 (describing "resurfacing"); Dall'Acqua et al., (2005) *Methods* 36:43-60 (describing "FR shuffling"); and Osbourn et al., (2005) *Methods* 36:61-68 and Klimka et al., (2000) *Br. J. Cancer,* 83:252-260 (describing the "guided selection" approach to FR shuffling).

Human framework regions that may be used for humanization include but are not limited to: framework regions selected using the "best-fit" method (see, e.g., Sims et al. (1993) *J. Immunol.* 151:2296); framework regions derived from the consensus sequence of human antibodies of a particular subgroup of light or heavy chain variable regions (see, e.g., Carter et al. (1992) *Proc. Natl. Acad. Sci. USA,* 89:4285; and Presta et al. (1993) *J. Immunol,* 151:2623); human mature (somatically mutated) framework regions or human germline framework regions (see, e.g., Almagro and Fransson, (2008) *Front. Biosci.* 13:1619-1633); and framework regions derived from screening FR libraries (see, e.g., Baca et al., (1997) *J. Biol. Chem.* 272: 10678-10684 and Rosok et al., (1996) *J. Biol. Chem.* 271:22611-22618).

Library-Derived Antibodies

The therapeutic catabodies may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa. NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004): Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically displays antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J.* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126.2007/0160598, 2007/0237764, 2007/0292936, and 2009/0002360.

Fc Region Variants

In some embodiments, one or more amino acid modifications may be introduced into the Fc region of the therapeutic catabodies (such as anti-Aβ catabodies) provided herein, thereby generating an Fc region variant. In some embodiments, the Fc region variant has enhanced ADCC effector function, often related to binding to Fc receptors (FcRs). In some embodiments, the Fc region variant has decreased ADCC effector function. There are many examples of changes or mutations to Fc sequences that can alter effector function. For example, WO 00/42072 and Shields et al. *J Biol. Chem.* 9(2): 6591-6604 (2001) describe antibody variants with improved or diminished binding to FcRs. The contents of those publications are specifically incorporated herein by reference.

In some embodiments, the therapeutic catabody comprises an Fc region that possesses some but not all effector functions, which makes it a desirable candidate for applications in which the half-life of the catabody in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat7Acad. Sci. USA* 83:7059-7063 (1986)) and Hellstrom, I et al., *Proc. Nat'l Acad. Si. USA* 82:1499-1502 (1985); U.S. Pat. No. 5,821,337 (see Bruggemann, M. et al., *J Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CYTOTOX 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al, *Blood* 101: 1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogic et al., *J. Immunol.* 164: 4178-4184 (2000).

Antibodies with increased half-lives and improved binding to FcRn are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:73840 (1988); U.S. Pat. No. 5,648,260: U.S. Pat. No. 5,624,821; and WO 94/29351 concerning other examples of Fc region variants.

Glycosylation Variants

In some embodiments, the therapeutic catabody (such as anti-Aβ catabody) provided herein is altered to increase or decrease the extent to which the construct is glycosylated. Addition or deletion of glycosylation sites to an antibody may be conveniently accomplished by altering the amino acid sequence of the antibody such that one or more glycosylation sites is created or removed.

Where the catabody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose. N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the catabody may be made in order to create catabody variants with certain improved properties.

The N-glycans attached to the CH2 domain of Fc is heterogeneous. Antibodies or Fc fusion proteins generated in CHO cells are fucosylated by fucosyltransferase activity. See Shoji-Hosaka et al., J. Biochem. 2006, 140:777-83. Normally, a small percentage of naturally occurring afucosylated IgGs may be detected in human serum. N-glycosylation of the Fc is important for binding to FcγR; and afucosylation of the N-glycan increases Fc's binding capacity to FcγRIIIa. Increased FcγRIIIa binding can enhance ADCC, which can be advantageous in certain therapeutic applications in which cytotoxicity is desirable.

In some embodiments, an enhanced effector function can be detrimental when Fc-mediated cytotoxicity is undesirable. In some embodiments, the Fc fragment or CH2 domain is not glycosylated. In some embodiments, the N-glycosylation site in the CH2 domain is mutated to prevent from glycosylation.

In some embodiments, catabody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/

0115614; US 2002/0164328; US 2004/0093621; US 2004/0132140; US 2004/0110704; US 2004/0110282; US 2004/0109865; WO 2003/085119: WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lee13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4): 680-688 (2006); and WO2003/085107).

Catabody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.): U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

Derivatives

In some embodiments, the therapeutic catabodies (such as anti-Aβ catabodies) provided herein may be further modified to contain additional non-proteinaceous moieties that are known in the art and readily available. The moieties suitable for derivatization of the catabodies include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the catabody may vary, and if more than one polymer are attached, they can be the same or different molecules. In general, the number and/or type of polymers used for derivatization can be determined based on considerations including, but not limited to, the particular properties or functions of the catabody to be improved, whether the catabody derivative will be used in a therapy under defined conditions, etc.

IV. Methods of Preparation

The therapeutic catabodies (such as anti-Aβ catabodies) described herein can be prepared using any known methods in the art, including those described below and in the Examples. Therapeutic catabodies can be obtained by immunizing lab animals against target antigens, such as transition-state analogs. See, for example, US2010018361A1 and Taguchi H, et al. "Catalytic antibodies to amyloid beta peptide in defense against Alzheimer disease," *Autoimmun. Rev.* 7:391-397 (2008), which are incorporated herein by reference. Therapeutic catabodies may also be expressed recombinantly.

Nucleic Acids

The present application further provides isolated nucleic acid molecules comprising polynucleotides that encode one or more chains of the therapeutic catabodies (such as anti-Aβ catabodies) described herein. In some embodiments, a nucleic acid molecule comprises a polynucleotide that encodes a heavy chain or a light chain of the therapeutic catabody (such as anti-Aβ catabody). In some embodiments, a nucleic acid molecule comprises both a polynucleotide that encodes a heavy chain and a polynucleotide that encodes a light chain of the therapeutic catabody (such as anti-Aβ catabody). In some embodiments, a first nucleic acid molecule comprises a first polynucleotide that encodes a heavy chain and a second nucleic acid molecule comprises a second polynucleotide that encodes a light chain. In some embodiments, the first polynucleotide that encodes the heavy chain is operably linked to a first promoter, and the second polynucleotide that encodes the light chain is operably linked to a second promoter. In some embodiments, the polynucleotide that encodes the heavy chain and the polynucleotide that encodes the light chain is operably linked to a promoter.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the expression of the therapeutic catabody is inducible. In some embodiments, a nucleic acid sequence encoding the therapeutic catabody is operably linked to an inducible promoter.

In some embodiments, a polynucleotide encoding a heavy chain or light chain of therapeutic catabody (such as anti-Aβ catabody) comprises a nucleotide sequence that encodes a leader sequence, which, when translated, is located at the N terminus of the heavy chain or light chain. The leader sequence may be the native heavy or light chain leader sequence, or may be another heterologous leader sequence. In some embodiments, the nucleic acid (or a set of nucleic acids) encoding the therapeutic catabody (such as anti-Aβ catabody) may further comprises a nucleic acid sequence encoding a peptide tag (such as protein purification tag, e.g., His-tag. HA tag).

The present application also includes variants to these nucleic acid sequences. For example, the variants include nucleotide sequences that hybridize to the nucleic acid sequences encoding any one of the therapeutic catabodies described herein under at least moderately stringent hybridization conditions.

Nucleic acid molecules may be constructed using recombinant DNA techniques conventional in the art. In some embodiments, a nucleic acid molecule is an expression vector that is suitable for expression in a selected host cell.

Vectors

Vectors comprising polynucleotides that encode the heavy chains and/or light chains of any one of the therapeutic catabodies (such as anti-Aβ catabodies) described herein are provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Green and Sambrook (2013, Molecular Cloning: A Laboratory Manual, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

In brief summary, the expression of the therapeutic catabody by a natural or synthetic nucleic acid encoding the catabody can be achieved by inserting the nucleic acid into an appropriate expression vector, such that the nucleic acid is operably linked to 5' and 3' regulatory elements, including for example a promoter (e.g., a lymphocyte-specific promoter) and a 3' untranslated region (UTR). The vectors can be suitable for replication and integration in eukaryotic host cells. Typical cloning and expression vectors contain transcription and translation terminators, initiation sequences, and promoters useful for regulation of the expression of the desired nucleic acid sequence.

In some embodiments, a vector is selected that is optimized for expression of polypeptides in CHO or CHO-derived cells, or in NSO cells. Exemplary such vectors are described, e.g., in Running Deer et al., *Biotechnol. Prog.* 20:880-889 (2004).

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, pi-galactosidase, chloramphenicol acetyl transferase, secreted alkaline phosphatase, or the green fluorescent protein gene (e.g., Ui-Tel et al., 2000 *FEBS Letters* 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Host Cells

The present application provides isolated host cells comprising any one of the therapeutic catabodies (such as anti-Aβ catabodies), nucleic acid molecules, or vectors described herein.

The therapeutic catabodies (such as anti-Aβ catabodies) described herein may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S. DG44. Lec13 CHO cells, and FUT8 CHO cells; PER.C6® cells (Crucell); and NSO cells. Suitable nonmammalian host cells include prokaryotes (such as *E. coli* or *B. subtillis*) and yeast (such as *S. cerevisae, S. pombe*; or *K. lactis*). In some embodiments, a particular eukaryotic host cell is selected based on its ability to make desired post-translational modifications to the heavy chains and/or light chains of the antibody. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Non-limiting exemplary methods are described, e.g., in Sambrook et al., Molecular Cloning, A Laboratory Manual, $3^{rd}$ ed. Cold Spring Harbor Laboratory Press (2001). Nucleic acids may be transiently or stably transfected in the desired host cells, according to any suitable method.

In some embodiments, the therapeutic catabody is produced in a cell-free system. Non-limiting exemplary cell-free systems are described, e.g., in Sitaraman et al., *Methods Mot. Biol.* 498: 229-44 (2009); Spirin, *Trends Biotechnol.* 22: 53845 (2004); Endo et al., *Biotechnol. Adv.* 21: 695-713 (2003).

Purification

The therapeutic catabodies (such as anti-Aβ catabodies) may be purified by any suitable method. Such methods include, but are not limited to, the use of affinity matrices or hydrophobic interaction chromatography. Suitable affinity ligands include ligands that bind antibody constant regions. For example, a Protein A, Protein G, Protein A/G, or an antibody affinity column may be used to bind the constant region and to purify an antibody comprising an Fc fragment. Hydrophobic interactive chromatography, for example, a butyl or phenyl column, may also suitable for purifying some polypeptides such as antibodies. Ion exchange chromatography (e.g. anion exchange chromatography and/or cation exchange chromatography) may also suitable for purifying some polypeptides such as antibodies. Mixed-mode chromatography (e.g. reversed phase/anion exchange, reversed phase/cation exchange, hydrophilic interaction/anion exchange, hydrophilic interaction/cation exchange, etc.) may also suitable for purifying some polypeptides such as antibodies. Many methods of purifying polypeptides are known in the art.

V. Compositions, Kits and Articles of Manufacture

Also provided herein are compositions (such as pharmaceutical compositions) comprising any one of the therapeutic catabodies (such as anti-Aβ catabodies), nucleic acids, vectors, or host cells described herein.

Pharmaceutical compositions of the therapeutic catabodies (such as anti-Aβ catabodies) described herein can be obtained by mixing the therapeutic catabodies (such as anti-Aβ catabodies) having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride: phenol, butyl or benzyl alcohol: alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine: monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Lyophilized formulations adapted for subcutaneous administration are described in WO97/04801. Such lyophilized formulations may be reconstituted with a suitable diluent to a high protein concentration and the reconstituted formulation may be administered subcutaneously to the individual to be imaged, diagnosed, or treated herein.

Pharmaceutical compositions to be used for in vivo administration must be sterile. This is readily accomplished by, e.g., filtration through sterile filtration membranes.

Also provided are kits useful for any one of the methods of determining catabody levels, diagnosis and treatment described herein, including kits comprising any one of the therapeutic catabodies (such as anti-Aβ catabodies) described herein.

In some embodiments, there is provided a kit for determining catabody levels in a biological sample, comprising a substrate peptide comprises the amino acid sequence $(EAR)_n$ (SEQ ID NO: 2), and wherein n is an integer between 1 and 30 (e.g., n is 3). In some embodiments, the kit further comprises an antibody that specifically binds to total Ig (e.g., total human Ig, such as total IgM, total IgG, total IgA, and/or total IgE). In some embodiments, the kit comprises a solid support (e.g., ELISA plate).

In some embodiments, there is provided a kit for diagnosing a PAD or determining a risk for a PAD in an individual, wherein the PAD is associated with a target protein, comprising: a) a substrate peptide comprises the amino acid sequence $(EAR)_n$ (SEQ ID NO: 2), and wherein n is an integer between 1 and 30 (e.g., n is 3); and b) the target protein (or a fragment thereof) or an antibody against the target protein. In some embodiments, the kit further comprises an antibody that specifically binds to total Ig (e.g., total human Ig, such as total IgM, total IgG, total IgA, and/or total IgE). In some embodiments, the kit comprises a solid support (e.g., ELISA plate).

In some embodiments, there is provided a kit for diagnosing AD or determining a risk for AD in an individual, comprising: a) a substrate peptide comprises the amino acid sequence $(EAR)_n$ (SEQ ID NO: 2), and wherein n is an integer between 1 and 30 (e.g., n is 3); b) an Aβ peptide (e.g., Aβ(1-42)) or an anti-Aβ antibody; and c) an antibody that specifically binds to total Ig (e.g., total human Ig, such as total IgM, total IgG, total IgA, and/or total IgE). In some embodiments, the kit comprises a solid support (e.g., ELISA plate).

In some embodiments, there is provided a kit for treating or preventing a PAD in an individual, wherein the PAD is associated with a target protein, comprising: a) a substrate peptide comprises the amino acid sequence $(EAR)_n$ (SEQ ID NO: 2), and wherein n is an integer between 1 and 30 (e.g., n is 3); b) the target protein (or a fragment thereof) or an antibody against the target protein; c) an antibody that specifically binds to total Ig (e.g., total human Ig, such as total IgM, total IgG, total IgA, and/or total IgE); and d) a therapeutic catabody that specifically binds to the target protein. In some embodiments, the kit comprises a solid support (e.g., ELISA plate).

In some embodiments, there is provided a kit for treating or preventing AD in an individual, comprising: a) a substrate peptide comprises the amino acid sequence (EAR)$_n$ (SEQ ID NO: 2), and wherein n is an integer between 1 and 30 (e.g., n is 3); b) an Aβ peptide (e.g., Aβ(1-42)) or an anti-Aβ antibody; c) an antibody that specifically binds to total Ig (e.g., total human Ig, such as total IgM, total IgG, total IgA, and/or total IgE); and d) a therapeutic catabody that specifically binds to Aβ, such as any one of the anti-Aβ catabodies described herein. In some embodiments, the kit comprises a solid support (e.g., ELISA plate).

In some embodiments, there is provided a kit for treating or preventing AD in an individual, comprising a pharmaceutical composition comprising an anti-Aβ catabody and a pharmaceutically acceptable carrier, wherein the anti-Aβ catabody comprises: a $V_L$ comprising a LC-CDR1 comprising the amino acid sequence of SEQ ID NO: 12, LC-CDR2 comprising the amino acid sequence of SEQ ID NO: 13, and an LC-CDR3 comprising the amino acid sequence of SEQ ID NO: 14, or a variant thereof comprising up to about 5 amino acid substitutions in the LC-CDRs, wherein the amino acid residue at position 1 of the $V_L$ is D, the amino acid residue at position 27A of the $V_L$ is S, and the amino acid residue at position 93 of the $V_L$ is H, and wherein the numbering is according to the EU index of Kabat. In some embodiments, the amino acid residue at position 26 of the $V_L$ is Ser (S), the amino acid residue at position 27D of the $V_L$ is D. E or H, and/or the amino acid residue at position 28 of the $V_L$ is D or N, and wherein the numbering is according to the EU index of Kabat. In some embodiments, the anti-Aβ catabody comprises a $V_H$ comprising an HC-CDR1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11, or a variant thereof comprising up to about 5 amino acid substitutions in the HC-CDRs.

The kits of the present application are in suitable packaging. Suitable packaging includes, but is not limited to, vials, bottles, jars, flexible packaging (e.g., sealed Mylar or plastic bags), and the like. Kits may optionally provide additional components such as reagents (e.g., ECL substrate), buffers (e.g., coating buffer, blocking buffer, washing buffer, antibody dilution buffer, developing buffer, etc.), antibodies (e.g., anti-human Ig antibody), and interpretative information.

The present application thus also provides articles of manufacture. The article of manufacture can comprise a container and a label or package insert on or associated with the container. Suitable containers include vials (such as sealed vials), bottles, jars, flexible packaging, and the like. In some embodiments, the container holds a pharmaceutical composition, and may have a sterile access port (for example the container may be an intravenous solution bag or a vial having a stopper pierceable by a hypodermic injection needle). In some embodiments, the container holds substrate peptides or target protein (e.g., Aβ) for use in the immunoassays. The label or package insert indicates that the composition is used for diagnosing (including determining a risk), treating or preventing a PAD (e.g., AD) in an individual. The label or package insert will further comprise instructions for performing the immunoassays to determine one or more SHD catabody levels in a biological sample, and/or administering the pharmaceutical composition to the individual. The label may indicate directions for reconstitution and/or use of the various components. The container holding the pharmaceutical composition may be a multi-use vial, which allows for repeat administrations (e.g. from 2-6 administrations) of the reconstituted formulation. Package insert refers to instructions customarily included in commercial packages of diagnostic and/or therapeutic products that contain information about the indications, usage, dosage, administration, contraindications and/or warnings concerning the use of such products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the pharmaceutical compositions and instructions for use, packaged in quantities sufficient for storage and use in pharmacies, for example, hospital pharmacies and compounding pharmacies.

Exemplary Embodiments

Embodiments 1. A method for determining the level of one or more SHD catabodies in a biological sample, comprising:
  a) contacting the biological sample with a substrate peptide immobilized on a solid support under conditions that allow formation of a catabody-substrate peptide complex, and
  b) determining the amount of the catabody-substrate peptide complex, thereby providing the level of one or more SHD catabodies in the biological sample,
  wherein the substrate peptide comprises the amino acid sequence (EAR)$_n$ (SEQ ID NO: 2), and wherein n is an integer between 1 and 30.

Embodiments 2. The method of embodiment 1, wherein n is 3.

Embodiments 3. The method of embodiment 1 or 2, wherein the biological sample is a serum sample.

Embodiments 4. The method of embodiment 3, wherein the serum sample contains at least about 1 μg/mL immunoglobulin (Ig).

Embodiments 5. The method of any one of embodiments 1-4, wherein the biological sample is incubated with the substrate peptide for about 1 hour to about 16 hours.

Embodiments 6. The method of any one of embodiments 1-5, wherein the amount of the catabody-substrate peptide complex is determined using an antibody that specifically binds to total Ig.

Embodiments 7. The method of embodiment 6, wherein the antibody is labeled with an enzyme or a fluorescent label.

Embodiments 8. A method for determining a risk for a protein aggregation disease (PAD) in an individual, wherein the PAD is associated with aggregation of a target protein, comprising determining the level of one or more SHD catabodies in a biological sample of the individual, wherein the individual is determined as having a risk for the PAD if the level of the one or more SHD catabodies is lower than a control SHD catabody level.

Embodiments 9. The method of embodiment 8, wherein the level of one or more SHD catabodies is the level of one or more SHD catabodies that specifically bind to the target protein.

Embodiments 10. The method of embodiment 8, wherein the level of one or more SHD catabodies is the level of total SHD catabodies.

Embodiments 11. The method of embodiment 10, wherein the level of total SHD catabodies is determined by contacting a serum sample of the individual with a substrate peptide immobilized on a solid support under conditions that allow formation of a catabody-substrate peptide complex, and determining the amount of the catabody-substrate peptide complex, wherein the substrate peptide comprises the amino acid sequence $(EAR)_n$ (SEQ ID NO: 2), wherein n is an integer between 1 and 30.

Embodiments 12. The method of embodiment 11, wherein n is 3.

Embodiments 13. The method of embodiment 11 or 12, wherein the serum sample contains at least about 1 µg/mL Ig.

Embodiments 14. The method of any one of embodiments 11-13, wherein the serum sample is incubated with the substrate peptide for about 1 hour to about 16 hours.

Embodiments 15. The method of any one of embodiments 11-14, wherein the amount of the catabody-substrate peptide complex is determined using an antibody that specifically binds to total Ig.

Embodiments 16. The method of embodiment 15, wherein the antibody is labeled with an enzyme or a fluorescent label.

Embodiments 17. The method of any one of embodiments 8-16, further comprising determining the level of an auto-antibody against the target protein in a biological sample of the individual, wherein the individual is determined as having a risk for the PAD if: (i) the level of the one or more SHD catabodies is lower than a control SHD catabody level; and (ii) the level of the auto-antibody against the target protein is lower than a control auto-antibody level.

Embodiments 18. The method of embodiment 17, wherein the level of the auto-antibody is determined by contacting a serum sample of the individual with the target protein under conditions that allow formation of an auto-antibody-target protein complex, and determining the amount of the auto-antibody-target protein complex.

Embodiments 19. The method of embodiment 18, wherein the level of the auto-antibody is determined using an ELISA assay.

Embodiments 20. The method of any one of embodiments 17-19, wherein the control auto-antibody level is the level of the auto-antibody against the target protein in a healthy individual.

Embodiments 21. The method of any one of embodiments 17-19, wherein the control auto-antibody level is the median level of the auto-antibody against the target protein in a population of individuals.

Embodiments 22. The method of any one of embodiments 8-16, further comprising determining the level of the target protein in a biological sample of the individual, wherein the individual is determined as having a risk for the PAD if: (i) the level of the one or more SHD catabodies is lower than a control SHD catabody level; and (ii) the level of the target protein is higher than a control target protein level.

Embodiments 23. The method of any one of embodiments 8-22, wherein the control SHD catabody level is the level of one or more SHD catabodies in a healthy individual.

Embodiments 24. The method of any one of embodiments 8-22, wherein the control SHD catabody level is the median level of one or more SHD catabodies in a population of individuals.

Embodiments 25. The method of any one of embodiments 8-24, wherein the PAD is Alzheimer's disease, and wherein the target protein is amyloid β (Aβ).

Embodiments 26. The method of any one of embodiments 8-24, wherein:
(i) the PAD is Parkinson's disease, and the target protein is α-synuclein;
(ii) the PAD is Alzheimer's disease or dementia, and the target protein is Tau;
(iii) the PAD is ATTR amyloidosis, and the target protein is transthyretin;
(iv) the PAD is AL amyloidosis, and the target protein is immunoglobulin light chain;
(v) the PAD is frontotemporal lobar degeneration or amyotrophic lateral sclerosis, and the target protein is TDP43;
(vi) the PAD is Huntington's disease, and the target protein is Huntingtin;
(vii) the PAD is Type II diabetes, and the target protein is IAPP; or
(viii) the PAD is Amyotrophic Lateral Sclerosis, and the target protein is SOD1.

Embodiments 27. A method of treating or preventing a PAD in an individual, wherein the PAD is associated with aggregation of a target protein, comprising:
a) determining the individual as having a risk for the PAD according to the method of any one of embodiments 1-26; and
b) administering to the individual an effective amount of a therapeutic catabody that specifically binds to the target protein.

Embodiments 28. The method of embodiment 27, wherein the method is repeated at a frequency of no more than about every three months.

Embodiments 29. The method of embodiment 27 or 28, wherein the PAD is Alzheimer's disease, wherein the target protein is amyloid β (Aβ), wherein the therapeutic catabody comprises a light chain variable region ($V_L$) comprising a light chain complementarity determining region (LC-CDR) 1 comprising the amino acid sequence of SEQ ID NO: 12, an LC-CDR2 comprising the amino acid sequence of SEQ ID NO: 13, and an LC-CDR3 comprising the amino acid sequence of SEQ ID NO: 14, or a variant thereof comprising up to about 5 amino acid substitutions in the LC-CDRs, wherein the amino acid residue at position 1 of the $V_L$ is D, the amino acid residue at position 27A of the $V_L$ is S, and the amino acid residue at position 93 of the $V_L$ is H, and wherein the numbering is according to the EU index of Kabat.

Embodiments 30. The method of embodiment 29, wherein the therapeutic catabody comprises a heavy chain variable region ($V_H$) comprising a heavy chain complementarity determining region (HC-CDR) 1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11, or a variant thereof comprising up to about 5 amino acid substitutions in the HC-CDRs.

Embodiments 31. The method of embodiment 29 or 30, wherein the amino acid residue at position 26 of the $V_L$ is S, the amino acid residue at position 27D of the $V_L$ is D, E or H, and/or the amino acid residue at position 28 of the $V_L$ is D or N, and wherein the numbering is according to the EU index of Kabat.

Embodiments 32. The method of any one of embodiments 29-31, wherein the therapeutic catabody comprises a $V_H$ comprising an amino acid sequence having at least about 85% sequence identity to the amino acid sequence of SEQ ID NO: 4, 6, 19 or 20; and/or a $V_L$ comprising an amino acid sequence having at least about 85% sequence identity to the amino acid sequence of SEQ ID NO: 5, 7, 8, 21 or 22.

Embodiments 33. The method of embodiment 32, wherein the therapeutic catabody comprises: (i) a $V_H$ comprising the amino acid sequence of SEQ ID NO: 4, and a $V_L$ comprising the amino acid sequence of SEQ ID NO: 5; (ii) a $V_H$ comprising the amino acid sequence of SEQ ID NO: 6, and a $V_L$ comprising the amino acid sequence of SEQ ID NO: 7; (iii) a $V_H$ comprising the amino acid sequence of SEQ ID NO: 6, and a $V_L$ comprising the amino acid sequence of SEQ ID NO: 8; (iv) a $V_H$ comprising the amino acid sequence of SEQ ID NO: 19, and a $V_L$ comprising the amino acid sequence of SEQ ID NO: 21; (v) a $V_H$ comprising the amino acid sequence of SEQ ID NO: 20, and a $V_L$ comprising the amino acid sequence of SEQ ID NO: 21; (vi) a $V_H$ comprising the amino acid sequence of SEQ ID NO: 19, and a $V_L$ comprising the amino acid sequence of SEQ ID NO: 22; or (vii) a $V_H$ comprising the amino acid sequence of SEQ ID NO: 20, and a $V_L$ comprising the amino acid sequence of SEQ ID NO: 22.

Embodiments 34. The method of any one of embodiments 27-33, wherein the therapeutic catabody is a full-length IgG antibody.

Embodiments 35. The method of embodiment 34, wherein the therapeutic catabody comprises an IgG1 or IgG4 Fc region.

Embodiments 36. The method of any one of embodiments 27-33, wherein the therapeutic antibody is a full-length IgM antibody.

Embodiments 37. An isolated anti-Aβ catabody comprising: a $V_L$ comprising an LC-CDR1 comprising the amino acid sequence of SEQ ID NO: 12, an LC-CDR2 comprising the amino acid sequence of SEQ ID NO: 13, and an LC-CDR3 comprising the amino acid sequence of SEQ ID NO: 14, or a variant thereof comprising up to about 5 amino acid substitutions in the LC-CDRs, wherein the amino acid residue at position 1 of the $V_L$ is D, the amino acid residue at position 27A of the $V_L$ is S, and the amino acid residue at position 93 of the $V_L$ is H, and wherein the numbering is according to the EU index of Kabat.

Embodiments 38. An isolated anti-Aβ catabody comprising: a $V_H$ comprising an HC-CDR1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11, or a variant thereof comprising up to about 5 amino acid substitutions in the HC-CDRs, wherein the amino acid residue at position 1 of the $V_L$ is D, the amino acid residue at position 27A of the $V_L$ is S, and the amino acid residue at position 93 of the $V_L$ is H, and wherein the numbering is according to the EU index of Kabat.

Embodiments 39. The anti-Aβ catabody of embodiment 37 or 38, wherein the anti-AE catabody comprises a $V_H$ comprising an HC-CDR1 comprising the amino acid sequence of SEQ ID NO: 9, an HC-CDR2 comprising the amino acid sequence of SEQ ID NO: 10, and an HC-CDR3 comprising the amino acid sequence of SEQ ID NO: 11; and a $V_L$ comprising an LC-CDR1 comprising the amino acid sequence of SEQ ID NO: 12, an LC-CDR2 comprising the amino acid sequence of SEQ ID NO: 13, and an LC-CDR3 comprising the amino acid sequence of SEQ ID NO: 14.

Embodiments 40. The anti-Aβ catabody of any one of embodiments 37-39, wherein the anti-Aβ catabody cleaves a substrate having the formula EAR-AMC (SEQ ID NO: 1).

Embodiments 41. The anti-Aβ catabody of any one of embodiments 37-40, wherein the amino acid residue at position 26 of the $V_L$ is S, the amino acid residue at position 27D of the $V_L$ is D, E or H, and/or the amino acid residue at position 28 of the $V_L$ is D or N, and wherein the numbering is according to the EU index of Kabat.

Embodiments 42. The anti-Aβ catabody of any one of embodiments 37-41, wherein the anti-Aβ catabody comprises a $V_H$ comprising an amino acid sequence having at least about 85% sequence identity to the amino acid sequence of SEQ ID NO: 4, 6, 19 or 20; and/or a $V_L$ comprising an amino acid sequence having at least about 85% sequence identity to the amino acid sequence of SEQ ID NO: 5, 7, 8, 21 or 22.

Embodiments 43. The anti-Aβ catabody of embodiment 42, wherein the anti-Aβ catabody comprises: (i) a $V_H$ comprising the amino acid sequence of SEQ ID NO: 4, and a $V_L$ comprising the amino acid sequence of SEQ ID NO: 5; (ii) a $V_H$ comprising the amino acid sequence of SEQ ID NO: 6, and a $V_L$ comprising the amino acid sequence of SEQ ID NO: 7; (iii) a $V_H$ comprising the amino acid sequence of SEQ ID NO: 6, and a $V_L$ comprising the amino acid sequence of SEQ ID NO: 8; (iv) a $V_H$ comprising the amino acid sequence of SEQ ID NO: 19, and a $V_L$ comprising the amino acid sequence of SEQ ID NO: 21; (v) a $V_H$ comprising the amino acid sequence of SEQ ID NO: 20, and a $V_L$ comprising the amino acid sequence of SEQ ID NO: 21; (vi) a $V_H$ comprising the amino acid sequence of SEQ ID NO: 19, and a $V_L$ comprising the amino acid sequence of SEQ ID NO: 22; or (vii) a $V_H$ comprising the amino acid sequence of SEQ ID NO: 20, and a $V_L$ comprising the amino acid sequence of SEQ ID NO: 22.

Embodiments 44. The anti-Aβ catabody of any one of embodiments 37-43, wherein the anti-Aβ catabody is a full-length IgG antibody.

Embodiments 45. The anti-Aβ catabody of embodiment 44, wherein the anti-Aβ catabody comprises an IgG1 or IgG4 Fc region.

Embodiments 46. The anti-Aβ catabody of any one of embodiments 37-43, wherein the anti-Aβ catabody is a full-length IgM antibody.

Embodiments 47. A method of treating or preventing Alzheimer's disease in an individual, comprising administering to the individual an effective amount of the anti-Aβ catabody of any one of embodiments 37-46.

Embodiments 48. A kit for treating or preventing Alzheimer's disease in an individual, comprising:
a) a substrate peptide comprises the amino acid sequence $(EAR)_n$ (SEQ ID NO: 2), wherein n is an integer between 1 and 30;
b) an Aβ peptide; and
c) an antibody that specifically binds to total Ig.

Embodiments 49. The kit of embodiment 48, further comprising a solid support.

Embodiments 50. The kit of embodiment 48 or 49, further comprising a therapeutic catabody that specifically binds to Aβ.

EXAMPLES

The examples below are intended to be purely exemplary of the invention and should therefore not be considered to limit the invention in any way. The following examples and detailed description are offered by way of illustration and not by way of limitation.

Example 1. Catabodies as Serum Biomarker for Alzheimer's Disease

This example provides experimental data demonstrating that SHD catabodies (i.e., catabodies having an "SHD"

motif) can be used as serum biomarkers to diagnose or predict a protein aggregation diseases (PAD) such as Alzheimer's disease (AD).

A. Catabody Levels in Serum Samples of Young and Old Adults

Serum SHD catabody levels in young adults (20 to 29 years old; HS2, HS6, HS7 and HS8) and old adults (60 to 69 years old; HS1, HS3, HS4 and HS5) were measured using two immunoassays. In the EAR-AMC binding assay, an ELISA plate was coated with an EAR peptide (SEQ ID NO: 1) conjugated to 7-amino-4-methylcoumarin (AMC) ("EAR-AMC," 100X, Bachem Americas, Inc. Cat. No. I-1575.0050). In the EAR3 binding assay, an ELISA plate was coated with an (EAR)$_3$ peptide (SEQ ID NO: 3).

Briefly, each ELISA plate was coated with the corresponding peptide at a final concentration of about 5 μg/mL in a coating buffer (0.2M sodium carbonate-bicarbonate buffer, pH 9.4), 100 μL/well at 4° C. overnight. The plates were washed three times with a washing buffer (PBST: 0.1% Tween-20 in phosphate buffer saline "PBS"). The plates were then blocked with a blocking buffer (1% BSA in PBS) for 1 hour at room temperature, and washed three times with the washing buffer. To each well of the plate was added 100 μL of the corresponding serum sample (25 μg/mL or 100 μg/mL), and PBS was used as negative control. After incubation for 1 hour, the plates were then washed three times with the washing buffer. To each well of the plate was added 100 μL of a goat polyclonal antibody against human IgG conjugated to horseradish peroxidase (GAH-HRP; Abcam Cat. No. ab98605) at 1:10,000 dilution and incubated for 1 hour at room temperature and protected from exposure to light. HRP substrate (Amplex Red and H$_2$O$_2$) was prepared freshly with a developing buffer (3.6 mM Na$_2$HPO$_4$, 1.4 mM NaH$_2$PO$_4$, at pH7.2), and 100 μL of the HRP substrate was added to each well and incubated for 1-5 minutes. Signals were subsequently detected using a plate reader (Excitation wavelength=530 nm, Emission wavelength=590 nm, and cutoff wavelength=570 nm).

Figure 1B:
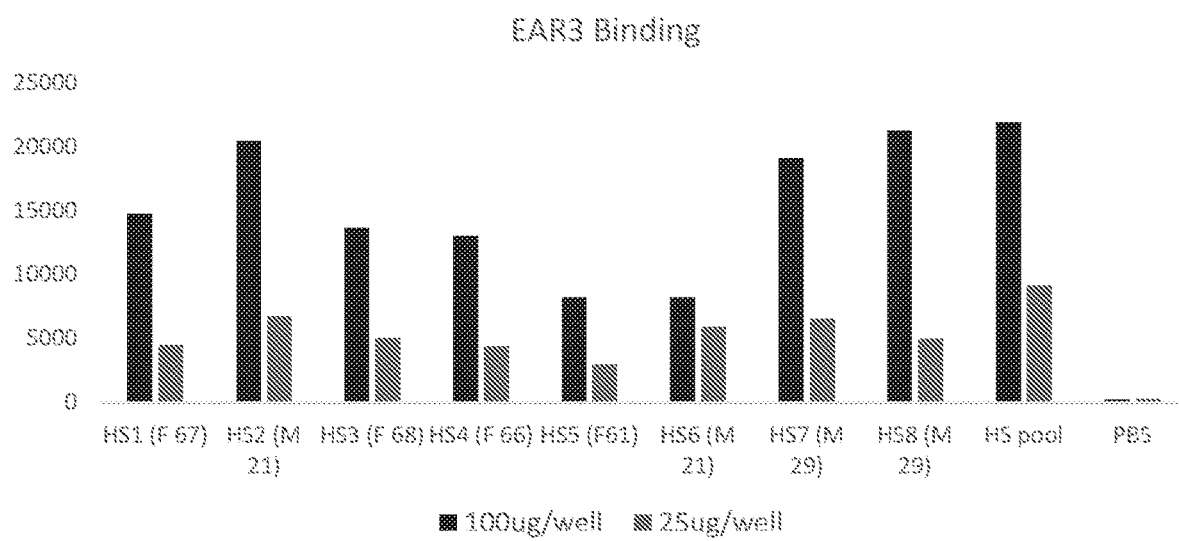
FIG. 1B shows catabody levels in the serum samples of young (20-29 years old) and old (60-69 years old) adults as determined by an EAR3 binding assay.

FIG. 1A shows the results of the EAR-AMC binding assay and FIG. 1B shows the results of the EAR3 binding assay. In both assays, the human serum pool (HS pool) and 3 out of 4 serum samples from the young adult group (20-29 years old) have higher serum SHD catabody levels compared to 3 out of 4 serum samples from the old adult group (60-69 years old). This result suggests that reduction of serum SHD catabodies might be an age-related event and serum level of SHD catabodies may serve as a biomarker to predict protein aggregation diseases.

B. Correlation Between Catabody Levels and Aβ-Specific Auto-Antibody Levels

Next, catabody levels and Ab-specific auto-antibody levels in serum samples from healthy individuals (HS1-8) and Alzheimer's disease patients (ALZ1-5) were determined using two immunoassays. In the EAR3 binding assay, an ELISA plate was coated with an (EAR)$_3$ peptide (SEQ ID NO: 3) at a final concentration of 5 μg/mL. In the Aβ binding assay, an ELISA plate was coated with a biotinylated amyloid (1-42) peptide at a final concentration of 1 μg/mL.

Briefly, each ELISA plate was coated with the corresponding peptide in a coating buffer (0.2M sodium carbonate-bicarbonate buffer, pH 9.4), 100 μL/well at 4° C. overnight. The plates were washed three times with a washing buffer (PBST). The plates were then blocked with a blocking buffer (10% Fetal Bovine Serum) for 1 hour at mom temperature, and washed three times with the washing buffer. To each well of the plate was added 100 μL of the corresponding serum sample (100 μg/mL), and PBS was used as negative control. After incubation for 1 hour, the plates were then washed three times with the washing buffer, and blocked with the blocking buffer for 1 hour at room temperature. The plates were subsequently washed with washing buffer for three times. To each well of the plate was added 100 μL GAH-HRP (Abcam Cat. No. ab98605) at 1:10.000 dilution and incubated for 1 hour at room temperature and protected from exposure to light. HRP substrate (Amplex Red and H$_2$O$_2$) was prepared freshly with a developing buffer (3.6 mM Na$_2$HPO$_4$, 1.4 mM NaH$_2$PO$_4$, at pH7.2), and 100 μL of the HRP substrate was added to each well and incubated for 1-5 minutes. Signals were subsequently detected using a plate reader (Excitation wavelength=530 nm, Emission wavelength=590 nm, and cutoff wavelength=570 nm).

Figure 2:
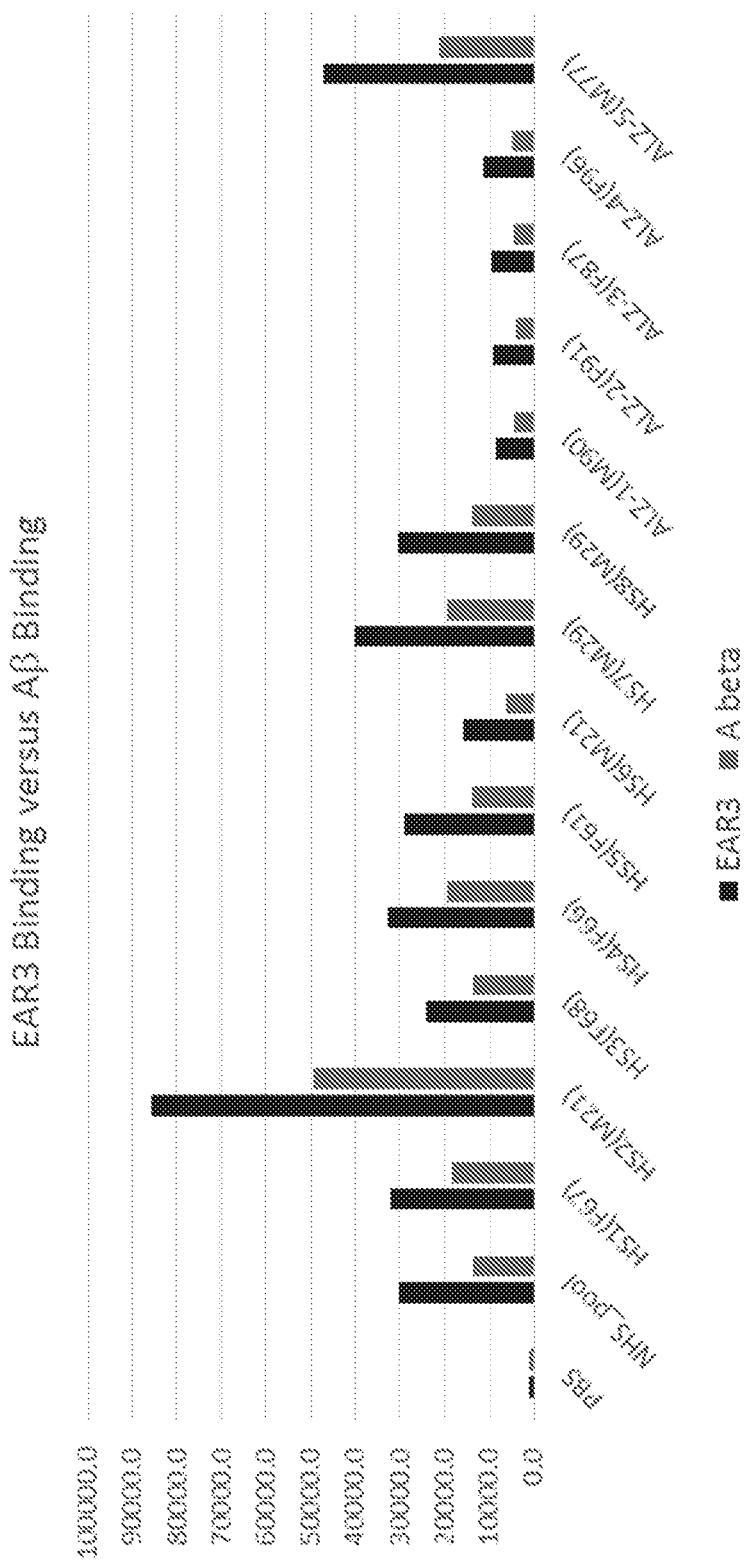
FIG. 2 shows catabody and Aβ-specific auto-antibody levels in healthy (HS1-HS8) individuals or patients with Alzheimer's disease (ALZ-1-5).

FIG. 2 shows the results of the (EAR)$_3$ and Aβ binding assays. Compared to the healthy individuals, 4 out of the 5 AD patients had significant reduction in both the catabody and Aβ-specific auto-antibody serum levels. This result suggests that co-reduction of serum SHD catabody levels and Aβ-specific auto-antibody levels can serve as a biomarker for AD diagnosis.

Example 2. Design and Characterization of Anti-Aβ Catabodies

This example describes the design and characterization of anti-Aβ catabodies based on 3D6, a non-catalytic antibody that specifically binds Aβ.

A. Design of 3D6-D

Previous studies have found that human IgM autoantibodies hydrolyze Aβ via a serine protease-like mechanism. Brain and peripheral Aβ are in equilibrium with each other. Peripheral Aβ hydrolysis may induce depletion of the brain Aβ storage without IgM passage across the BBB. However, IgMs mediate the innate immune response, usually have lower affinity to target antigens, and are more difficult to manufacture. Thus, we sought to engineer an IgG catabody that could hydrolyze Aβ.

Figure 3:
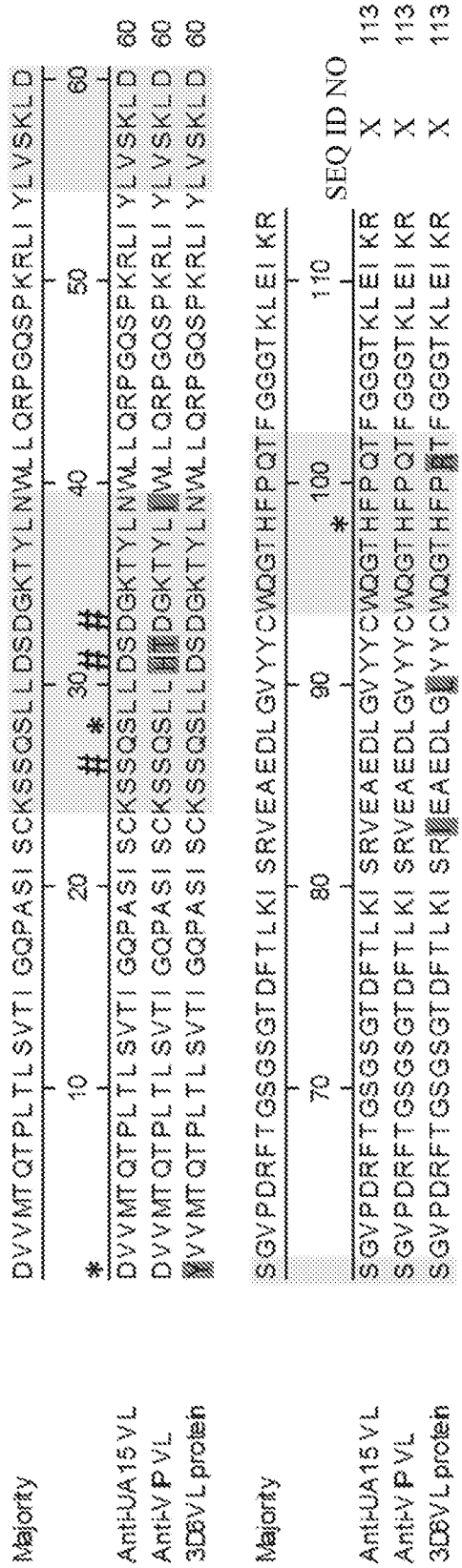
FIG. 3 shows alignment of V$_L$ sequences of two catabodies (anti-UA15 and anti-VP) and non-catalytic anti-Aβ antibody 3D6. Amino acid residues corresponding to the SHD motif are marked with asterisk (*). Amino acid residues that may support catalytic function of the catabodies are marked with pound (#).

SHD catabodies are known to have an SHD motif is the light chain variable region ($V_L$). See. Gao Q S et al. "Site-directed mutagenesis of proteolytic antibody light chain," *J. Mol. Biol.* 253(5): 658 (1995). Thus, we aligned the published $V_L$ Sequences of several Aβ specific IgG non-catalytic antibodies to published $V_L$ sequences of catabodies. We found that the except for having a "SHY" instead of "SHD" motif, murine version of bapineuzumab, 3D6, has high homology to other published catabody $V_L$ sequences, especially to that of the anti-UA15 $V_L$ sequence (Planque S A et al. "Physiological IgM Class Catalytic Antibodies Selective for Transthyretin AMyoid," *J. Biol. Chem.,* 289 (19): 13243-13258 (2014)). The sequence alignment results of the $V_{LS}$ of anti-UA15 (a catabody), anti-VP (a catabody) and 3D6 (anti-Aβ non-catalytic antibody) are shown in FIG. 3.

A 3D6-D antibody was engineered by replacing the Y residue at position 1 of the $V_L$ of 3D6 with a D, and expressed recombinantly and purified. FIG. 4 shows reducing and non-reducing gel electrophoresis of 3D6-D and 3D6 (i.e., 3D6-Y) antibodies, and humanized versions thereof. Sequences of the 3D6-D catabody are shown in Table 2.

B. Catalytic Activity of 3D6-D

The catalytic activity of the 3D6-D antibody was assessed in an EAR-AMC catalytic function assay. Briefly, each well of an ELISA plate was coated with an (100X, Bachem Americas, Inc. Cat. No. 1-1575.0050) at a 1:100 dilution. 3D6-D (400 ng/mL), 3D6-Y (400 ng/mL), trypsin (0.25% trypsin-EDTA at 1:10,000 dilution) was each mixed with an enzymatic assay buffer (50 mM Tris-HCl, pH7.7, 0.1M Glycine, 0.025% Tween-20) and EAR-AMC (100 µM) in PBS buffer. PBS buffer was used as negative control, and IgG1 was used as isotype control. The mixtures were transferred to different wells of an ELISA plate, which was sealed tightly and incubated at 37° C. for 20 hours or 68 hours. At the end of the incubation, signals were detected using a plate reader (Excitation wavelength=360 nm, Emission wavelength=470 nm, and cutoff wavelength=455 nm). EAR-AMC is a substrate of SHD catabodies, which cleave EAR-AMC at the covalent bond between Arg and AMC, thereby releasing AMC.

The results of the EAR-AMC catalytic function assay are shown in FIG. 4. 3D6-D showed potent cleavage activity, but the wild type 3D6 antibody (with a Y residue) did not cleave the EAR-AMC substrate.

C. Aβ-Binding of 3D6-D

Figure 6:
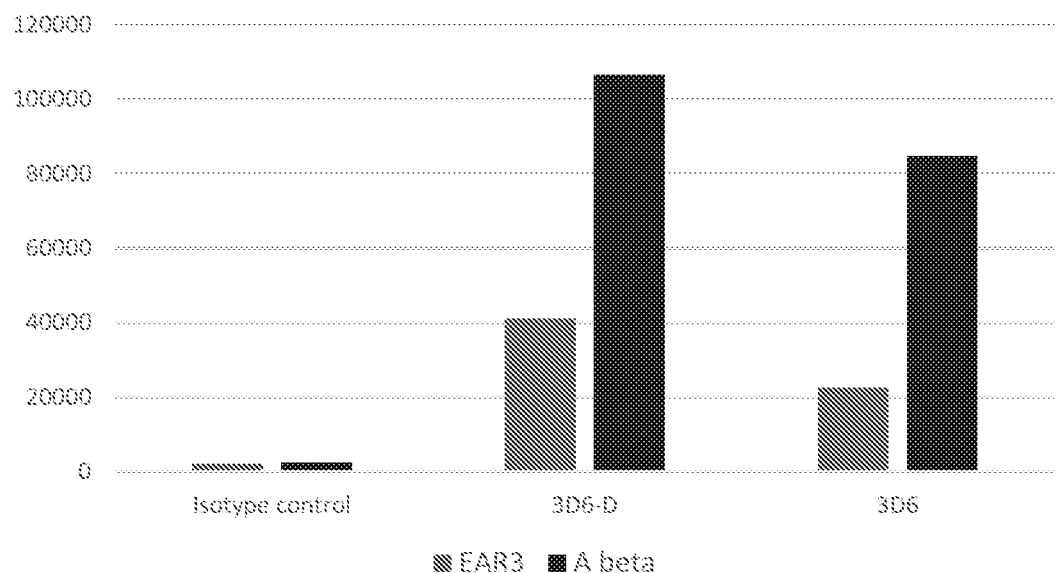
FIG. 6 shows binding of 3D6-D to (EAR)$_3$ (SEQ ID NO: 3) and Aβ.

Binding of 3D6-D, 3D6, or isotype control (IgG1) to (EAR)$_3$ and Aβ were determined using the EAR3 binding assay and Aβ binding assay respectively as described in Example 1. Each antibody was added to the well of the ELISA plate at a concentration of 100 µg/mL. As shown in FIG. 6, 3D6-D has comparable (EAR)$_3$ and Aβ3-binding activity as the 3D6 antibody, which suggests that 3D6-D is a high affinity IgG1 catabody for Aβ.

D. Humanization of 3D6-D

In order to reduce immunogenicity of the 3D6-D catabody, humanized catabodies were produced by grafting CDRs of 3D6-D into human antibody framework sequences. Back-mutations in the human antibody framework sequences to original mouse sequences were further introduced to maintain the affinity of the humanized antibody and to facilitate further development of the antibody. Additionally, the SHD motif and other residues that may support SHD motif catalytic functions (e.g., residues marked "#" in FIG. 3) and/or maintain the conformational structure of the SHD motif were back-mutated to the original mouse sequences. Exemplary humanized 3D6-D antibodies sequences are shown in Table 2.

Binding affinities of humanized 3D6-D catabodies to Aβ were determined using an Aβ binding assay. Briefly, an ELISA plate was coated with an Aβ (1-42) peptide at 1 µg/mL in a coating buffer (0.2M sodium carbonate-bicarbonate buffer, pH 9.4), 100 µL/well at 4° C. overnight. The Aβ peptide was removed and the plate was washed three times with 250 µL/well of a washing buffer (PBST). The plate was then blocked with 200 µL/well of a blocking buffer (1% BSA in PBST) for 1 hour at room temperature, and washed two times with 250 µL/well of the washing buffer. To each well of the plate was added 100 µL of the antibody sample (3× serial dilution in the range of 3 ng/mL to 20 µg/mL) and incubated at room temperature for 1 hour. Samples tested include 3D6-D, humanized 3D6-Y (bapineuzumab), hu3D6-D H1L1, hu3D6-D H1L2, and 3D6-Y. The plate was then washed three times with 250 µL/well of the washing buffer. To each well of the plate was added 100 µL goat anti-Human IgG-HRP (Jackson Immun. Cat. No. 109-035-003) at 1:2,000 dilution in an assay buffer (0.1% BSA/PBST) and incubated for 1 hour at room temperature. The plate was then washed three times with 250 µL/well of the washing buffer. HRP substrate (Amplex Red and $H_2O_2$) was prepared freshly with a developing buffer (3.6 mM $Na_2HPO_4$, 1.4 mM $NaH_2PO_4$, at pH7.2), and 100 µL of the HRP substrate was added to each well and incubated for 1-60 minutes. Signals were subsequently detected using a plate reader (Excitation wavelength=530 nm, Emission wavelength=590 nm, and cutoff wavelength=570 nm).

Figure 7:
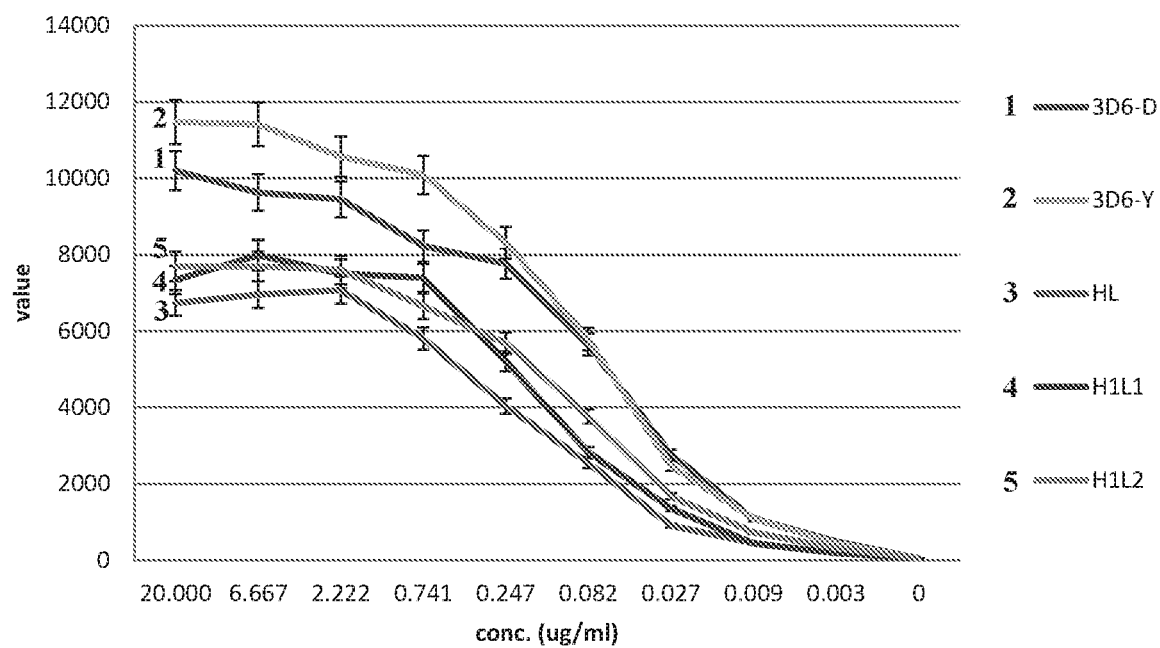
FIG. 7 shows binding of humanized 3D6 catabodies with Aβ.

As shown in FIG. 7, humanized 3D6-D catabodies (hu3D6-D H1L1 and hu3D6-D H1L2) have comparable binding affinities to Aβ as bapineuzumab.

E. Phage Library Panning of 3D6-D Variants

A human scFv/Fab phage library with human germline $V_{HS}$ and the humanized $V_L$ sequences of 3D6-D is panned against Aβ to select for humanized anti-Aβ catalytic scFvs or Fabs. The HC-CDR sequences in the phage library are randomized. The scFvs or Fabs are selected based on high specificity for Aβ. The catalytic activity of the selected scFvs and Fabs is assessed using the EAR-AMC catalytic function assay described in Example 2. The selected anti-Aβ scFvs and Fabs are used to make full-length IgG (e.g., IgG1 or IgG4) catabodies.

Example 3. Determination of Anti-Aβ Autoantibody and SHD Catabody Levels in Human Serums of Alzheimer's Disease (AD) Patients This experiment was carried out to detect anti-Aβ autoantibody levels and SHD catabody (recognizing (EAR)$_3$ peptide) levels in the serum of Alzheimer's disease (AD) patients versus that of healthy individuals.

30 AD serum samples used in this assay included 25 new AD patient serum samples and 5 old AD patient serum samples from Example 1. 8 healthy donor serum (HS) samples came from young adults (20 to 29 years old; HS2, HS6, HS7 and HS8) and old adults (60 to 69 years old; HS1, HS3, HS4 and HS5), as used in Example 1. One pooled healthy donor serum sample served as positive control (NHS; Innovative Research). PBS served as negative control. Total 40 test samples were centrifuged at 16000 g for 10 min, and supernatant was collected for ELISA assays. Each sample was tested in duplicates.

In the EAR3 binding assay, an ELISA plate was coated with an (EAR)$_3$ peptide (SEQ ID NO: 3). (EAR)$_3$ stock (5 mg/mL) was diluted 100 folds with coating buffer (0.2M sodium carbonate-bicarbonate buffer, pH 9.4), with a final concentration of 50 µg/mL, coated 100 µL/well, 4° C. overnight. In the Aβ binding assay, an ELISA plate was coated with biotinylated amyloid (1-42) peptide at a final concentration of 2 µg/mL (1 mg/mL stock was diluted 500 folds) in coating buffer (0.2M sodium carbonate-bicarbonate buffer, pH 9.4), 100 µL/well, 4° C. overnight. The plates were washed three times with 200 µL washing buffer (PBST: 0.1% Tween-20 in phosphate buffer saline "PBS") each time. The plates were then blocked with a blocking buffer (1% BSA in PBST) for 2 hours at room temperature, and washed three times with 200 µL washing buffer (PBST) each time. To each well of the plate was added 100 µL of the corresponding test sample at 1:100 dilution with PBS. All samples were tested in duplicates for each peptide target. See FIG. 9A for loading design. After incubation at 4° C. overnight, the plates were then washed three times with 200 µL washing buffer (PBST) each time. To each well of the plate was added 100 µL of a goat polyclonal antibody against human IgG conjugated to horseradish peroxidase (GAH-HRP; Abeam Cat. No. ab98605) at 1:5000 dilution in blocking buffer (1% BSA in PBST), and incubated for 1 hour at room temperature and protected from exposure to light. The plates were then washed three times with 200 µL washing buffer (PBST) each time. HRP substrate (Amplex Red and $H_2O_2$) was prepared freshly with a developing buffer (3.6 mM $Na_2HPO_4$, 1.4 mM $NaH_2PO_4$, at pH7.2): 20 mL developing buffer+26.6 μL Amplex Red+6.6 μL H$_2$O$_2$. 100 μL of the prepared HRP substrate was added to each well and incubated for 1-5 minutes. Signals were subsequently detected using a plate reader (Excitation wavelength=530 nm, Emission wavelength=590 nm, and cutoff wavelength=570 nm) at 1 min, 5 min, 10 min, 20 min, 30 min, and 60 min, respectively. The average readout from pooled human serum and serum samples of 8 healthy donors served as controls. "% of Control" was calculated as (readout of AD sample) divided by (average readout of pooled human serum and serum of 8 healthy donors), see FIG. 8. The table and bar chart of FIG. 8 were generated based on the readouts in FIGS. 9B-9C.

As can be seen from FIGS. 9B-9C, both binding assays worked well, because the readouts of positive controls (pooled healthy human serum) were much higher than those of PBS negative controls (over 80 times for Aβ binding, and over 100 times for (EAR)$_3$ binding).

As can be seen from FIGS. 8, 9B and 9C, about 70% of AD patients had lower serum levels of anti-Aβ autoantibody compared to control, and about 86.7% of AD patients had lower serum levels of SHD catabody, which recognizes (EAR)$_3$ peptide, compared to control. These data suggest that co-reduction of serum anti-Aβ autoantibodies and SHD catabodies can serve as a good biomarker for AD diagnosis and prognosis.

---

What is claimed is:

1. A method of treating Alzheimer's disease in an individual, comprising administering to the individual an effective amount of an anti-Aβ catabody, wherein the anti-Aβ catabody comprises: (i) an immunoglobulin heavy chain variable domain ($V_H$) comprising the amino acid sequence of SEQ ID NO: 4, and an immunoglobulin light chain variable domain ($V_L$) comprising the amino acid sequence of SEQ ID NO: 5, (ii) a $V_H$ comprising the amino acid sequence of SEQ ID NO: 6, and a $V_L$ comprising the amino acid sequence of SEQ ID NO: 7; (iii) a $V_H$ comprising the amino acid sequence of SEQ ID NO: 6, and a $V_L$ comprising the amino acid sequence of SEQ ID NO: 8; (iv) a $V_H$ comprising the amino acid sequence of SEQ ID NO: 19, and a $V_L$ comprising the amino acid sequence of SEQ ID NO: 21; (v) a $V_H$ comprising the amino acid sequence of SEQ ID NO: 20, and a $V_L$ comprising the amino acid sequence of SEQ ID NO: 21; (vi) a $V_H$ comprising the amino acid sequence of SEQ ID NO: 19, and a $V_L$ comprising the amino acid sequence of SEQ ID NO: 22; or (vii) a $V_H$ comprising the amino acid sequence of SEQ ID NO: 20, and a $V_L$ comprising the amino acid sequence of SEQ ID NO: 22.

2. The method of claim 1, wherein the anti-Aβ catabody cleaves a substrate having the formula EAR-AMC (SEQ ID NO: 1).

3. The method of claim 1, wherein the anti-Aβ catabody is a full-length IgG antibody.

4. The method of claim 3, wherein the anti-Aβ catabody comprises an IgG1 or IgG4 Fc region.

5. The method of claim 1, wherein the anti-Aβ catabody is a full-length IgM antibody.

* * * * *